(12) United States Patent
Elliman et al.

(10) Patent No.: US 11,268,067 B2
(45) Date of Patent: Mar. 8, 2022

(54) METHODS OF ISOLATION AND USE OF CD39 STROMAL STEM CELLS

(71) Applicant: ORBSEN THERAPEUTICS LIMITED, Galway (IE)

(72) Inventors: Stephen J. Elliman, Rosscahil (IE); Jack Kavanaugh, Los Angeles, CA (US); Larry A. Couture, Claremont, CA (US); Lisa O'Flynn, Galway (IE)

(73) Assignee: ORBSEN THERAPEUTICS LIMITED, Galway (IE)

( * ) Notice: Subject to any disclaimer, the term of this patent is extended or adjusted under 35 U.S.C. 154(b) by 0 days.

(21) Appl. No.: 16/630,791

(22) PCT Filed: Jul. 12, 2018

(86) PCT No.: PCT/IB2018/000939
§ 371 (c)(1),
(2) Date: Jan. 13, 2020

(87) PCT Pub. No.: WO2019/012334
PCT Pub. Date: Jan. 17, 2019

(65) Prior Publication Data
US 2020/0149012 A1 May 14, 2020

Related U.S. Application Data

(60) Provisional application No. 62/534,631, filed on Jul. 19, 2017, provisional application No. 62/532,800, filed on Jul. 14, 2017.

(51) Int. Cl.
| | | |
|---|---|---|
| *A61K 35/35* | (2015.01) | |
| *C12N 5/0775* | (2010.01) | |
| *A61P 25/28* | (2006.01) | |
| *A61P 1/16* | (2006.01) | |
| *A61P 37/06* | (2006.01) | |
| *A61P 19/02* | (2006.01) | |
| *A61P 13/12* | (2006.01) | |
| *A61P 17/02* | (2006.01) | |
| *A61P 11/00* | (2006.01) | |
| *A61P 29/00* | (2006.01) | |
| *A61K 9/00* | (2006.01) | |
| *A61K 9/06* | (2006.01) | |
| *G01N 33/543* | (2006.01) | |

(52) U.S. Cl.
CPC .......... *C12N 5/0662* (2013.01); *A61K 9/0014* (2013.01); *A61K 9/0019* (2013.01); *A61K 9/06* (2013.01); *A61K 35/35* (2013.01); *A61P 1/16* (2018.01); *A61P 11/00* (2018.01); *A61P 13/12* (2018.01); *A61P 17/02* (2018.01); *A61P 19/02* (2018.01); *A61P 25/28* (2018.01); *A61P 29/00* (2018.01); *A61P 37/06* (2018.01); *G01N 33/54313* (2013.01)

(58) Field of Classification Search
None
See application file for complete search history.

(56) References Cited

U.S. PATENT DOCUMENTS

| | | |
|---|---|---|
| 5,486,359 A | 1/1996 | Caplan et al. |
| 5,726,058 A | 3/1998 | Jalkanen et al. |
| 6,355,239 B1 | 3/2002 | Bruder et al. |
| 6,531,295 B1 | 3/2003 | Saunders et al. |
| 10,124,038 B2 | 11/2018 | Elliman |
| 10,251,934 B2 | 4/2019 | Ellman |
| 10,920,197 B2 | 2/2021 | Elliman |
| 11,026,994 B2 * | 6/2021 | Elliman ................. C07K 14/71 |
| 2003/0225018 A1 | 12/2003 | Ekker et al. |
| 2004/0258670 A1 | 12/2004 | Laughlin et al. |
| 2005/0059147 A1 | 3/2005 | Seshi |
| 2005/0226864 A1 | 10/2005 | Hinton et al. |
| 2006/0078993 A1 | 4/2006 | Phan et al. |
| 2007/0264239 A1 | 11/2007 | Huard et al. |
| 2008/0241246 A1 | 10/2008 | Sakthivel et al. |
| 2010/0172885 A1 | 7/2010 | Pittenger et al. |
| 2010/0196329 A1 | 8/2010 | Ra et al. |
| 2010/0247577 A1 | 9/2010 | Foussat et al. |
| 2012/0207725 A1 | 8/2012 | Cho et al. |
| 2014/0356398 A1 | 12/2014 | Riddell et al. |
| 2015/0030615 A1 | 1/2015 | Derr et al. |
| 2015/0037292 A1 | 2/2015 | Ellman |
| 2016/0058832 A1 * | 3/2016 | Elliman .................. A61P 17/02 424/139.1 |
| 2016/0215265 A1 | 7/2016 | Elliman |
| 2016/0271211 A1 | 9/2016 | Elliman et al. |

(Continued)

FOREIGN PATENT DOCUMENTS

| | | |
|---|---|---|
| CN | 1678734 A | 10/2005 |
| EP | 1795588 A1 | 6/2007 |

(Continued)

OTHER PUBLICATIONS (Abstract C34.6) Abstracts of papers presented at GLYCO XVI, XVI International Symposium on Glycoconjugates, Aug. 19-24, 2001, The Hague, The Netherlands, Glycoconjugate Journal, 18(1-2): 1-202, 2001.

Alvarez-Viejo: CD271 as a marker to identify mesenchymal stem cells from diverse sources before culture. World Journal of Stem Cells, vol. 7, No. 2, Jan. 1, 2015, p. 470.

Australian Patent Application No. 2013217870 Examination Report dated Apr. 24, 2018.

(Continued)

*Primary Examiner* — Ralph J Gitomer
(74) *Attorney, Agent, or Firm* — Wilson Sonsini Goodrich & Rosati

(57) ABSTRACT

Disclosed herein are methods of isolating SDC2+ stromal stem cells by expression of surface marker CD39. Also disclosed herein are stromal stem cells isolated by said methods.

9 Claims, 19 Drawing Sheets

(56) References Cited

U.S. PATENT DOCUMENTS

| | | | |
|---|---|---|---|
| 2019/0015331 A1* | 1/2019 | Elliman | A61P 3/00 |
| 2020/0149110 A1 | 5/2020 | Targan et al. | |
| 2020/0158725 A1 | 5/2020 | Singh et al. | |
| 2021/0154235 A1* | 5/2021 | Couture | A61L 15/44 |

FOREIGN PATENT DOCUMENTS

| | | |
|---|---|---|
| EP | 2545928 A1 | 1/2013 |
| EP | 3271396 A1 | 1/2018 |
| EP | 3416964 A4 | 9/2019 |
| JP | 2013508353 A | 3/2013 |
| JP | 2016516797 A | 6/2016 |
| JP | 2017532965 A | 11/2017 |
| KR | 20080075959 A | 8/2008 |
| KR | 20100106744 A | 10/2010 |
| KR | 20120013915 A | 2/2012 |
| KR | 101309910 B1 | 9/2013 |
| WO | WO-02087609 A1 | 11/2002 |
| WO | WO-03046141 A2 | 6/2003 |
| WO | WO-03062386 A2 | 7/2003 |
| WO | WO-2004003179 A1 | 1/2004 |
| WO | WO-2007122823 A1 | 11/2007 |
| WO | WO-2008100083 A1 | 8/2008 |
| WO | WO-2009012357 A2 | 1/2009 |
| WO | WO-2009105624 A2 | 8/2009 |
| WO | WO-2010065239 A1 | 6/2010 |
| WO | WO-2011153458 A2 | 12/2011 |
| WO | WO-2012111997 A2 | 8/2012 |
| WO | WO-2013117761 A1 | 8/2013 |
| WO | WO-2013172793 A1 | 11/2013 |
| WO | WO-2014168548 A2 | 10/2014 |
| WO | WO-2014170411 A1 | 10/2014 |
| WO | WO-2015038075 A1 | 3/2015 |
| WO | WO-2016154019 A1 | 9/2016 |
| WO | WO-2017122095 A1 | 7/2017 |
| WO | WO-2018220442 A2 | 12/2018 |
| WO | WO-2019012334 A2 | 1/2019 |
| WO | WO-2020035741 A2 | 2/2020 |
| WO | WO-2021038289 A1 | 3/2021 |

OTHER PUBLICATIONS

Australian Patent Application No. 2013217870 Examination Report No. 1 dated Nov. 1, 2017.
Australian Patent Application No. 2014255755 Examination Report No. 1 dated Oct. 10, 2017.
Australian Patent Application No. 2014255755 Examination Report No. 2 dated Jun. 27, 2018.
Bermadez-Lugo et al.: Exploration of the valproic acid binding site on histone deacetylase 8 using docking and molecular dynamic simulations. Journal of Molecular Modeling, 18(6):2301-2310, 2011.
Brazilian Patent Application No. 112015026258-9 Search Report dated Oct. 29, 2019.
British Society for Matrix Biology—Spring 2012 Meeting Report. International Journal of Experimental Pathology, 94:A1-A48, 2013.
Canadian Patent Application No. 2863821 Examination Report dated Nov. 6, 2018.
Carlotti et al.: Isolated human islets contain a distinct population of mesenchymal stem cells, Islets, p. 164-173 May/Jun. 2010.
Chinese Patent Application No. 201380019351.0 Second Office Action dated Jun. 10, 2016.
Chinese Patent Application No. 201380019351.0 Third Office Action dated Jan. 12, 2017.
Christianson and Belting: Heparan sulfate proteoglycan as a cell-surface endocytosis receptor. Matrix Biology, 35:51-55, 2014.
Chung et al.: Human Embryonic Stem Cell Lines Generated without Embryo Destruction. Cell Stem Cell, vol. 2, No. 2, 2008, pp. 113-117.
CN201480025184.5 Office Action dated Jul. 4, 2018.
Costabel et al.: Pirfenidone in idiopathic pulmonary fibrosis: Expert panel discussion on the management of drug-related adverse events. Adv. Ther., 31:375-391, 2014.
Cuthbert et al.: Single-platform quality control assay to quantify multipotential stromal cells in bone marrow aspirates prior to bulk manufacture or direct therapeutic use. Cytotherapy, 2012, vol. 14, No. 4, pp. 431-440.
Database: NCBI Reference Sequence: NP_002989.1 (2 pgs.) (Jan. 20, 2003).
Davey et al.: Mesenchymal stem cell-based treatment for microvascular and secondary complications of diabetes mellitus. Frontiers in Endocrinology 5:86 [1-16]. doi: 10.3389/fendo.2014.00086 (2014).
Dieudonne et al.: High Wnt signaling represses the proapoptotic proteoglycan syndecan-2 in osteosarcoma cells. Cancer Res 70(13):5399-5408 (2010).
Dieudonne et al.: Targeted inhibition of T-cell factor activity promotes syndecan-2 expression and sensitization to doxorubicin in osteosarcoma cells and bone tumors in mice. J Bone Miner Res 27(10):2118-2129 (2012).
Duffy et al.: Mesenchymal stem cell inhibition of T-helper 17 cell-differentiation is triggered by cell-cell contact and mediated by prostaglandin E2 via the EP4 receptor. European Journal of Immunol., 41:2840-2851, 2011.
Eskildsen et al.: MicroRNA-138 regulates osteogenic differentiation of human stromal (mesenchymal) stem cells in vivo. PNAS, 108(15):6139-6144, 2011.
Essner et al.: Syndecan-2. International Journal of Biochemistry and Cell Biology. 38(2):152-156, 2006.
European Patent Application No. 14718403.0 Communication dated Apr. 6, 2017.
European Patent Application No. 14718403.0 Communication dated Mar. 6, 2018.
European Patent Application No. 14718403.0 Examination Report dated Jan. 2, 2019.
European Patent Application No. 15158384.6 Communication dated Apr. 7, 2017.
European Patent Application No. 15158384.6 Extended European Search Report dated Jul. 8, 2015, 10 pages.
European Patent Application No. 16714673.7 Office Action dated Sep. 12, 2018.
European Patent Application No. 18190005.1 European Search Report dated May 3, 2019.
Final Report Summary—REDDSTAR (Repair of Diabetic Damage by Stromal Cell Administration). European Commission https://cordis.europa.eu/result/rcn/197094_en.html 1-28 (2017).
Final Report Summary—Core of Report—REDDSTAR (Repair of Diabetic Damage by Stromal Cell Administration). European Commission https://cordis.europa.eu/docs/results/305/305736/final1-reddstar-final-report-core-of-report.pdf 1-44 (2017).
Frantz et al.: The extracellular matrix at a glance. Cell Science at a Glance 123, (2010), 4195-4200.
GB1202319.8 Search Report dated Jun. 11, 2012, 3 pages.
Gronthos et al.: Molecular and cellular characterisation of highly purified stromal stem cells derived from human bone marrow. (2003) Journal of Cell Science, vol. 116:1827-1835.
Hagymasi et al.: Stem cell treatment in the treatment of gastrointestinal diseases. Orvosi Hetilap. 149(31):1449-1455 (2008).
Hayes et al.: Mesenchymal stem cells—a promising therapy for Acute Respiratory Distress Syndrome. F1000 Med Rep. 4:2:1-7 (2012).
Hohki et al.: Blockade of interleukin-6 signaling suppresses experimental autoimmune uveoretinitis by the inhibition of inflammatory Th17 responses. Experimental Eye Research, 91:162-170, 2010.
Horwitz et al.: Clarification of the nomenclature for MSC: The international society for cellular therapy position statement. Cytotherapy, 7:393-395, 2005.
Hsu et al.: Neural stem cells, neural progenitors, and neurotrophic factors. Cell Transplant 16(2):133-150 (2007).
Huang et al.: Prognostic significance of altered expression of SDC2 and CYR61 in esophageal squamous cell carcinoma. Oncology Reports, 21:1123-1129, 2009.
Human/Mouse Integrin [alpha]11 Antibody. Jun. 30, 2015 (Jun. 30, 2015), 1 page, Retrieved from the Internet: URL:http://www.rndsystems.com/pdf/MAB4235.pdf.
Indian Patent Application No. 1777/KOLNP/2014 Office Action date May 31, 2018.

(56) References Cited

OTHER PUBLICATIONS

International Patent Application No. PCT/IB2018/000687 International Search Report and Written Opinion dated Dec. 5, 2018.
International Patent Application No. PCT/IB2018/000939 International Search Report and Written Opinion dated Dec. 19, 2018.
Japanese Patent Application No. 2016-508166 Office Action dated Jun. 12, 2018.
Japanese Patent Application No. 2016-508166 Office Action dated Sep. 25, 2017.
Japanese Patent Application No. 2017-550240 Office Action dated Mar. 2, 2020.
Jones et al.: Large-Scale Extraction and Characterization of CD271+ Multipotential Stromal Cells From Bone in Health and Osteoarthritis, Arthritis & Rhuematism, vol. 62, No. 7, Jul. 2010, pp. 1944-1954.
Kaltz N et al: Novel markers of mesenchymal stem cells defined by genome-wide gene expression analysis of stromal cells from different sources. Experimental Cell Research, Academic Press, US, vol. 316, No. 16, (Oct. 1, 2010), pp. 2609-2617.
Keifer et al.: Inhibition of NF-êB Activity by Thalidomide through Suppression of IêB Kinase Activity, Journal of Biological Chemistry, American Society for Biochemistry and Molecular Biology, US, vol. 276, No. 25, Jun. 22, 2001, pp. 22382-22387.
Khan et al.: CD4+ T Cell-derived Novel Peptide Thp5 Induces Interleukin-4 Production in CD4+ T Cells to Direct T Helper 2 Cell Differentiation. J Biol Chem, 287, 2830-2835, 2011.
Kozanoglu et al.: Human bone marrow mesenchymal cells express NG2: possible increase in discriminative ability of flow cytometry during mesenchymal stromal cell identification. Cytotherapy (2009) vol. 11, No. 5, pp. 527-533.
KR1317507 Abstract from STN CAPlus database (1 pg) (2015).
Lambaerts et al.: The signalling mechanisms of syndecan heparen sulphate proteoglycans Current Opinion Cell Biol., 21(5):662-669 (2009).
Lim et al.: Cell surface heparan sulfate proteoglycans control adhesion and invasion of breast carcinoma cells Molecular Cancer, 14:15, 18 pages, 2015.
Lim et al.: Syndecan-2 regulation of morphology in breast carcinoma cells is dependent on RhoGTPases. Biochimica et Biophysica Acta, 1840:2482-2490, 2014.
Llinas et al.: Expression profiles of novel cell surface molecules on B-cell subsets and plasma cells as analyzed flow cytometry, Immunology Letters, vol. 134, No. 2, Jan. 30, 2011, pp. 113-121.
Lotufo et al.: Expression of cell-surface heparan sulfate proteoglycans in human cyclosporin-induced gingival overgrowth. J.Periodont Res., 42:553-558, 2007.
Ludlow et al.: Large scale production of extracellular vesicles in a hollow fiber bioreactor system. Poster. www.FiberCellSystems. com, 1 page, 2016.
Lyons and Parish: Determination of lymphocyte division by flow cytometry. Journal of Immunological Methods, 171:131-137, 1994.
Manon-Jensen et al.: Proteoglycans in health and disease: the multiple roles of syndecan shedding FEBS Journal, 277(19):3876-3889, 2010.
Matesanz-Isabel et al.: New B-cell CD molecules. Immunology Letters, 2011, vol. 134, No. 2, pp. 104-112.
Mendez-Ferrer et al.: Mesenchymal and haematopoietic stem cells form a unique bone marrow niche Nature, 466:829-836 (2010).
Mendez-Ferrer et al.: Mesenchymal and haematopoietic stem cells form a unique bone marrow niche Nature, 466:829-836 (2010) Supplementary Information, 21 pages.
Mukhopadhyay et al.: Syndecan-2 and Decorin: Proteoglycans With a Difference—Implications in Keloid Pathogenesis, Journal of Trauma Injury Infection and Critical Care, 68(4):999-1008, 2010.
Mytilinalou et al.: Research Communication: Syndecan-2 is a key regulator of transforming growth factor beta 2/Smad2-mediated adhesion in fibrosarcoma cells. IUBMB Life, 65(2):134-143 (2013).
Nauta et al.: Chapter 2, Humoral and Cellular Immunity, in: Statistics in Clinical Trials, Berlin: Springer-Verlag, p. 13-17, 2011.

Nierhoff et al.: New cell surface markers for murine fetal hepatic stem cells identified through high density complementary DNA microarrays. Hepatology 46(2):535-547 (2007).
Nish et al.: T cell-intrinsic role of IL-6 signaling in primary and memory responses. Elife, 3:e01949, 21 page (2014).
Paris et al.: Opposing Roles of Syndecan-1 and Syndecan-2 in Polyethyleneimine-mediated Gene Delivery. J Biol Chem, 283:7697-7704, 2008.
Parish: Fluorescent dyes for lymphocyte migration and proliferation studies. Immunology and Cell Biology, 77:499-508, 1999.
Park et al.: Syndecan-2 mediates adhesion and proliferation of colon carcinoma cells. The Journal of Biological Chemistry, 277(33):29730-29736, 2002.
Patil et al.: Enhancement of wound healing with increased angiogenesis in a diabetic rabbit ulcer model by topical application of CD362+ human mesenchymal stem cells (Cyndacel-M) seeded in Excellagen scaffold. Tissue Engineering Part A, 21(Supp. 1):S90 XP05509717 (2015).
PCT Patent Application No. PCT/EP2016/056065 International Search Report and Written Opinion dated May 20, 2016.
PCT Patent Application No. PCT/US2016/023178 International Search Report and Written Opinion dated Jun. 13, 2016.
PCT/EP2013/052692 International Preliminary Report on Patentability under Chapter II completed Mar. 13, 2014.
PCT/EP2013/052692 International Search Report completed Jun. 10, 2013.
PCT/EP2013/052692 Written Opinion Report completed Jun. 10, 2013.
PCT/EP2014/057830 International Preliminary Report On Patentability dated Oct. 20, 2015.
PCT/EP2014/057830 International Search Report and Written Opinion dated Jul. 17, 2014.
PCT/IB2017/000091 International Preliminary Report on Patentability dated Jul. 26, 2018.
PCT/IB2018/000687 International Preliminary Report on Patentability dated Dec. 3, 2019.
PCT/IB2018/000687 International Search Report and Written Opinion dated May 12, 2018.
PCT/US2016/023178 International Preliminary Report on Patentability dated Sep. 26, 2017.
PCT/US2017/000091 International Search Report and Written Opinion dated May 12, 2017.
Pennock et al.: T cell response: naive to memory and everything in between. Adv. Physiol. Educ. 37:273-283 (2013).
Rovira-Clave et al.: Syndecan-2 can promote clearance of T-cell receptor/CD3 from the cell surface. Immunology, 137(3):214-225 (Nov. 2012):E-Pub: Oct. 2, 2012.
Rozemuller et al.: Prospective isolation of mesenchymal stem cells from multiple mammalian species using cross-reacting anti-human monoclonal antibodies. Stem Cells and Development, vol. 19, No. 12, Dec. 1, 2010, pp. 1911-1921.
Ruiz et al.: Syndecan-2 is a novel target of insulin-like growth factor binding protein-3 and is over-expressed in fibrosis. Pios One, 7(8):1-4, 2012.
Russian Patent Application No. 2014136711 Office Action dated Jun. 1, 2017.
Russian Patent Application No. 2014136711 Official Action dated Feb. 23, 2017.
Russian Patent Application No. 2015148769 Office Action dated Mar. 19, 2018.
Russian Publication No. 2014136711A published Mar. 27, 2016.
Sanz-Nogués et al.: Angiogenic assessment of ORBCEL TM, a novel stromal cell population for treating Critical Limb Ischaemia (CLI); Cytotherapy, vol. 19, S198 (2017).
Sattler et al.: Inhibition of T-Cell Proliferation by Murine Multipotent Mesenchymal Stromal Cells is Mediated by CD39 Expression and Adensoine Generation, Cell Transplantation, vol. 20, No. 8, Sep. 1, 2011, pp. 1221-1230.
Shi et al.: Syndecan-2 exerts antifibrotic effects by promoting caveolin-1-mediated transforming growth factor-β receptor I internalization and inhibiting transforming growth factor-β1 signaling. Am J Respir Crit Care Med, 188:831-841, 2013.

(56) References Cited

OTHER PUBLICATIONS

Si et al.: CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Silva et al.: The Profile of Gene Expression of Human Marrow Mesenchymal Stem Cells (2003) Stem Cells: vol. 21: 661-669.
Stepp et al.: Syndecan-1 and its expanding list of contacts. Advances in Wound Care, 4(4):235-249, 2015.
Tang et al.: Calcitriol suppresses antiretinal autoimmunity through inhibitory effects on the Th17 effector response. The Journal of Immunology, 182:4624-4632, 2009.
Technical Data Sheet, Purified Mouse Anti-human CD271, Jun. 6, 2013, p. 1-2.
Teixe et al.: Corrigendum to Syndecan-2 and -4 expressed on activated primary human CD4+lymphocytes can regulate T cell activation. Molecular Immunology, 51:368, 2012.
Teixe et al.: Syndecan-2 and -4 expressed on activated primary human CD4+ lymphocytes can regulate T cell activation. Molecular Immunology, 45:2905-2919, 2008.
Theocharis et al.: Insights into the key roles of proteoglycans in breast cancer biology and translational medicine. Biochimica et Biophysica Acta, 1855:276-300, 2015.
Turashev et al.: Condition, destruction and reconstruction of the pericellular carbohydrate membrane of the luminal vascular surface in atherogenesis, Cardiological bulletin 2(2):64-68 (2007) (English Abstract).
U.S. Appl. No. 14/377,597 Final Office Action dated Jan. 14, 2019.
U.S. Appl. No. 14/377,597 Office Action dated Apr. 7, 2016.
U.S. Appl. No. 14/377,597 Office Action dated Aug. 15, 2018.
U.S. Appl. No. 14/377,597 Office Action dated Feb. 20, 2020.
U.S. Appl. No. 14/377,597 Office Action dated Jan. 30, 2017.
U.S. Appl. No. 14/377,597 Office Action dated May 12, 2017.
U.S. Appl. No. 14/377,597 Office Action dated Nov. 6, 2015.
U.S. Appl. No. 14/377,597 Office Action dated Oct. 7, 2019.
U.S. Appl. No. 14/377,597 Office Action dated Sep. 9, 2016.
U.S. Appl. No. 14/785,001 Final Office Action dated Jun. 27, 2018.
U.S. Appl. No. 14/785,001 Office Action dated Dec. 15, 2017.
U.S. Appl. No. 14/785,001 Office Action dated Feb. 15, 2017.
U.S. Appl. No. 14/785,001 Office Action dated Jun. 20, 2016.
U.S. Appl. No. 15/074,681 First Action Interview Pilot Program Pre-Interview Communication dated Dec. 9, 2016.
U.S. Appl. No. 15/074,681 Office Action dated Apr. 27, 2017.
U.S. Appl. No. 15/074,681 Office Action dated Nov. 2, 2017.
U.S. Appl. No. 15/074,681 Restriction Requirement dated Aug. 22, 2016.
U.S. Appl. No. 15/089,435 Final Office Action dated Sep. 3, 2019.
U.S. Appl. No. 15/089,435 Non-Final Office Action dated Nov. 14, 2018.
U.S. Appl. No. 15/089,435 Office Action dated Oct. 4, 2017.
U.S. Appl. No. 16/009,048 Office Action dated Dec. 13, 2019.
U.S. Appl. No. 16/009,048 Restriction Requirement dated Jun. 28, 2019.
U.S. Appl. No. 16/254,378 Office Action dated Apr. 16, 2020.
U.S. Appl. No. 16/562,206 Office Action dated Dec. 12, 2019.
U.S. Appl. No. 16/562,206 Office Action dated May 11, 2020.
UNIPROT:P34741, XP002726498, 3 pages, printed Jun. 26, 2014, http://ibis.internal.epo.org/exam/dbfetch.jsp?id=UNIPROT• P3474I.
Wieczorek et al.: Gene expression profile of mouse bone marrow stromal cells determined by cDNA microarray analysis.Cell Tissue Res. 311(2):227-237 (2003).
Xian et al.: Syndecans as receptors and organizers of the extracellular matrix. Cell Tissue Res. 339:31-46 (2010).
Yan et al.: Migration of Dorsal Aorta Mesenchymal Stem Cells Induced by Mouse Embryonic Circulation, Dynamics 240: 65-74 (2011).
Canadian Patent Application No. 2863821 Examination Report dated Jun. 2, 2021.
Nombela-Arrieta et al.: The elusive nature and function of mesenchymal stem cells. Nature Rev Mol Cell Bio. 12:126-131 (2011).
U.S. Appl. No. 14/377,597 Final Office Action dated Oct. 1, 2020.
U.S. Appl. No. 14/377,597 Office Action dated Jun. 30, 2021.
U.S. Appl. No. 15/089,435 Office Action dated Jun. 10, 2020.
U.S. Appl. No. 16/009,048 Final Office Action dated Jul. 24, 2020.
U.S. Appl. No. 16/562,206 Final Office Action dated Nov. 27, 2020.
U.S. Appl. No. 16/630,791 Office Action dated Jun. 25, 2021.

\* cited by examiner

40k   Cfu-f = 1/2,352
10k   Cfu-f = 1/1,666

200k  Cfu-f = 1/9,090
100k  Cfu-f = 1/9,375

FIG. 2A
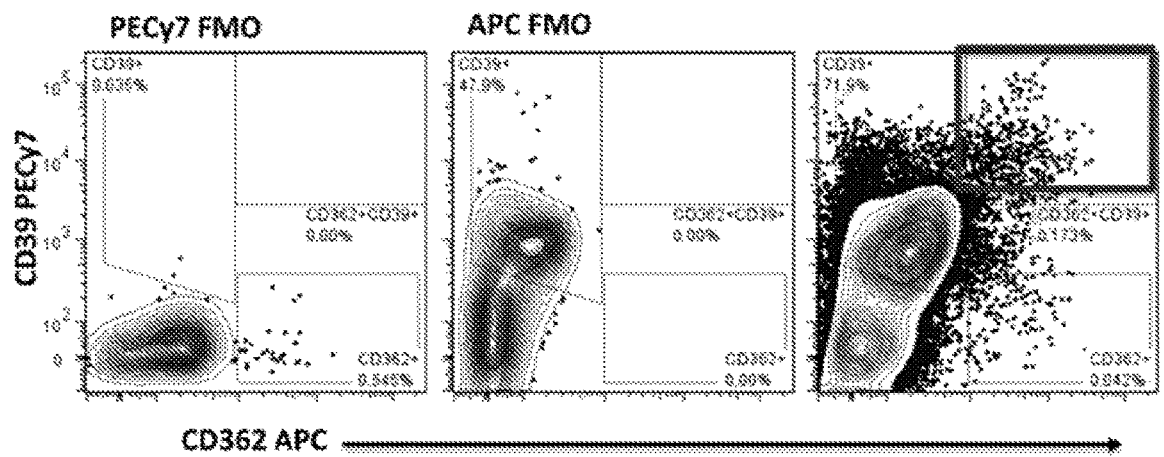
FIG. 2B
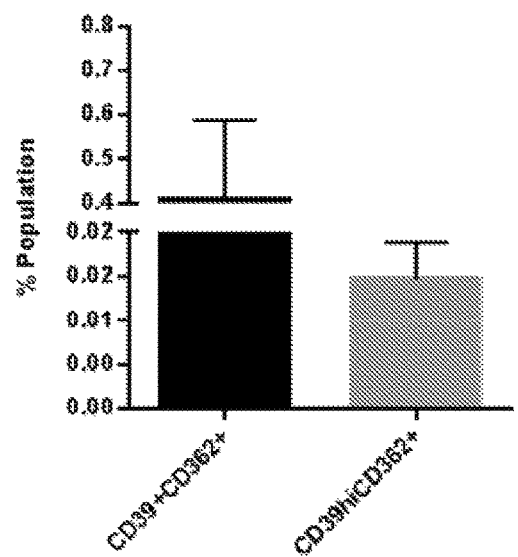
FIG. 2C
| Population | Wild Type | CD362+ | CD39+CD362+ | CD39 | -/- |
|---|---|---|---|---|---|
| Sort 1 cfu-F | 1/50000 | 1/100 | 1/46 | 0 | 0 |
| Sort 2 cfu-F | 1/19047 | 1/11 | 1/26 | 0 | 0 |
| Sort 3 cfu-F | 1/18750 | 0 | 1/4 | 0 | 0 |

One way anova p<0.01

One way anova p<0.01

METHODS OF ISOLATION AND USE OF CD39 STROMAL STEM CELLS

CROSS-REFERENCE

This application is a U.S. National Stage of International Application No. PCT/IB2018/000939, filed Jul. 12, 2018, which claims the benefit of U.S. Provisional Application Nos. 62/532,800, filed Jul. 14, 2017, and 62/534,631, filed Jul. 19, 2017, each of which is incorporated herein by reference in its entirety.

RELATED APPLICATIONS

This application incorporates by reference PCT Application No. PCT/IB2017/000091, filed on Jan. 13, 2017, in its entirety.

BACKGROUND

Mesenchymal stem cells (e.g., mesenchymal stromal stem cells and stromal cells) have been shown to have therapeutic value in treating a variety of diseases. These cells have been found to associate with arterioles, sinusoidal endothelium and high endothelial vesicles in vivo, where they can control endothelial cell activation and the trafficking of immune cells from the vasculature into target tissues. In addition mesenchymal stem cells have been shown to have immunosuppressive and anti-inflammatory properties such as avoiding allogeneic rejection and of inhibition immune cells, such as natural killer cells, neutrophils, dendritic cells, monocyte/macrophages and lymphocytes. Furthermore, mesenchymal stem cells have been found to produce immunosuppressing cytokines such as hepatocyte growth factor (HGF), IL-10, TGFβ1, cyclooxygenase 1 and 2, Syndecan-2 and PGE-2. The immunosuppressive activity of mesenchymal stem cells has been found to be increased in the presence of inflammatory stimuli, specifically interferon-gamma. These properties make mesenchymal stem cells and derivatives thereof (e.g., mesenchymal stromal stem cells, stromal cells, and exosomes produced by mesenchymal stem cells) particularly intriguing in their potential to treat disease.

SUMMARY

Provided herein are methods of isolating a population of SDC2+ stromal stem cells from a mixed population of mammalian cells. Methods comprise one or more of the steps of (a) contacting the mixed population of mammalian cells to a CD39 binding agent; (b) isolating cells bound to the CD39 binding agent; and (c) measuring SDC2+ cell abundance in the isolated cells, thereby isolating the population of SDC2+ stromal stem cells. In some cases, the population of SDC2+ stromal stem cells comprises a human, a mouse, a rat, or an equine cell. In some instances, a mixed population of mammalian cells is obtained from a source selected from at least one of bone marrow, adipose tissue, skeletal muscle, endometrium, placenta, umbilical cord, Wharton's jelly, and cells derived from pluripotent cells. A number of CD39 binding agents are consistent with the disclosure herein. Often, the CD39 binding agent comprises an antibody. In some cases, the antibody is raised to a CD39 antigen. In some instances, the antibody comprises a variable domain that specifically binds to at least one mammalian CD39 protein. Often, the antibody specifically binds to at least one of a human, a mouse, a rat, and equine CD39 protein. In some cases, the antibody is conjugated to a fluorophore. Sometimes, the antibody is conjugated to a bead. Often, at least 20% of the population of SDC2+ stromal stem cells is SDC2+. In some cases, at least 40% of the population of SDC2+ stromal stem cells is SDC2+. Often, at least 70% of the population of SDC2+ stromal stem cells is SDC2+. In some cases, isolating the cells bound to the CD39 binding agent comprises fluorescence activated cell sorting. In some instances, isolating the cells bound to the CD39 binding agent comprises magnetic-activated cell sorting. Often, the method comprises culturing the isolated cells. In some cases, at least 90% of the SDC2+ stromal stem cells are CD45−. In some cases, the population of SDC2+ stromal stem cells further comprises CD25+ FoxP3+ regulatory T cells. In some cases, the method comprises genetically modifying the cells to overexpress an apyrase. In some cases, the method comprises genetically modifying the cells to overexpress CD39. In some cases, the method comprises genetically modifying the cells to overexpress CD39L3. In some cases, the method comprises genetically modifying the cells to overexpress CD73.

Also provided herein are methods of preparing an immunomodulatory composition. Provided methods comprise a population of SDC2+ stromal stem cells, the method comprising (a) contacting a mixed population of mammalian cells to a CD39 binding agent; (b) isolating cells bound to the CD39 binding agent; and (c) measuring SDC2+ cell abundance in the isolated cells. In some cases, the population of SDC2+ stromal stem cells is a population of human, a mouse, a rat, or an equine cells. Often, the mixed population of mammalian cells are obtained from a source selected from at least one of bone marrow, adipose tissue, skeletal muscle, endometrium, placenta, umbilical cord, Wharton's jelly, and cells derived from pluripotent cells. In some cases, the CD39 binding agent comprises an antibody. Often, the antibody is raised to a CD39 antigen. In some instances, the antibody comprises a variable domain that specifically binds to at least one mammalian CD39 protein. In some cases, the antibody specifically binds to at least one of a human, a mouse, a rat, and equine CD39 protein. Often, the antibody is conjugated to a fluorophore. In some instances, the antibody is conjugated to a bead. In some cases, at least 20% of the population of SDC2+ stromal stem cells is SDC2+. In some cases, at least 40% of the population of SDC2+ stromal stem cells is SDC2+. In some cases, at least 70% of the population of SDC2+ stromal stem cells is SDC2+. Often, isolating the cells bound to the CD39 binding agent comprises fluorescence activated cell sorting. In some cases, the cells bound to the CD39 binding agent comprises magnetic-activated cell sorting. In some instances, culturing the cells isolated cells. Often, at least 90% of the SDC2+ stromal stem cells are CD45−. In some cases, the composition further comprises a buffer. In some instances, the composition further comprises an extracellular matrix. Often, the extracellular matrix is comprises a collagen. In some cases, the extracellular matrix is comprises a hyaluronic acid. Often, the composition further comprises a cryopreservant comprising DMSO. In some instances, the composition further comprises a cryopreservant comprising glycerol. In some cases, the population of SDC2+ stromal stem cells further comprises CD25+ FoxP3+ regulatory T cells. In some cases, the method comprises genetically modifying the cells to overexpress an apyrase. In some cases, the method comprises genetically modifying the cells to overexpress CD39. In some cases, the method comprises genetically modifying the cells to overexpress CD39L3. In some cases, the method comprises genetically modifying the cells to overexpress CD73.

Also provided herein are methods of isolating an immuno-modulatory composition. Some such methods comprise at least one of: (a) contacting a population of mammalian cells to a CD39 binding agent; (b) isolating the cells bound to the CD39 binding agent; and (c) recovering a supernatant comprising the exosomes from the isolated cells. In some cases, obtaining an exosome fraction from the supernatant. Often, obtaining an exosome fraction comprises centrifuging the supernatant. In some instances, the centrifugation comprises centrifuging the cells at about 100,000 g. In some cases, the centrifugation comprises centrifuging the cells for at least one hour. In some instances, the centrifugation comprises ultrafiltration. In some cases, the centrifugation comprises size-exclusion liquid chromatography. Often, obtaining an exosome fraction comprises ultrafiltration. In some cases, obtaining an exosome fraction comprises size-exclusion liquid chromatography. In some instances, obtaining an exosome fraction comprises contacting the supernatant to an antibody. Often, the antibody is selected from at least one of an anti-CD39 antibody and an anti-SDC2 antibody. In some cases, the exosomes are paracrine signaling exosomes. Often, the isolated cells are SDC2+. In some instances, the isolated cells comprise mesenchymal stem cells. In some cases, at least 90% of the isolated cells are CD45−. In some instances, the method comprises storing the exosome fraction at room temperature. Often, the method comprises storing the exosome fraction without cryogenic preservation. In some cases, the method comprises adding an immunosuppressive drug to the immuno-modulatory composition. Often, the isolated cells are perturbed to elicit exosome production. In some instances, the isolated cells are cultured in a hollow-fiber bioreactor. In some cases, the isolated cells comprise CD25+ FoxP3+ regulatory T cells. In some cases, the method comprises genetically modifying the cells to overexpress an apyrase. In some cases, the method comprises genetically modifying the cells to overexpress CD39. In some cases, the method comprises genetically modifying the cells to overexpress CD39L3. In some cases, the method comprises genetically modifying the cells to overexpress CD73.

Also provided herein are methods of modulating an inflammation response in a mammal. Some such methods comprise delivering a composition comprising SDC2+ cells to a site of the inflammation response, wherein the SDC2+ cells are purified from a mixed population of cells by isolating cells based upon CD39 expression. In some instances, isolating cells comprises collecting cells bound to a CD39 binding agent. Often, isolating the cells comprises culturing the cells bound to the CD39 binding agent. In some cases, delivering comprises injecting the composition comprising SDC2+ cells. Often, delivering comprises topically applying the composition comprising SDC2+ cells. In some cases, the composition comprises a hydrogel. In some instances, the composition comprises a collagen gel. In some cases, delivering comprises intraocularly administering the composition comprising SDC2+ cells. Often, delivering comprises ophthalmic application of the composition comprising SDC2+ cells. In some cases, delivering comprises intravenous delivery the composition comprising SDC2+ cells. In some instances, delivering comprises intra-lymph node injection of the composition comprising SDC2+ cells. In some cases, delivering comprises subcutaneous delivery of the composition comprising SDC2+ cells. Often, delivering comprises intraperitoneal delivery of the composition comprising SDC2+ cells. In some cases, delivering comprises intrathecal delivery of the composition comprising SDC2+ cells. In some instances, the SDC2+ cells wherein the SDC2+ cells are selected from at least one of human, mouse, rat, and equine cells. In some cases, the mixed population of mammalian cells are obtained from a source selected from bone marrow, adipose tissue, skeletal muscle, endometrium, placenta, umbilical cord, Wharton's jelly, and cells derived from pluripotent cells. Often, the CD39 binding agent comprises an antibody. In some cases, the antibody is raised to a CD39 antigen. In some instances, the antibody comprises a variable domain that specifically binds to at least one mammalian CD39 protein. In some cases, the antibody specifically binds to at least one of a human, a mouse, a rat, or equine CD39 protein. In some cases, the antibody is conjugated to a fluorophore. Often, the antibody is conjugated to a bead. Often, at least 20% of the SDC2+ cells are SDC2+. In some cases, at least 40% of the SDC2+ cells are SDC2+. In some instances, at least 70% of the SDC2+ cells are SDC2+. In some cases, isolating the cells comprises fluorescence activated cell sorting. In some cases, isolating the cells comprises magnetic-activated cell sorting. Often, at least 90% of the SDC2+ cells are CD45−. In some cases, the method comprises delivering at least $10^3$ SDC2+ cells. In some cases, the method comprises delivering at least $10^4$ SDC2+ cells. In some cases, the method comprises delivering at least $10^5$ SDC2+ cells. In some cases, the method comprises delivering at least $10^6$ SDC2+ cells. In some cases, the population of SDC2+ stromal stem cells further comprises CD25+ FoxP3+ regulatory T cells. In some cases, the method comprises genetically modifying the cells to overexpress an apyrase. In some cases, the method comprises genetically modifying the cells to overexpress CD39. In some cases, the method comprises genetically modifying the cells to overexpress CD39L3. In some cases, the method comprises genetically modifying the cells to overexpress CD73. Often, the inflammation response comprises at least one of type 1 diabetes, type 2 diabetes, sepsis, Crohn's disease, inflammatory bowel syndrome, rheumatoid arthritis, graft versus host disease, multiple sclerosis, ALS, a dermal wound, a bone fracture, a concussion wound, a burn, atherosclerosis, nephropathy, cardiomyopathy, neuropathy, a kidney disorder, kidney failure, a diabetic ulcer, a leg ulcer, ARDS, sepsis, inflammatory liver disease, myocarditis, post myocardial infarction syndrome, postpericardiotomy syndrome, subacute bacterial endocarditis, antiglomulerular basement membrane nephritis, interstitial cystitis, lupus nephritis, autoimmune hepatitis, primary biliary cirrhosis, primary sclerosing cholangitis, antisynthetase syndrome, asthma, chronic obstructive pulmonary disease, cystic fibrosis, atelectasis, bronchitis, emphysema, pneumonia, pulmonary edema, Alopecia Areata, autoimmune Angioedema, autoimmune progesterone dermatitis, autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosis, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, autoimmune polyendocrine syndrome, autoimmune polyendocrine syndrome type 2, autoimmune polyendocrine syndrome type 3, autoimmune pancreatitis, autoimmune thyroiditis, Ord's thyroiditis, Graves' disease, Reproductive Organ disorder, autoimmune oophoritis, Endometriosis, autoimmune orchitis, Sjogren's syndrome, autoimmune enteropathy, Celiac disease, Microscopic colitis, Ulcerative colitis, Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, Undifferentiated connective tissue disease, cachexia, sarcophenia, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff s encephalitis, Chronic inflammatory demyelinating polyneuropathy, Guillain-Barré syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with Streptococcus, Progressive inflammatory neuropathy, Restless leg syndrome, Stiff person syndrome, Sydenham chorea, amyotrophic lateral sclerosis, Parkinson's disease, Alzheimer's disease, Transverse myelitis, autoimmune retinopathy, autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, autoimmune inner ear disease, Meniere's disease, Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, and Vasculitis.

Also provided herein are methods of modulating an inflammation response in a mammal. Some such methods comprise delivering a composition comprising exosomes to a site of the inflammation response, wherein the exosomes are SDC2+ and the exosomes are from SDC2+ cells isolated from a mixed population of mammalian cells based upon CD39 expression. In some cases, isolating cells comprises collecting cells bound to a CD39 binding agent. In some instances, isolating the cells comprises culturing the cells bound to the CD39 binding agent. Often, delivering comprises injecting the composition comprising exosomes. Sometimes, delivering comprises topically applying the composition comprising exosomes. In some cases, the composition comprises a hydrogel. Often, the composition comprises a collagen gel. In some instances, delivering comprises intraocularly administering the composition comprising exosomes. In some cases, delivering comprises ophthalmic application of the composition comprising exosomes. Sometimes, delivering comprises intravenous delivery the composition comprising exosomes. In some cases, delivering comprises intra-lymph node injection of the composition comprising exosomes. In some cases, delivering comprises subcutaneous delivery of the composition comprising exosomes. In some instances, delivering comprises intraperitoneal delivery of the composition comprising exosomes. In some cases, delivering comprises intrathecal delivery of the composition comprising exosomes. Often, the exosomes are isolated from SDC2+ cells that are at least one of human, mouse, rat, and equine cells. Sometimes, the mixed population of mammalian cells are obtained from a source selected from bone marrow, adipose tissue, skeletal muscle, endometrium, placenta, umbilical cord, Wharton's jelly, and cells derived from pluripotent cells. In some cases, the CD39 binding agent comprises an antibody. In some cases, the antibody is raised to a CD39 antigen. In some instances, the antibody comprises a variable domain that specifically binds to at least one mammalian CD39 protein. Often, the antibody specifically binds to at least one of a human, a mouse, a rat, or equine CD39 protein. In some cases, the antibody is conjugated to a fluorophore. Sometimes, the antibody is conjugated to a bead. In some cases, at least 20% of the exosomes are SDC2+. In some cases, at least 40% of the exosomes are SDC2+. In some cases, at least 70% of the exosomes are SDC2+. Often, isolating the cells comprises fluorescence activated cell sorting. In some cases, isolating the cells comprises magnetic-activated cell sorting. In some instances, the method further comprises culturing the cells bound to the CD39 binding agent. In some cases, the cells are CD45−. In some cases, the method comprises delivering at least $10^6$ exosomes. In some cases, the method comprises delivering at least $10^7$ exosomes. In some cases, the method comprises delivering at least $10^8$ exosomes. In some cases, the method comprises delivering at least $10^9$ exosomes. In some cases, the population of SDC2+ stromal stem cells further comprises CD25+ FoxP3+ regulatory T cells. In some cases, the method comprises genetically modifying the cells to overexpress an apyrase. In some cases, the method comprises genetically modifying the cells to overexpress CD39. In some cases, the method comprises genetically modifying the cells to overexpress CD39L3. In some cases, the method comprises genetically modifying the cells to overexpress CD73. Often, the inflammation response comprises at least one of type 1 diabetes, type 2 diabetes, sepsis, Crohn's disease, inflammatory bowel syndrome, rheumatoid arthritis, graft versus host disease, multiple sclerosis, ALS, a dermal wound, a bone fracture, a concussion wound, a burn, atherosclerosis, nephropathy, cardiomyopathy, neuropathy, a kidney disorder, kidney failure, a diabetic ulcer, a leg ulcer, ARDS, sepsis, inflammatory liver disease, myocarditis, postmyocardial infarction syndrome, postpericardiotomy syndrome, subacute bacterial endocarditis, anti-glomulerular basement membrane nephritis, interstitial cystitis, lupus nephritis, autoimmune hepatitis, primary biliary cirrhosis, primary sclerosing cholangitis, antisynthetase syndrome, asthma, chronic obstructive pulmonary disease, cystic fibrosis, atelectasis, bronchitis, emphysema, pneumonia, pulmonary edema, Alopecia Areata, autoimmune Angioedema, autoimmune progesterone dermatitis, autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, autoimmune polyendocrine syndrome, autoimmune polyendocrine syndrome type 2, autoimmune polyendocrine syndrome type 3, autoimmune pancreatitis, autoimmune thyroiditis, Ord's thyroiditis, Graves' disease, Reproductive Organ disorder, autoimmune oophoritis, Endometriosis, autoimmune orchitis, Sjogren's syndrome, autoimmune enteropathy, Celiac disease, Microscopic colitis, Ulcerative colitis, Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, Undifferentiated connective tissue disease, cachexia, sarcophenia, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff's encephalitis, Chronic inflammatory demyelinating polyneuropathy, Guillain-Barré syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with Streptococcus, Progressive inflammatory neuropathy, Restless leg syndrome, Stiff person syndrome, Sydenham chorea, amyotrophic lateral sclerosis, Parkinson's disease, Alzheimer's disease, Transverse myelitis, autoimmune retinopathy, autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, autoimmune inner ear disease, Meniere's disease, Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, and Vasculitis.

Also provided herein are compositions comprising a population of cells that is at least 20% SDC2+, wherein the population of cells is bound to a CD39 binding agent. In some cases, the population of cells is at least 30% SDC2+. In some cases, the population of cells is at least 40% SDC2+. In some cases, the population of cells is at least 50% SDC2+. In some cases, the population of cells is at least 60% SDC2+. In some cases, the population of cells is at least 70% SDC2+. In some cases, the population of cells is at least 80% SDC2+. In some cases, the population of cells is at least 90% SDC2+. In some cases, the population of cells is at least 95% SDC2+. In some cases, the population of cells is at least 99% SDC2+. In some cases, the population of cells is at least 20% CD39+. In some cases, the population of cells is at least 30% CD39+. In some cases, the population of cells is at least 40% CD39+. In some cases, the population of cells is at least 50% CD39+. In some cases, the population of cells is at least 60% CD39+. In some cases, the population of cells is at least 70% CD39+. In some cases, the population of cells is at least 80% CD39+. In some cases, the population of cells is at least 90% CD39+. In some cases, the population of cells is at least 95% CD39+. In some cases, the population of cells is at least 99% CD39+.

In some cases, at least 90% of the population of cells is CD45−. In some instances, the composition further comprises at least $10^6$ exosomes isolated from a population of cells bound to a CD39 binding agent. In some instances, the composition further comprises at least $10^7$ exosomes isolated from a population of cells bound to a CD39 binding agent In some instances, the composition further comprises at least $10^8$ exosomes isolated from a population of cells bound to a CD39 binding agent. In some instances, the composition further comprises at least 1 μg of exosomes isolated from a population of cells bound to a CD39 binding agent. In some instances, the composition further comprises at least 10 μg of exosomes isolated from a population of cells bound to a CD39 binding agent. In some instances, the composition further comprises at least 20 μg of exosomes isolated from a population of cells bound to a CD39 binding agent. In some instances, the composition further comprises at least 50 μg of exosomes isolated from a population of cells bound to a CD39 binding agent. In some instances, the composition further comprises at least 100 μg of exosomes isolated from a population of cells bound to a CD39 binding agent. In some instances, the composition further comprises at least 150 μg of exosomes isolated from a population of cells bound to a CD39 binding agent. In some instances, the composition further comprises at least 200 μg of exosomes isolated from a population of cells bound to a CD39 binding agent. In some instances, the composition further comprises at least 250 μg of exosomes isolated from a population of cells bound to a CD39 binding agent. In some instances, the composition further comprises at least 500 μg of exosomes isolated from a population of cells bound to a CD39 binding agent. In some instances, the composition further comprises at least 750 μg of exosomes isolated from a population of cells bound to a CD39 binding agent. In some instances, the composition further comprises at least 1000 μg of exosomes isolated from a population of cells bound to a CD39 binding agent. In some cases, the CD39 binding agent comprises an antibody. In some cases, the antibody is raised to a CD39 antigen. In some instances, the antibody comprises a variable domain that specifically binds to at least one mammalian CD39 protein. Often, the antibody specifically binds to at least one of a human, a mouse, a rat, or equine CD39 protein. In some cases, the antibody is conjugated to a fluorophore. Sometimes, the antibody is conjugated to a bead. In some instances, the composition further comprises a buffer. In some instances, the composition further comprises a cyropreservant comprising DMSO. In some instances, the composition further comprises a cyropreservant comprising glycerol. In some cases, the composition comprises at least $10^3$ cells. In some cases, the composition comprises at least $10^4$ cells. In some cases, the composition comprises at least $10^5$ cells. In some cases, the composition comprises at least $10^6$ cells. In some cases, the composition comprises at least $10^7$ cells. In some cases, the population of cells comprises CD25+ FoxP3+ regulatory T cells. In some cases, the population of cells is genetically modified to overexpress an apyrase. In some cases, the population of cells is genetically modified to overexpress CD39. In some cases, the population of cells is genetically modified to overexpress CD39L3. In some cases, the population of cells is genetically modified to overexpress CD73.

Also provided herein are compositions comprising exosomes, wherein the exosomes are at least 20% SDC2+ and wherein the exosomes are bound to a CD39 binding agent. In some cases, the exosomes are at least 30% SDC2+. In some cases, the exosomes are at least 40% SDC2+. In some cases, the exosomes are at least 50% SDC2+. In some cases, the exosomes are at least 60% SDC2+. In some cases, the exosomes are at least 70% SDC2+. In some cases, the exosomes are at least 80% SDC2+. In some cases, the exosomes are at least 90% SDC2+. In some cases, the exosomes are at least 95% SDC2+. In some cases, the exosomes are at least 99% SDC2+. In some cases, the exosomes are at least 20% CD39+. In some cases, the exosomes are at least 30% CD39+. In some cases, the exosomes are at least 40% CD39+. In some cases, the exosomes are at least 50% CD39+. In some cases, the exosomes are at least 60% CD39+. In some cases, the exosomes are at least 70% CD39+. In some cases, the exosomes are at least 80% CD39+. In some cases, the exosomes are at least 90% CD39+. In some cases, the exosomes are at least 95% CD39+. In some cases, the exosomes are at least 99% CD39+. In some cases, the population is CD45−. In some instances, the composition comprises at least 10^6 exosomes. In some instances, the composition comprises at least 10^7 exosomes. In some instances, the composition comprises at least 10^8 exosomes. In some instances, the composition comprises at least 1 μg of exosomes. In some instances, the composition comprises at least 10 μg of exosomes. In some instances, the composition comprises at least 20 μg of exosomes. In some instances, the composition comprises at least 50 μg of exosomes. In some instances, the composition comprises at least 100 μg of exosomes. In some instances, the composition comprises at least 150 μg of exosomes. In some instances, the composition comprises at least 200 μg of exosomes. In some instances, the composition comprises at least 250 μg of exosomes. In some instances, the composition comprises at least 500 μg of exosomes. In some instances, the composition comprises at least 750 μg of exosomes. In some instances, the composition comprises at least 1000 μg of exosomes. In some instances, the composition comprises a buffer. In some cases, the CD39 binding agent comprises an antibody. In some cases, the antibody is raised to a CD39 antigen. In some instances, the antibody comprises a variable domain that specifically binds to at least one mammalian CD39 protein. Often, the antibody specifically binds to at least one of a human, a mouse, a rat, or equine CD39 protein. In some cases, the antibody is conjugated to a fluorophore. Sometimes, the antibody is conjugated to a bead.

BRIEF DESCRIPTION OF THE DRAWINGS

The novel features of the invention are set forth with particularity in the specification and appended claims. Further understanding of the features and advantages of the present invention will be obtained by reference to the following detailed description that sets forth illustrative embodiments, in which the principles of the invention are utilized, and the accompanying drawings of which:

FIG. 2A shows a representative gating control and identification of CD39+/CD362+ cells from bone marrow (highlighted by bold square).

FIG. 2B shows relative population percentage of CD39+/CD362+ cells versus CD39hi/CD362+ cells.

FIG. 2C shows tabular results of colony formation assay for unsorted cells, CD39−/CD362+ cells, CD39+/CD362+ cells, CD39+/CD362− cells, and double negative cells.

DETAILED DESCRIPTION OF THE INVENTION

Figure 1A:
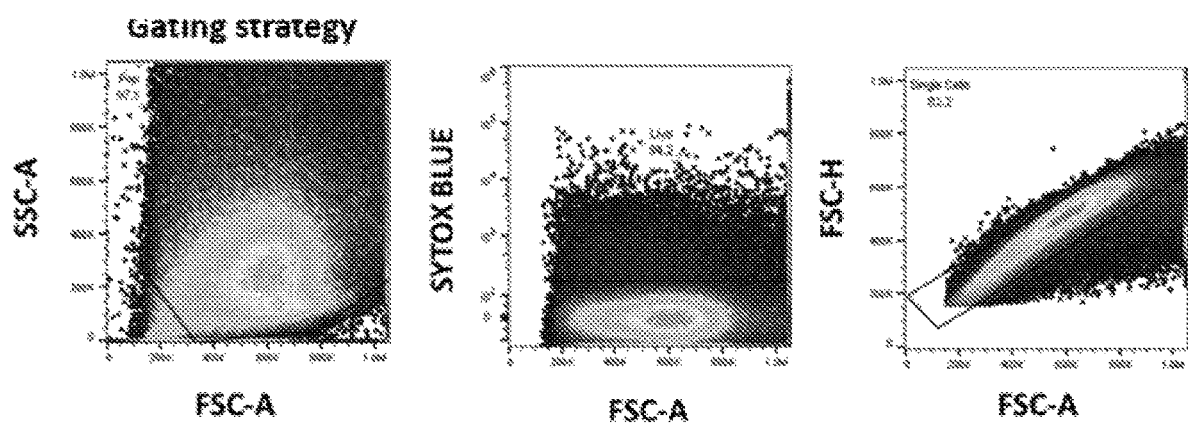
FIG. 1A shows an exemplary gating strategy for isolating stromal stem cells from umbilical cord.

Stromal stem cells or mesenchymal stromal cells have shown therapeutic value, for example, in their ability to migrate to the site of tissue injury and relative ease of in vitro expansion. In particular SDC2+ stromal stem cells have shown efficacy in treatment of a wide range of diseases. Alternative methods of preparing SDC2+ stromal stem cells are disclosed herein, wherein isolation of SDC2+ stromal stem cells is based on expression of CD39.

CD39 and CD39L3 are apyrase enzymes. Apyrase enzymes cleave phosphate groups from ATP and ADP to yield AMP and phosphate. More generally speaking, apyrase enzymes are extracellular nucleosidases, which mediate catabolism of extracellular nucleotides, such as ATP and ADP. CD39 and CD39L3 cell surface expression often correlates with SDC2+ cell surface expression, such that CD39 or CD39L3 is effective as a marker cell surface protein for isolation of SDC2+ stromal stem cells. Extracellular nucleosideases, in some cases, mediate catabolism of extracellular ATP and ADP to AMP, which is further degraded to adenosine. CD73 often degrades AMP to adenosine. Additional examples of extracellular nucleosidases include CD39L1, CD39L2, and CD39L4. As ATP and ADP act antagonistically to free adenosine outside of the cell to mediate a number of responses including cell differentiation and inflammation, CD39, CD39 homologues, and even structurally diverse, functionally analogous enzymes may have a common impact on extracellular ATP signaling.

In some cases, apyrases, such as extracellular nucleosidases, are attached to a cell via a transmembrane domain. In some cases, extracellular nucleosidases are soluble proteins outside the cell. Apyrase activity is effected through full length proteins or, alternately, through proteins having an apyrase extracellular domain or an extracellular domain sharing sequence, structural similarity or functional similarity to an apyrase, so as to commonly modulate ATP or ADP concentration relative to adenosine or extracellular purine concentration.

SDC2+ and SDC2+CD39+ stromal stem cell and SDC2+ and SDC2+CD39+ exosome compositions and methods of isolation based on CD39 expression and uses for such cells in modulation the inflammatory response are disclosed herein. In some cases these compositions mediate of paracrine signaling or deliver paracrine signaling components.

Additional uses for SDC2+ and SDC2+CD39 stromal stem cell and SDC2+ and SDC2+CD39+ exosome compositions include compositions that include anti-inflammatory therapeutics formulated with the exosomes. This feature would allow a therapeutic to be delivered to an individual who needs treatment. For example, an anti-TNF antibody, such as infliximab, could be formulated with the SDC2+ and SDC2+CD39+ stromal stem cell and SDC2+ and SDC2+ CD39+ exosome compositions. Alternately or on combination a native signaling component, such as a paracrine signaling component, is contained in some SDC2+ and SDC2+CD39+ stromal stem cell and SDC2+ and SDC2+ CD39+ exosome compositions.

In addition, SDC2+ and SDC2+CD39+ stromal stem cell and SDC2+ and SDC2+CD39+ exosome compositions, such as those described herein, can also be combined with regulatory T cells, such as CD4+CD25+FOXP3+ regulatory T cells, to create therapeutics that treat inflammatory or immune diseases. The exosome compositions, in this case, would enhance the activity, potency and longevity of a regulatory T cell therapeutic.

Methods of Isolation of SDC2+ Stromal Stem Cells Using CD39 Binding Agents

SDC2+ stromal stem cells disclosed herein are isolated or purified based on expression of CD39. In some cases, such methods isolate SDC2+ stromal stem cells using a CD39 binding agent. The method of isolation or purification involves isolating stromal stem cells from a population of mammalian cells. In some cases, methods of isolation or purification of SDC2+ stromal stem cell compositions comprise obtaining a population of mammalian cells for isolation of the SDC2+ stromal stem cells, contacting the population of mammalian cells with a CD39 binding agent, recovering cells bound to the CD39 binding agent, and thereby obtaining SDC2+ stromal stem cells. The method of isolation or purification results in a stromal stem cell composition enriched for SDC2+ cells. Some such cell populations comprise SDC2+ stromal stem cells, wherein at least 20% of the stromal stem cells comprise express SDC2+. In some cases, the CD39 binding agent comprises an antibody or an antibody fragment. In some cases, the antibody is raised to a CD39 antigen. In some instances, the antibody comprises a variable domain that specifically binds to at least one mammalian CD39 protein. Often, the antibody specifically binds to at least one of a human, a mouse, a rat, or equine CD39 protein. In some cases, the antibody is conjugated to a fluorophore. Sometimes, the antibody is conjugated to a bead.

Isolation or purification of SDC2+ stromal stem cells is accomplished with the use of a CD39 binding agent. In some cases, the CD39 binding agent comprises one or more antibodies to CD39 or fragments thereof. Some methods of isolation or purification comprise incubating a population of mammalian cells with a CD39 binding agent and retaining only the cells bound to the CD39 binding agent. CD39 binding agents, such as CD39 antibodies suitable for methods disclosed herein have the property of binding specifically to CD39. Incubation of a population of mammalian cells with the CD39 binding agent is done in a buffer that promotes specific binding of the CD39 binding agent to CD39 and at a temperature that facilitates antibody binding and cell viability and stability. In some cases, the incubation is done at room temperature. In some cases, the incubation is done at 4° C. An incubation buffer often comprises at least one or a buffer, a detergent, and a salt. Alternately or in combination, the CD39 binding agent comprises a binding agent that is not an antibody, such as a CD39 receptor or an oligomer that binds CD39. Isolated or purified SDC2+ stromal stem cells are often prepared in a buffer or excipient suitable for storage or for administration to an individual in need thereof.

Stromal cells for methods of isolation or purification of SDC2+ stromal stem cells, in some cases, are modified to increase CD39, CD39L3, or other apyrase protein expression. It is observed that such overexpression improves the therapeutic efficacy of the stromal stem cells resulting from the isolation or purification method. In some cases, cells are genetically modified to overexpress CD39. In some cases, cells are genetically modified to overexpress CD39L3. Alternately, overexpression of an apyrase, apyrase functional fragment, apyrase extracellular domain, or extracellular domain functional fragment, or protein having an apyrase extracellular domain activity, is sufficient to effect improved therapeutic efficacy.

Genetic modification of stromal cells is accomplished by methods including but not limited to transfection of the stromal cells with one or more plasmids that comprise the CD39 or CD39L3 coding sequence and a promoter, such as a CMV, SV40, EF1a, or CAG promoter. Genetic modification of stromal cells, in some cases, is accomplished by infection of the stromal cells with a virus that comprises the CD39 or CD39L3 coding sequence and a promoter.

Methods of isolation or purification of SDC2+ stromal stem cells using a CD39 binding agent yield compositions comprising a specific proportion of SDC2+ stromal stem cells. In some cases, the proportion of stromal stem cells in the composition purified using a CD39 binding agent that comprise SDC2 is within a range of 20% to 99%. Some methods of isolation or purification result in a stromal stem cell composition where the proportion of stromal stem cells in the composition that comprise SDC2 is at least 20%, at least 30%, at least 40%, at least 50%, at least 60%, at least 70%, at least 80%, at least 90%, at least 95%, at least 99%, or greater than 99%. In some cases, method of isolation or purification results in a stromal stem cell composition where the proportion of stromal stem cells in the composition that comprise CD39 is at least 20%, at least 30%, at least 40%, at least 50%, at least 60%, at least 70%, at least 80%, at least 90%, at least 95%, at least 99%, or greater than 99%.

Methods of isolation or purification of cells binding to a CD39 binding agent, such as isolation or purification of SDC2+ stromal stem cells using a CD39 binding agent such as an antibody or CD39 conjugate, in some cases, yield compositions comprising SDC2+ cells and further comprising regulatory T cells. In some cases, the regulatory T cells are CD25+. In some cases, the regulatory T cells are FoxP3+. In some cases, the regulatory T cells are CD25+ and FoxP3+.

Disclosed herein are methods of isolation or purification of SDC2+ stromal stem cells binding to a CD39 binding agent in a therapeutically effective amount. A minimum therapeutically effective amount of SDC2+ stromal stem cells purified using a CD39 binding agent, in some cases, ranges from $10^3$-$10^8$ cells, for example, $10^3$, $10^4$, $10^5$, $10^6$, $10^7$, $10^8$, or more than $10^8$ cells. Sometimes substantially fewer or substantially more cells constitute a therapeutic amount. Isolation or purification of SDC2+ stromal stem cells via CD39 binding agents, in some cases, comprises concentrating the SDC2+ stromal stem cell composition to be diluted in a buffer or excipient by the individual prior to administration. In some cases, isolation or purification of SDC2+ stromal stem cell compositions binding to a CD39 binding agent comprises diluting the SDC2+ stromal stem cell composition in a buffer or excipient so as to make it ready to be administered to the individual. In some cases, methods of isolation or purification of SDC2+ stromal stem cell compositions binding to a CD39 binding agent results in single use vials or IV bags. In some cases, methods of isolation or purification of SDC2+ stromal stem cell compositions using CD39 binding agents results in multiple doses are present in a single container.

Methods of isolation or purification of SDC2+ stromal stem cells using a binding agent such as an anti-CD39 antibody comprises isolating the CD39 antibody-SDC2+ stromal stem cell complex from the population of mammalian cells. CD39 antibody-SDC2+ stromal stem cell complexes are purified any number of suitable methods including but not limited to fluorescence activated cell sorting (FACS), immunoprecipitation, column purification using protein A beads, column purification using protein G beads, column purification using biotinylated beads and a biotinylated secondary antibody, and magnetic bead based separation methods. SDC2+ stromal stem cells are then eluted from the antibody using a buffered salt solution having stringency sufficient to elute the SDC2+ stromal stem cells from the antibody. Buffered salt solutions are removed from the exosome composition using a centrifugation or dilution procedure. The resulting isolated, purified SDC2+ stromal stem cells are then diluted in a physiologically acceptable buffer or excipient and frozen or otherwise stored at a temperature where the SDC2+ stromal stem cells with retain potency and stability. Optionally, the SDC2+ stromal stem cells are cultured in a mammalian cell culture buffer to expand the cell number before preparing the cells for administration.

Methods of Isolation of SDC2+ Exosomes

Disclosed herein are methods of isolating, purifying or enriching for SDC2+ exosomes using CD39 binding agents. Exosome compositions such as paracrine signaling exosome compositions disclosed herein are isolated or purified. The method of isolation or purification involves isolating exosomes from a population of stromal cells such as SDC2+ stromal cells, isolated using a CD39 binding agent by methods provided herein. Methods of isolation or purification of exosome compositions often comprise obtaining a cell population enriched for SDC2+ cells from a mixed population of mammalian cells using a CD39 binding agent for isolation of the exosomes, recovering a supernatant from said cell population, and obtaining an exosome fraction from the supernatant. Exosome compositions, such as paracrine signaling exosome compositions disclosed herein, in some cases, express SDC2. Often, exosome compositions herein express CD39. In some cases, the SDC2 is found in the interior of the exosome. In some cases, the SDC2 is found on the exterior of the exosome. CD39 is alternatively found in the interior of the exosome or on the exterior of the exosome. The method of isolation or purification results in an exosome composition comprising exosomes, wherein at least 20% of the exosomes comprise SDC2.

Stromal cells for methods of isolation or purification of exosome compositions such as paracrine signaling exosome compositions, in some cases, are modified to increase the yield of exosome compositions resulting from the isolation or purification method. In some cases, cells are genetically modified to overexpress SDC2. In some cases, cells are genetically modified to overexpress CD39. Genetic modification of stromal cells is accomplished by methods including but not limited to transfection of the stromal cells with one or more plasmids that comprise the SDC2 or CD39 coding sequence and a promoter, such as a CMV, SV40, EF1a, or CAG promoter. Genetic modification of stromal cells, in some cases, is accomplished by infection of the stromal cells with a virus that comprises the SDC2 or CD39 coding sequence and a promoter.

Stromal cells for methods of isolation or purification of exosome compositions using CD39 binding agents provided herein, such as paracrine signaling exosome compositions, are genetically modified to overexpress a protein associated with controlling the cytoskeleton. In some cases, cells are genetically modified to overexpress cortactin. Genetic modification of stromal cells is accomplished by methods including but not limited to transfection of the stromal cells with one or more plasmids that comprise the cortactin coding sequence and a promoter, such as a CMV, SV40, EF1a, or CAG promoter. Genetic modification of stromal cells, in some cases, is accomplished by infection of the stromal cells with a virus that comprises the cortactin coding sequence and a promoter.

Often, stromal cells for methods of isolation or purification of exosome compositions using CD39 binding agents such as paracrine signaling exosome compositions are irradiated to increase the yield of exosome compositions resulting from the isolation of purification method. Irradiation of cells includes but is not limited to exposing the stromal cells to a source of radiation, such as an alpha radiation source, a beta radiation source, or a gamma radiation source. In some cases, stromal cells are irradiated using gamma-irradiation.

Alternatively or in combination, stromal cells for methods of isolation or purification of exosome compositions using CD39 binding agents such as paracrine signaling exosome composition are subjected to an inflammatory stimulus. Inflammatory stimuli include but are not limited to TNF-alpha, interferon-gamma, interferon-beta, interleukin-1b, TLR agonists, Poly I:C, and LPS.

Additionally, stromal cells for methods of isolation or purification of exosome compositions using CD39 binding agents are subjected to a growth arrest. Growth arrest is understood by those of skill in the art as slowing or stopping division of cells. Methods of growth arrest include but are not limited to irradiation, mitomycin-c, TGFb stimulation, and growing cells to confluence.

Methods of isolation or purification of exosome compositions using CD39 binding agents, such as paracrine signaling exosome compositions yield compositions comprising a specific proportion of exosomes that comprise SDC2. In some cases, the proportion of exosomes in the composition that comprise SDC2 is within a range of 20% to 99%. In some cases, method of isolation or purification results in an exosome composition where the proportion of exosomes in the composition that comprise SDC2 is at least 20%, 30%, 40%, 50%, 60%, 70%, 80%, 90%, 95%, 99%, or greater. In some cases, the proportion of exosomes in the composition that comprise CD39 is within a range of 20% to 99%. In some cases, method of isolation or purification results in an exosome composition where the proportion of exosomes in the composition that comprise CD39 is at least 20%, 30%, 40%, 50%, 60%, 70%, 80%, 90%, 95%, 99%, or greater.

Some methods of isolation or purification of exosome compositions using CD39 binding agents, such as paracrine signaling exosome compositions use continuous production technology, such as hollow-fiber bioreactor technology. Hollow-fiber bioreactors (HFBRs) have high surface-to-volume ratios which support large numbers of cells at high densities. Exemplary HFBRs include but are not limited to FiberCell Systems and Terumo Quantum Cell Expansion System. Such systems can support from about $10^7$ cells to about $10^8$ cells, although cell amounts outside this range may also be employed in some cases. Advantages of HFBRs include but are not limited to a fiber with a molecular weight cutoff of 5-20 kDa which allows nutrients and waste products to pass through but exosomes are retained in the reactor and concentrated up to 100 times. Cells bound to the support do not require splitting as cell lines can grow to post-confluence without significant apoptosis. In some cases, collection of exosomes is maintained over several months of continuous production. All of these factors combine to allow exosomes to be secreted in large numbers and concentrated significantly in the small volume of the extracapillary space of the cartridge. Exosomes cannot cross the fiber in either direction so cell culture serum can be used in the circulating medium without contaminating the secreted exosomes within the extracapillary space of the cartridge.

Methods of isolation or purification of exosome compositions using CD39 binding agents, such as paracrine signaling exosome compositions result in an exosome composition that is free of living cells, in other words, the resulting exosome composition does not comprise a living cell. Isolation or purification of exosome compositions results in a composition that is non-tumorigenic. That is, the exosome composition obtained by methods of isolation or purification disclosed herein does not cause tumors or cancer to develop in a mammal that has been treated with or given one or more doses of the exosome composition.

Methods of isolation or purification using CD39 binding agents result disclosed herein result in a stable composition. For example, the exosome composition such as paracrine signaling exosome composition obtained by the methods of isolation or purification is stable at room temperature (20 to 25° C.), at cold temperatures (3 to 5° C.), or freezing temperatures (−150 to 0° C.). In some cases, stability is improved by the addition of suitable buffers or excipients. Non-limiting examples of excipients include sucrose, trehalose, polyethylene glycol, a polysaccharide, a carrier protein, an inert protein, dextran, hydroxyl ethyl starch (BETA), PEG-4000, gelatin, PLGA, Eudragit RS 100 Nanoparticles, and combinations thereof.

Methods of isolation or purification of exosome compositions using CD39 binding agents disclosed herein result in an exosome composition that can retain potency or activity after being frozen or cryopreserved without the use of a cryoprotectant. Cryoprotectants include DMSO, glycerol, polyethylene glycol, propylene glycol, glycerine, polyvinylpyrolidone, sorbitol, dextran, and trehalose. The exosome compositions also retain potency after being frozen without using special freezing protocols. Special freezing protocols include flash freezing, programmable rate freezer, and freezing in an insulated container. The exosome compositions are frozen in buffer or culture media. Buffers include physiologically acceptable buffers such as phosphate buffer, histidine buffer, citrate buffer, acetate buffer, and other suitable buffers. In some cases exosome compositions disclosed herein are lyophilized.

Methods of isolation or purification of exosome compositions using CD39 binding agents such as paracrine signaling exosome compositions disclosed herein include combining compositions comprising exosomes, for example in vitro exosomes, and SDC2+ mesenchymal stem cells (e.g., SDC2+ mesenchymal stromal stem cells). In some instances, methods of isolation or purification of exosome compositions include combining compositions comprising in vitro exosomes and regulatory T cells. Regulatory T cells include CD25+ regulatory T cells, CD4+ regulatory T cells, FoxP3+ regulatory T cells, CD25+CD4+FoxP3+ regulatory T cells, and combinations thereof. In some instances, methods of isolation or purification of exosome compositions include combining compositions comprising in vitro exosomes, SDC2+ mesenchymal stem cells (e.g., SDC2+ mesenchymal stromal stem cells), and regulatory T cells.

Disclosed herein are methods of isolation or purification of compositions comprising exosomes using CD39 binding agents such as paracrine signaling exosomes in a therapeutically effective amount A therapeutically effective amount of exosomes, in some cases, ranges from $10^6$-$10^8$ exosomes, for example $10^6$, $10^7$, $10^8$, or more exosomes in the composition. In some cases, a therapeutically effective amount of exosomes ranges from 1 µg to 700 mg of exosomes, for example 1 µg, 10 µg, 20 µg, 50 µg, 100 µg, 150 µg, 200 µg, 250 µg, 500 µg, 750 µg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Isolation or purification of exosome compositions, in some cases, comprises concentrating the exosome composition to be diluted by the individual prior to administration. In some cases, isolation or purification of exosome compositions comprises diluting the exosome composition making it ready to be administered by the individual. In some cases, methods of isolation or purification of exosome compositions results in single use vials or syringes. In some cases, methods of isolation or purification of exosome compositions results in multiple doses are present in a single container.

Isolation or purification of exosome compositions such as paracrine signaling exosome compositions using CD39 binding agent, in some cases, is accomplished with the addition of antibodies to SDC2, which has the effect of increasing the yield of exosomes and increasing the proportion of isolated exosomes that comprise SDC2. Methods of isolation or purification comprise incubating a composition comprising exosomes with an anti-CD39 antibody and an anti-SDC2 antibody and retaining only the exosomes bound to the anti-CD39 and the anti-SDC2 antibody. Anti-SDC2 antibodies suitable for methods herein have the property of binding specifically to SDC2. Incubation of a composition comprising exosomes with the anti-SDC2 antibody is done in a buffer suitable for specific binding of the anti-SDC2 antibody to SDC2 and at a temperature that is suitable for antibody binding and exosome stability. In some cases, the incubation is done at room temperature. In some cases, the incubation is done at 4° C. The incubation buffer comprises at least one or a buffer, a detergent, and a salt.

Some compositions comprising exosomes such as paracrine signaling exosomes from which the exosome composition is isolated or purified using CD39 binding agents, in some cases, comprises a cell culture. A cell culture includes but is not limited to SDC2+ cells, mesenchymal stem cells, SDC2+ mesenchymal stem cells, SDC2+ mesenchymal stromal stem cells, CD39+ cells, CD39+ mesenchymal stem cells, CD39+ mesenchymal stromal stem cells, CD39+/SDC2+ cells, and combinations thereof. In some cases, the cell culture is genetically modified to overexpress SDC2 by suitable methods. Methods of isolation or purification of exosome compositions using anti-SDC2 antibodies comprise a method of isolating the SDC2 antibody-exosome complex from the starting material. SDC2 antibody-exosome complexes are purified by methods including but not limited to fluorescence activated cell sorting (FACS), immunoprecipitation, column purification using protein A beads, column purification using protein G beads, column purification using biotinylated beads and a biotinylated secondary antibody, and magnetic bead based separation methods. Exosome compositions are then eluted from the antibody using a buffered salt solution having stringency sufficient to elute the exosome composition from the antibody. Buffered salt solutions are removed from the exosome composition using a desalting column or dilation procedure. The resulting isolated, purified exosome composition is then diluted in a physiologically acceptable buffer or excipient and frozen or otherwise stored at a temperature where the exosome composition with retain potency and stability.

Isolation or purification of exosome compositions such as paracrine signaling exosome compositions, in some cases, is accomplished with the use of antibodies to CD39, which has the effect of increasing the yield of exosomes and increasing the proportion of isolated exosomes that comprise SDC2. Methods of isolation or purification comprise incubating a composition comprising exosomes with an anti-CD39 antibody and retaining only the exosomes bound to the anti-CD39 antibody. Anti-CD39 antibodies have the property of binding specifically to CD39. Incubation of a composition comprising exosomes with the anti-CD39 antibody is done in a buffer that promotes specific binding of the anti-CD39 antibody to CD39 and at a temperature that is optimal for antibody binding and exosome stability. In some cases, the incubation is done at room temperature. In some cases, the incubation is done at 4° C. The incubation buffer comprises at least one or a buffer, a detergent, and a salt.

The composition comprising exosomes such as paracrine signaling exosomes from which the exosome composition is isolated or purified using antibodies to CD39, in some cases, comprises a cell culture. A cell culture includes but is not limited to SDC2+ cells, mesenchymal stem cells, SDC2+ mesenchymal stem cells, SDC2+ mesenchymal stromal stem cells, CD39+ cells, CD39+/SDC2+ cells, and combinations thereof. In some cases, the cell culture is genetically modified to overexpress CD39 by suitable methods. Methods of isolation or purification of exosome compositions using anti-CD39 antibodies comprise a method of isolating the CD39 antibody-exosome complex from the starting material. CD39 antibody-exosome complexes are purified by methods including but not limited to fluorescence activated cell sorting (FACS), immunoprecipitation, column purification using protein A beads, column purification using protein G beads, column purification using biotinylated beads and a biotinylated secondary antibody, and magnetic bead based separation methods. Exosome compositions are then eluted from the antibody using a buffered salt solution having stringency sufficient to elute the exosome composition from the antibody. Buffered salt solutions are removed from the exosome composition using a desalting column or dilation procedure. The resulting isolated, purified exosome composition is then diluted in a physiologically acceptable buffer or excipient and frozen or otherwise stored at a temperature where the exosome composition with retain potency and stability.

Isolation or purification of exosome compositions such as paracrine signaling exosome compositions, in some cases, is accomplished using ultracentrifugation methods, such as preparative ultracentrifugation. Methods of isolation or purification of exosome compositions, comprise obtaining a population of cells such as stromal cells, SDC2+ cells, mesenchymal stem cells, SDC2+ mesenchymal stem cells, SDC2+ mesenchymal stromal stem cells, CD39+ cells, CD39+/SDC2+ cells, and combinations thereof. In some cases, the cells have been genetically altered to overexpress SDC2 and/or CD39. The media or supernatant of the cell culture is isolated or purified from the cell culture. Then, the media or supernatant is mixed with an appropriate salt or buffer to enhance the separation efficacy in ultracentrifugation. The resulting mixture is added to an ultracentrifugation tube which allows the mixture to safely endure high centrifugal forces of about 100,000×g (or 100,000 times the force of gravity) for 1 to 24 hours. Exosome compositions are found concentrated together and removed from the tube. In some cases, the exosomes are removed as a resuspended pellet from the tube. In some cases, the exosomes are visualized in the resulting density gradient and removed by needle aspiration, or other method. The resulting exosome composition is purified from the ultracentrifugation buffer and diluted in a physiologically acceptable buffer or excipient and frozen or otherwise stored at a temperature where the exosome composition with retain potency and stability.

Isolation or purification of exosome compositions such as paracrine signaling exosome compositions, is accomplished in some cases using ultrafiltration. Some ultrafiltration methods are suitable, such as methods involving concentration columns that allow passage of aqueous buffers but not high molecular weight substances, such as exosomes. Some examples of ultrafiltration methods of isolation or purification method comprise obtaining a population of cells such as stromal cells, SDC2+ cells, mesenchymal stem cells, SDC2+ mesenchymal stem cells, SDC2+ mesenchymal stromal stem cells, CD39+ cells, CD39+/SDC2+ cells, or combinations thereof. In some cases, the cells have been genetically altered to overexpress SDC2 and/or CD39 or have been provided with exogenous SDC2 and/or CD39 or a vector encoding SDC2 and/or CD39. The media or supernatant of the cell culture is isolated or purified from the cell culture. Then the media or supernatant is concentrated, such as by a factor of 30, for example 150 ml of starting media or supernatant resulting in 10 ml of concentrated exosomes, using a Stirred Cell Model 8200 with 100,000 kDa Biomax polyethersulfone or Ultracel regenerated cellulose membranes using nitrogen gas at 10 psi. The concentrated exosomes are then transferred to a collection device such as an Amicon Ultra-15 100,000 kDa device and centrifuged, for example in an Allegra X-15R centrifuge at 4,000×g at 4° C., to concentrate the exosomes by another factor of 20, for example 10 ml of concentrated exosomes resulting in a further concentrated 0.5 ml. Alternative columns and centrifuges are substituted in appropriate cases.

In some cases, isolation or purification of exosomes compositions such as paracrine signaling exosome compositions is accomplished using automated systems of manufacturing. In some cases, automated manufacturing is comprises using the Terumo Quantum Cell Expansion System.

Stromal Stem Cell Compositions

Provided herein are compositions, such as compositions comprising SDC2+ stromal stem cells, bound to a CD39 binding agent. Some such compositions comprise SDC2+ CD39+ stromal stem cells or CD39+ stromal stem cells. In some cases, at least 20% of the stromal stem cells in the composition are SDC2+. In some cases, at least 20%, 30%, 40%, 50%, 60%, 70%, 80%, 90%, 95%, 99%, or more of the stromal stem cells are SDC2+. In some cases, at least 20% of the stromal stem cells in the composition are CD39+. In some cases, at least 20%, 30%, 40%, 50%, 60%, 70%, 80%, 90%, 95%, 99%, or more of the stromal stem cells are CD39+. In some cases, at least 20% of the stromal stem cells in the composition are SDC2+CD39+. In some cases, at least 20%, 30%, 40%, 50%, 60%, 70%, 80%, 90%, 95%, 99%, or more of the stromal stem cells are SDC2+CD39+. The proportion of stromal stem cells in the composition comprising SDC2 is determined by immunofluorescence, for example flow cytometry, magnetic activated cell sorting, fluorescence microscopy, or other suitable method.

CD39 binding agents herein, in some cases, comprise antibodies, such as anti-CD39 antibodies or fragments thereof. In some cases, antibodies are raised against a CD39 antigen. In some cases, antibodies comprise a variable domain that specifically binds to at least one mammalian CD39 protein. In some cases, antibodies specifically bind to at least one of a human, a mouse, a rat, or an equine CD39 protein. In some cases, the antibody is conjugated to a fluorophore. In some cases, the antibody is conjugated to a bead.

SDC2 refers to a gene encoding the syndecan-2 protein (also frequently referred to herein and elsewhere in the art as SDC2). Syndecan-2, or 'the SDC2 protein' or simply SDC2, is a transmembrane type I heparin sulfate proteoglycan. Additional synonyms for syndecan-2, aside from 'the SDC2 protein' or SDC2, include HSPG, CD362, HSPG1, and SYND2. Generally, as used herein SDC2 refers to the protein or a recognizable fragment thereof unless otherwise indicated, for example by reciting 'the SDC2 gene,' 'the SDC2 transcript,' 'an SDC2 antibody.' Additionally, SDC2 is identified by its polypeptide sequence in the sequence listing that accompanies this specification.

Stromal cell compositions herein, in some cases, are modified to increase the therapeutic efficacy of the stromal stem cell composition. In some cases, cells are genetically modified to overexpress an apyrase such as CD39 or an alternative apyrase as discussed herein. In some cases, cells are genetically modified to overexpress CD39L3. Genetic modification of stromal cells is accomplished by methods including but not limited to transfection of the stromal cells with one or more plasmids that comprise the CD39 or CD39L3 coding sequence and a promoter, such as a CMV, SV40, EF1a, or CAG promoter. Genetic modification of stromal cells, in some cases, is accomplished by infection of the stromal cells with a virus that comprises the CD39 or CD39L3 coding sequence and a promoter.

SDC2 has three domains: an extracellular domain at amino acids 19-144, a transmembrane domain at amino acids 145-169, and a cytoplasmic domain at amino acids 170-201. SDC2 has been implicated in the mediation of cell binding, cell signaling, and cytoskeletal organization. SDC2 has been demonstrated to be necessary for internalization of HIV-1 TAT protein.

Stromal stem cell compositions disclosed herein, in some cases, comprise a cryoprotectant or cryopreservative. Cryoprotectants include DMSO, glycerol, polyethylene glycol, propylene glycol, glycerine, polyvinylpyrolidone, sorbitol, dextran, trehalose, and commercial formulations such as CryoStor from Biolife solutions. Stromal stem cell compositions herein retain potency after being frozen using special freezing protocols. Special freezing protocols include flash freezing, programmable rate freezer, and freezing in an insulated container. The stromal stem cell compositions are in some cases frozen in buffer or culture media having an added cryoprotectant. Buffers include physiologically acceptable buffers such as phosphate buffer, histidine buffer, citrate buffer, acetate buffer, Hypothermasol from Biolife Solutions and other suitable.

Stromal stem cell compositions disclosed herein are formulated in a physiologically acceptable buffer and in some cases supplemented by at least one excipient. Non-limiting examples of excipients include sucrose, trehalose, polyethylene glycol, a polysaccharide, a carrier protein, an inert protein, dextran, hydroxyl ethyl starch (HETA), PEG-4000, gelatin, PLGA, Eudragit RS 100 Nanoparticles, and combinations thereof. Such stromal stem cell compositions are stored at a temperature determined to be most stable (i.e., wherein the stromal stem cell composition retains highest potency, or retains potency for the longest period of time, or otherwise optimizes a desired trait). In some cases, addition of at least one excipient allows the composition to retain potency, such as paracrine signaling potency, when stored at a higher temperature than otherwise would be possible.

Some stromal stem cell compositions such as CD39+, SDC2+, or SDC2+CD39+ stromal stem cell compositions isolated using apyrase extracellular binding domain agents such as CD39 binding agents disclosed herein, in some cases, comprise SDC2+ stromal stem cells and another mammalian cell. The other mammalian cell combined SDC2+ stromal stem cells are in some cases regulatory T cells, such as CD25+ regulatory T cells, CD4+ regulatory T cells, FoxP3+ regulatory T cells, CD25+CD4+FoxP3+ regulatory T cells, or combinations thereof.

Compositions comprising a wide range of CD39+, SDC2+, or SDC2+CD39+ stromal stem cells are disclosed herein. Some compositions comprise SDC2+ stromal stem cells in a therapeutically effective amount. In some compositions, the amount of SDC2+ stromal stem cells ranges from $10^3$-$10^8$ SDC2+ stromal stem cells, for example $10^3$, $10^4$, $10^5$, $10^6$, $10^7$, or $10^8$ SDC2+ stromal stem cells, or more SDC2+ stromal stem cells in the composition. SDC2+ stromal stem cell compositions, in some cases, are concentrated to be diluted by the individual or the health care provider prior to administration. In some cases, SDC2+ stromal stem cell compositions are diluted and ready to be administered by the individual or health care provider. In some cases, SDC2+ stromal stem cell compositions are contained in single use vials, syringes, or IV bags. In some cases, multiple doses are present in a single container.

A therapeutically active CD39+, SDC2+, or SDC2+ CD39+ stromal stem cell composition disclosed herein, in some cases, comprises an immunosuppressive drug. Immunosuppressive drugs contemplated herein include but are not limited to a glucocorticoid, a cytostatic, an antibody, an immunophilin inhibitor, cyclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. Some SDC2+ stromal stem cell compositions comprise anti-TNF antibodies, including but not limited to infliximab, adalimumab, certolizumab, and golimumab. SDC2+ stromal stem cell compositions comprise TNF inhibitors including but not limited to etanercept, xanthine derivatives, and bupropion. In some cases, SDC2+ stromal stem cell compositions comprise at least one NSAID. In some cases, SDC2+ stromal stem cell compositions comprise at least one steroid.

Exosome Compositions

Provided herein are compositions, such as therapeutically active, compositions comprising exosomes, for example in vitro exosomes, such as SDC2+ exosomes, bound to a CD39 binding agent. In some cases the exosomes comprise components that mediate, effect or inhibit paracrine signaling. In some cases, at least 20% of the exosomes in the composition are SDC2+ or comprise SDC2. In some cases at least 20%, 30%, 40%, 50%, 60%, 70%, 80%, 90%, 95%, 99%, or more of the exosomes comprise SDC2. In some cases at least 20%, 30%, 40%, 50%, 60%, 70%, 80%, 90%, 95%, 99%, or more of the exosomes comprise CD39. SDC2, in some instances is found on the surface of the exosome. In some instances, SDC2 is found at the interior of the exosome. The proportion of exosomes in the composition comprising SDC2 is determined by immunofluorescence, for example flow cytometry, electron microscopy, or other suitable method.

CD39 binding agents herein, in some cases, comprise antibodies, such as anti-CD39 antibodies. In some cases, antibodies are raised against a CD39 antigen. In some cases, antibodies comprise a variable domain that specifically binds to at least one mammalian CD39 protein. In some cases, antibodies specifically bind to at least one of a human, a mouse, a rat, or an equine CD39 protein. In some cases, the antibody is conjugated to a fluorophore. In some cases, the antibody is conjugated to a bead.

SDC2 refers to a gene encoding the syndecan-2 protein (also frequently referred to herein and elsewhere in the art as SDC2). Syndecan-2, or 'the SDC2 protein' or simply SDC2, is a transmembrane type I heparin sulfate proteoglycan. Additional synonyms for syndecan-2, aside from 'the SDC2 protein' or SDC2, include HSPG, CD362, HSPG1, and SYND2. Generally, as used herein SDC2 refers to the protein or a recognizable fragment thereof unless otherwise indicated, for example by reciting 'the SDC2 gene,' 'the SDC2 transcript,' 'an SDC2 antibody.' Additionally, SDC2 is identified by its polypeptide sequence in the sequence listing that accompanies this specification.

SDC2 has three domains: an extracellular domain at amino acids 19-144, a transmembrane domain at amino acids 145-169, and a cytoplasmic domain at amino acids 170-201. SDC2 has been implicated in the mediation of cell binding, cell signaling, and cytoskeletal organization. SDC2 has been demonstrated to be necessary for internalization of HIV-1 TAT protein.

While exosome compositions described herein, in some cases, are derived from cells, the exosome compositions do not necessarily comprise living cells. Cell-free exosome compositions, therefore, are non-tumorigenic, that is, they do not increase the susceptibility of a subject to developing a tumor or cancer, because they do not comprise cells capable of differentiating into tumor cells. In alternative compositions, the exosomes are supplemented with cells, such as mesenchymal stromal cells, that contribute to anti-inflammatory activity or paracrine signaling activity of the compositions.

Exosome compositions disclosed herein retain potency or activity, such as paracrine signaling activity, after being frozen or cryopreserved, often without the use of a cryoprotectant. Cryoprotectants include DMSO, glycerol, polyethylene glycol, propylene glycol, glycerine, polyvinylpyrolidone, sorbitol, dextran, trehalose, and commercial formulations such as CryoStor from Biolife solutions. The exosome compositions also retain potency after being frozen without using special freezing protocols. Special freezing protocols include flash freezing, programmable rate freezer, and freezing in an insulated container. A benefit of the durability of the exosome compositions is that they are more easily frozen and are frozen without cryoprotectants, resulting in compositions that are more durable, more easily and cheaply made, and less likely to suffer from batch variation resulting from loss of activity due to a defect in freezing protocol or composition. The exosome compositions are in some cases frozen in buffer or culture media. Buffers include physiologically acceptable buffers such as phosphate buffer, histidine buffer, citrate buffer, acetate buffer, Hypothermasol from Biolife Solutions and other suitable buffers. In some cases exosome compositions disclosed herein are lyophilized.

Exosome compositions disclosed herein are formulated in a physiologically acceptable buffer and in some cases supplemented by at least one excipient. Non-limiting examples of excipients include sucrose, trehalose, polyethylene glycol, a polysaccharide, a carrier protein, an inert protein, dextran, hydroxyl ethyl starch (HETA), PEG-4000, gelatin, PLGA, Eudragit RS 100 Nanoparticles, and combinations thereof. Such exosome compositions are stored at a temperature determined to be most stable (i.e., wherein the exosome composition retains highest potency, or retains potency for the longest period of time, or otherwise optimizes a desired trait). In some cases, addition of at least one excipient allows the composition to retain potency, such as paracrine signaling potency, when stored at a higher temperature than otherwise would be possible.

Some exosome compositions such as paracrine signaling exosome compositions disclosed herein, in some cases, comprise in vitro exosomes and SDC2+ mesenchymal stem cells (e.g., mesenchymal stromal stem cells isolated based upon expression of CD39). The cells combined to in vitro exosomes are in some cases regulatory T cells, such as CD25+ regulatory T cells, CD4+ regulatory T cells, FoxP3+ regulatory T cells, CD25+CD4+FoxP3+ regulatory T cells, or combinations thereof. In some instances, exosome compositions comprise in vitro exosomes, SDC2+ mesenchymal stem cells (e.g., SDC2+ mesenchymal stromal stem cells isolated based upon expression of CD39), and regulatory T cells (e.g., regulatory T cells isolated based upon expression of CD39).

Compositions comprising a wide range of exosomes are disclosed herein. Some compositions comprise exosomes in a therapeutically effective amount. In some compositions, the amount of exosomes ranges from $10^6$-$10^8$ exosomes, for example $10^6$, $10^7$, $10^8$, or more exosomes in the composition. In some cases, a therapeutically effective amount of exosomes ranges from 1 μg to 700 mg of exosomes, for example 1 μg, 10 μg, 20 μg, 50 μg, 100 μg, 150 μg, 200 μg, 250 μg, 500 μg, 750 μg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Exosome compositions, in some cases, are concentrated to be diluted by the individual prior to administration. In some cases, exosome compositions are diluted and ready to be administered by the individual. In some cases, exosome compositions are contained in single use vials or syringes. In some cases, multiple doses are present in a single container.

Some exosome compositions disclosed herein comprise additional proteins, such as proteins that contribute to therapeutic efficacy, or that mediate paracrine signaling to effect therapeutic efficacy. Proteins include but in some cases are not limited to IL-12, suppressor of cytokine signaling (SOCS), p53, PTEN, CD52, TSC1, FOXP3, Soluble Immune Response Suppressor (SIRS), TGFB, CD39L3, CD73, and Maspin. In some cases, exosomes comprise at least one of protein selected from the list consisting of UBA6, ESYT2, SSCSD, STMN1, STMN2, PRNP, VEGFA, ADD1, NBL1, MINOS1-NBL1, XIRP2, VPS37C, MARS, BST1, MAP1LC3B, MAP1LC3B2, RPSA, RPSAP58, BPNT1, ABI1, SEPT8, NUDT5, WBP2, SPTAN1, ATP1B1, DYNLT3, YIF1A, SEC61A2, SEC61A1, DOCK11, NDE1, NDEL1, UFD1L, SNX1, KIAA1217, CNIH4, CRYZL1, PRAMEF26, PRAMEF11, PRAMEF6, PRAMEF5, PRAMEF23, PRAMEF9, PRAMEF4, ANXA6, CD9, AMOT, PPP2R4, SELENBP1, PSMD4, PIP5K1A, PIPSL, MLLT4, GSK3A, RTN1, MPP1, DSCR3, SUMO2, SUMO3, SUMO4, PPP5C, AIMP2, TUBA4A, RPL23A, CASP3, FAM171A2, KIAA1324L, RAB34, C2orf74, DRG2, MBP, PTTG1IP, MBOAT7, CSNK1E, CSNK1D, EIF3L, EIF3D, UBE2I, CPNE1, APOC3, ARCN1, XRCC6, PSMD10, CROCC, NRD1, TSPAN2, MTOR, DYNLRB1, DYNLRB2, PEA15, POSTN, ARHGEF7, LPHN2, SEPT6, CD58, LGALS8, CD55, C1orf123, EPS15, MUC1, PSAP, GME, TXNRD1, HMGB1, HMGB1P1, RUVBL2, SLC29A1, EIF3S3, EIF3H, EIF3F, METRNL, CA12, PLTP, FNTA, SNRPN, SNRPB, HARS, AP1G1, CDIPT, CNN2, LARS, EIF2A, NAPG, CNN3, IDH2, ULK3, RPS6KA3, NPLOC4, CANX, EIF2B1, PIP4K2A, MYRF, TMEM165, EPN3, TARDBP, RAB5A, SNRPD3, SNX6, CS, LPAR1, AKR1C1, AKR1C2, AKR1C3, SACM1L, CARS, CHURC1-FNTB, FNTB, PCBP2, PCBP3, STAT2, NQO1, MAT2A, STRAP, IL6, SERPINB1, ABHD14A, ABHD14A-ACY1, ACY1, PTGES3, PGD, NPC2, HIST1H2BN, HIST1H2BL, HIST1H2BM, HIST1H2BH, HIST2H2BF, HIST1H2BC, HIST1H2BD, H2BFS, HIST1H2BK, HIST2H2BE, HIST1H2BB, HIST1H2BO, HIST1H2BJ, STK24, PLOD1, ELMO2, ZDHHC20, FAM98A, ANXA7, SLC2A5, PLSCR1, RASA1, DKFZp434N071, SLC9A1, MTAP, TMBIM1, SERINC3, AHSA1, QARS, ARL1, DNAJB1, NMT2, NMT1, FXR1, HNRNPC, RALYL, HNRNPCL1, TGFBR1, ME1, COPB2, TKT, RALB, DBF4B, LRCH3, PNPO, RBM4B, MST4, SERPING1, GALK1, PBXIP1, AQP1, SRSF3, FARSA, EML4, PPP1R7, STEAP2, GUCD1, PDIA6, SIRT2, QPCT, TSPAN9, RAN, EIF3C, EIF3CL, SEPT10, CAP2, NTM, HBS1L, RCN1, ATP6V1A, RNF14, SLC26A4, PTPRA, ATP6V0A1, MFSD8, TOM1L2, SGCE, CYTH3, TSPAN5, EXOC4, PPP6C, ALAD, PFKM, ISYNA1, PCYOX1, ATP6AP2, CAST, RPN1, INPP5K, SLC6A9, LPXN, AKT1, RRAS2, DECR1, SH3KBP1, NUBP2, PMM2, SCFD1, ACP2, PITPNB, GYS1, USP7, GPRC5B, RAB1A, EMB, EBF2, PCMT1, NAP1L1, SH3PXD2A, CCT4, GALK2, DLST, SH3GLB2, SCARB1, CCDC122, HSPE1, PPIL3, PTMA, TAX1BP1, EVA1A, FAM126A, TCEB2, IGLL5, DNPEP, DIAPH1, DISC1, TSNAX, DCUN1D1, PFN2, SRI, CNTLN, EEF1E1, EEF1E1-BLOC1S5, PTPN12, EIF4G1, TMEM248, TPST1, CPA4, MID1, CXCL8, RPL37A, KIAA0319L, IGF1R, TMEM98, PFN2, TNPO3, ATP6V1E1, RARRES2, ITGB6, APPL1, IFT57, TFPI, PSPH, QPRT, MEST, LTBP1, PRPSAP2, MTMR2, GPS1, CYCS, ITM2C, TYMP, APEH, OXSR1, PPM1B, TFG, ARVCF, STARD3NL, KIAA0195, MTPN, DGKA, MASP1, FARP1, FAM3C, DDX17, RPL24, UBA5, SEC14L2, SEC14L3, TIA1, TIAL1, BTN3A3, BTN3A2, BTN3A1, CD63, LEPROTL1, TENC1, ARMC9, EPHA5, EPHA3, TMEM106B, RPL35A, TMEM50B, ALB, EIF4G2, GNPDA1, GNPDA2, CAMK2D, CAMK2B, CAMK2A, GPM6A, ABCE1, CLDND1, MFSD10, RPL9, NECAP2, CTBP1, CTBP2, SPON2, SNF8, DCTD, RELL1, LMAN2, EIF4E, TTC37, IGJ, ALG13, RPS23, SRP72, CALCOCO2, PAIP1, RNASET2, SEPT11, SEC31A, MCC, CXCL6, CXCL5, HAPLN1, CD14, COL12A1, CLTB, ELOVL5, EIF3E, LYPLA1, PFDN1, TCEB1, SORBS3, ERLIN2, ERLIN1, ENY2, RPL30, PLAA, FABP4, TBCA, MAT2B, SKP1, COPSE, SQSTM1, AP3D1, BLMH, RAI14, MAP4K4, FES, FER, SEC24C, ABI2, RPL14, CD44, SEPT7, PTPRM, GLB1, SLC43A3, EIF4A2, PABPC1, PABPC4, PAPSS2, ATP2C1, TNS1, TNS3, THBS4, HEPH, PSEN1, XPO7, PLAU, ITGA2, STX3, PPP3CA, RPS24, PLOD2, MARK2, MARK1, MARK3, GPX8, BZW2, GDI2, CSNK2A1, CSNK2A3, DKK3, CDK14, CDK4, CDK3, CDK1, CDK16, CDK12, CDK15, CDK9, CDK18, CDK13, SF3A3, ASB2, CAPN5, CYFIP2, KLC1, MYO6, IQGAP2, ADAM23, HYI, TRIO, MGLL, DCTN1, NIF3L1, PI4K2A, NACA, GPR84, MGRN1, PACS2, RBBP7, RBBP4, NLN, COL6A3, HNRNPH1, MDH2, PTPRD, PTPRS, MYO1B, PHLDB2, SRP9, ATP11A, PPIE, DIP2A, EPB41, DTNB, TNS1, RND3, PPP2R5D, MANBA, AP2M1, APP, AAK1, C1QTNF3-AMACR, C1QTNF3, TSN, KIDINS220, DPM1, GSTM2, PLSCR4, EPB41L2, PRKCDBP, MUC15, PDE8A, THY1, TCP11L1, RPL27A, CRYAB, AAMDC, TMEM126B, EEF1D, SCYL1, PPP6R3, PRMT1, DCAF5, NUCB2, TSTA3, RPL8, HYOU1, RAB1B, NPEPPS, MDK, VKORC1, AASDHPPT, RNF141, TYK2, USP47, WLS, PSMC3, TSPAN4, STT3A, CD59, LRP8, RAE1, MVB12A, IFITM2, IFITM3, IFITM1, MAPK3, PFDN4, IFT46, EFEMP2, NSFL1C, FRYL, ARRDC1, PITPNA, CCT2, ADA, PCDH7, KRT17, SMAD5, TMED2, MPI, ITFG1, METAP1, RPTOR, HN1, GALNT1, COPS7A, KPNA6, KPNA5, KPNA1, OTUB1, ATP6V0D1, PXN, MACF1, SLC3A2, PPP3CB, GLTP, FERMT3, FBLN2, SEMA3C, CALD1, DCTN2, UACA, TENM2, MTHFD1, CBS, EIF3A, HMBS, SEC23A, PPP2R1A, TSG101, AP3S1, TMX3, VPS26A, VPS37B, SUGT1, SLC8A1, STK4, LSAMP, CDC42BPA, B2M, ATL3, TBC1D9B, FARSB, CDK17, VDAC3, CYB561, MFGE8, FZD6, BCAR1, TNIK, RPS10, RPS10-NUDT3, ST13, ST13P4, ST13P5, RBM38, PIP4K2C, CAD, PRKAG1, TMBIM6, DDX39B, DDX39A, DDX39, hCG_2005638, C12orf75, OCC1, C12orf10, CSRP2, COPZ1, SCYL2, PLXNA1, IGFL2, PTPRB, CHMP1A, RPL18, SLC25A3, SLC38A1, VPS29, PPP1CC, KIAA1033, KRT18, CTDSP2, FMNL3, PDE6H, MYL6, HNRNPA1, MYH10, RASA3, SDK1, BRE, GOLIM4, RANGAP1, RTN4, IGF2BP2, EXOC5, ABHD14B, PRKD2, PRKD1, PRKD3, TM4SF1, RNF149, ARPC4, ARPC4-TTLL3, CMTM7, DTNA, DTNB, PAM, TRAPPC2P1, TRAPPC2, ATP6V1H, DPP3, RPL21, TJP1, HBA2, GOLT1B, BAG5, PSMA6, UBE2V1, UBE2V2, MPP5, GNG2, FBN3, ACYP1, PTGER2, VPS33B, LTBP2, SRP54, GMFB, FRMD6, FBLN5, GNPNAT1, SHMT2, SLC7A7, SULF2, LAMB1, COMP, SBF1, TTC7A, PDIA3, COBLL1, XPNPEP1, DNM1L, GRK5, GRK6, GRK4, CDSN, MVB12B, ALDH1A3, HP, HPR, AMPD2, KCNMA1, FN1, IMPDH2, APMAP, CC2D1B, TBC1D8B, COL12A1, PTPRF, CALM2, CALM1, CALM3, HNRNPD, ATP10D, FST, COL14A1, VEGFA, CTSC, CTSF, MYCT1, CD40, RPS2, SCP2, CRIP2, C1R, REXO2, M6PR, LOC388849, IFT81, DHRS7, PPP2R5C, HECTD1, ETFA, WDR61, GMPR2, LDLR, RPS27L, RPS27, PSMA4, ANP32A, ANP32B, SPPL2A, PSME1, COMMD4, SPNS1, SLC9A3R2, RPS15A, CARHSP1, FUS, TAF15, HAGH, HNRNPUL2-BSCL2, HNRNPUL2, GSPT1, UBFD1, LRRC57, DDX19A, DDX19B, HAPLN3, HAPLN4, BOLA2B, BOLA2, STXBP5, GCA, CHIA, ABCB6, COL5A1, WDR44, PDIA3, ZPR1, YIPF4, AP1S1, AP1S2, MMS19, CTDSP1, TSPAN15, MANF, POFUT2, PLOD3, MITD1, STRADB, PRDX4, SRPRB, MAGI1, ATP11B, MFSD1, IAH1, EFR3A, BRCC3, TXNDC17, NSF, PCYT2, CRK, MLKL, TFAP4, TOM1L1, EIF5A, EIF5AL1, EIF5A2, SRR, RPS15A, CCDC43, BAIAP2, SLC12A4, RPS13, MATN2, PI4KA, KIAA0368, ECM29, PSMD9, KIF5A, KIF5C, GPR176, PARVA, ITGA7, FHL2, MYO18A, LEKR1, GAS6, OLA1, TGOLN2, SYT1, STRA6, PSD3, PPP2R5E, IARS, NT5C, COPZ2, TANC2, RPL17, SRSF1, RPL38, FBXL20, RPL19, ARHGDIA, AKT2, SNRPD1, VWA1, ACE, ERBB2, CDKN2A, CDKN2B, MYL12A, MYL12B, YES1, RPL13, FNBP1L, TMEM8A, CUL4B, MYO1D, KATNAL2, SMAD4, RPS15, RPL22, TBCB, PKN1, SEPT9, SYNGR2, PRKCSH, RAD23A, EIF1, EIF1B, ACTG1, MRI1, PIN1, STAT3, UBXN6, DAZAP1, PDCD5, CARM1, CDC37, GPX4, PSENEN, RAB27B, COPE, ARHGEF1, NUMBL, HNRNPM, AP2S1, EMP3, RCN3, GGCT, JOSD2, CLEC11A, RPS5, MYO9B, AXL, PLAUR, RPL18A, SPATA22, EPS15L1, CHMP2A, KDELR1, KDELR2, RPS16, DPP9, TBC1D17, PAFAH1B3, ACOT7, MYO1C, SNAP23, STXBP3, AP3B1, TNFRSF10A, PSMD11, PSMD12, PGRMC1, CLIC1, QSOX1, IPO5, RTCA, AGRN, PSMD14, KPNA3, STK25, KRIT1, SDCBP, SDCBP, DDX3X, DDX3Y, CYR61, KPNA4, PDXK, CLDN4, CLDN9, CLDN6, CLDN3, PPAP2A, PPAP2B, ISLR, TXNDC9, HSPB6, ADAM10, ITGB1BP1, PRMT5, SLC9A3R1, TNFRSF10B, NRP1, MRAS, PSMA7, SCAMP3, TAX1BP3, GIPC1, CASK, HGS, PPP1R12A, PPP1R12B, XPO1, PLXNB2, NPC1, SCAMP1, SCAMP2, ARPC1B, ARPC2, ARPC3, PGRMC2, PFDN6, LAMA5, LEPROT, RER1, SURF4, INPPL1, NCAM2, STX7, SLC16A3, SLC31A1, ABCC3, ABCC4, P4HA2, YKT6, ARPC5, FLRT2, PLXNB1, PHGDH, ADAM12, GPR39, DYNC1LI2, PSMD3, PAPSS1, B4GALT5, TGFB1I1, TXNL1, TPD52L2, FIBP, AKR7A2, EPB41L2, ATP8B1, ATP8B4, DENR, XPOT, TSPAN6, ASNA1, ACTN4, KDELR3, SGTA, NARS, LANCL1, CALU, EDIL3, AHCYL1, AHCYL2, SPAG9, MAPK8IP3, PIP5K1C, DFNA5, NRP2, ACSL4, SNX3, ADCY9, SYNCRIP, HNRNPR, GREM1, EXOC3, PLIN3, SLC16A7, UGDH, CTNND1, SNX2, USO1, TOM1, PRAF2, EIF5B, DNAJA2, CUTA, SRGAP2, SRGAP2C, PLXNA2, WDR1, FZD7, SLIT3, ROCK2, CPNE3, DNAJC13, USP12, SEMA7A, PDCD6, ATP6V1G1, ATP6V1G2-DDX39B, ATP6V1G2, VPS4B, SH3BGRL, FLNB, SEC22B, ERLIN1, GPC4, CLDN11, TIPRL, RP2, SLC22A3, EIF3J, CBR3, IDH1, ATRN, STAM2, ARL6IP5, DCTN3, FLOT1, CPD, GLRX3, STC2, CIAO1, DDAH1, STK10, GFPT2, SLIT2, SEC24D, FARP2, DKK1, ABCA8, ENDOD1, AP2A2, PRSS23, S1PR2, UBL3, VAMP5, RTN3, VAPB, MPZL1, PGLS, ATG7, LYPLA2, IPO7, PGM3, APOM, FMNL1, ABCA1, SEC24A, SFT2D2, ACSL3, STAMBP, AP2A1, TMEM50A, BAG2, BAG3, CLDN1, CLIC3, TSPAN13, TSPAN31, DDAH2, ITGBL1, RECK, LDHA, ALDH1A1, GLUD1, GLUD2, CYB5R3, GSR, SOD1, F13A1, PNP, HPRT1, GOT2, EGFR, PGK1, AK1, C1R, F10, PLAT, ASS1, C3, TIMP1, CST3, CSTA, NRAS, HRAS, KRAS, TGFB1, PENK, NPY, IGF2, IL1B, IGHG1, IGHG3, HLA-A, COL1A1, COL3A1, COL4A1, LMNA, APOE, SLC4A1, FN1, FN1, FN1, RBP4, ORM2, ORM1, TFRC, FTL, FTH1, MT1X, MT1G, MT2A, MT1M, MT1E, MT1H, MT1A, ANG, VTN, CAT, ALDOA, CSTB, ANXA1, APOB, SOD2, OAT, KRT1, GAPDH, ASL, CAPNS1, HSPB1, RPN2, GNAI2, ATP1A1, ARG1, ITGB3, S100A8, SERPINB2, SERPINE1, ISG15, ALPL, EIF2S1, ICAM1, RPLP1, RPLP2, RPLP0, RPLP0P6, FABP3, ITGB1, PRKCB, MYL1, MYL3, COL5A2, UROD, INSR, FYN, GSN, GSN, S100A9, S100A6, ENO1, PYGL, GPI, NPM1, TPM3, ITGAV, LPL, SERPINE2, SERPINE2, EPHX1, DBI, LDHB, GPX1, P4HB, CTSD, ANXA2, ANXA2P2, CAPN1, TUBB, DCN, PFN1, BPGM, APRT, EPRS, CTSB, HSP90AA1, LYN, THBS1, HSPA1A, COL1A2, ANXA6, RHOC, PFKM, HSP90AB1, ASNS, MMP2, SOD3, MME, INHBA, MGP, ITGA2B, COL4A2, MFI2, ITGA5, VIM, RPS17L, RPS17, GNAI3, ANXA5, FGF2, ENO2, GSTP1, SNRPC, CXCL1, LGALS1, RBP1, SPARC, GSTM1, GSTM4, TPM1, TPM1, CLTA, ANXA4, CNP, PDGFRB, C1S, UCHL1, LTA4H, ALDOC, HIST1H2AJ, HIST1H2AH, H2AFJ, HIST2H2AC, HIST2H2AA3, HIST1H2AD, HIST1H2AG, HIST1H2AC, HIST3H2A, HIST1H2AB, RAP2A, SRGN, TROVE2, RRAS, HLA-A, BCL2, TXN, CTSA, PRKAR1A, ESD, HSPD1, CLU, HAPLN1, HSPA5, LAMC1, HSPA8, SLC2A1, SLC2A3, SLC2A14, UMPS, PYGB, RALA, SPTB, LAMP1, G6PD, DMD, IGF2R, ADH5, PRPS2, PCNA, COL11A1, COL6A1, COL6A2, COL6A3, PIP, ANXA3, ACTN1, SRC, PEPD, GP1BB, LAMP2, RNH1, BMP1, NCAM1, VCAN, VCAN, VCAN, ITGA4, EEF2, PDIA4, P4HA1, TPT1, F3, PLS3, PRKAR2A, MIF, CD99, HGF, FDPS, CPM, NID1, AKR1A1, PKM, PKM, PKM2, HSP90B1, IDE, DARS, JUP, AKR1B1, ANPEP, PVR, RAC2, MYOD1, B4GALT1, EZR, UCHL3, CD46, CD46, NME1, VEGFA, DSP, TIMP2, CBR1, HLA-A, PDGFRA, ATP2A2, FAH, HSPA6, RHOQ, GOT1, PRKCA, ITGA2, GJA1, PRKACB, PRKACA, KIN27, PRKACG, CAPN2, GAP43, HLA-G, CTPS1, ENG, PFKL, GM2A, LGALS3, IGFBP3, FLT1, TCP1, IGFBP2, ITGB5, ARF4, RPL7, VCL, PGAM1, SDC1, CDH2, GNAZ, VCAM1, NCL, GGT1, GGT3P, GGT2, SRM, CSNK2A2, ATP2B1, EIF2S2, RAB3A, RAB3B, RAB4A, RAB6A, RAB6B, NPR2, PSMB1, COL5A1, PTMS, GSTM3, ATP6V1B2, ATP6V1C1, CSRP1, FLNA, ACO1, IRP1, S1PR1, TNFAIP3, NT5E, TBXA2R, VDAC1, BGN, COMT, TGM2, OSBP, GART, PAICS, UBA1, NME1-NME2, NME2, NME1, ENPP1, HNRNPA2B1, IGFBP4, FBLN1, ITGA6, PPIB, WARS, RPS3, JAK1, PTPRG, AHCY, CFL1, ATP2B4, LAMA2, EEF1B2, IGFBP5, ACP1, TNC, MYL9, F2R, AZGP1, RPS12, FAS, DNAJB2, PSMA1, PSMA2, PSMA3, ITGA3, PTX3, MSN, DDX6, CTNNA2, S100A4, MGAT1, PTBP1, TARS, VARS, EEF1G, STOM, YWHAQ, MARK3, ATP6V0C, DPP4, RPL10, COL8A1, CD82, CALR, PSMB8, PSMA5, PSMB4, PSMB6, PSMB5, LOX, MAPK1, LAP3, TPP2, IMPA1, CTGF, EPHA2, EPHB2, SHC1, SHC2, CRABP2, MARCKS, GNA11, PRDX6, BLVRB, PRDX5, DDT, DDTL, PRDX3, RPL12, ECHS1, CMPK1, PEBP1, BDKRB2, HLA-A, HLA-A, HLA-B, HLA-C, HLA-C, ADSS, LRPAP1, ADSL, SLC7A1, LCN1, LCN1P1, CORO1A, GDI1, S100A7, SDC4, DNAJA1, ATIC, CASP14, YWHAB, YWHAB, SFN, STIP1, S100A11, PRDX2, CCKAR, GBP1, STX2, KIF5B, ABCC1, RNASE4, SDC2, CD68, HSPA4, GPC1, CTNNA1, CTNNB1, SERPINB6, NF2, RDX, SPR, PTGS2, THBS2, KRT9, FBN1, MYH9, BSG, BSG, TIMP3, GLRX, KRT2, PSMC2, SLC16A2, CHI3L1, GGT5, ARL2-SNX15, ARL2, ARL3, MAP2K2, MAP2K1, RPL4, PGM1, GNL1, SERPINF1, TGFBR2, HPCAL1, HPCA, TAGLN2, TALDO1, HSPA9, RPS19, RPL3, COL15A1, COL18A1, CAPG, IL6ST, CCT6A, NNMT, MDH1, EIF2S3, EIF2S3L, CD200, WNT5A, CSK, GARS, STAT1, ECE1, SLC1A3, SLC1A1, SLC1A4, PAFAH1B1, PTGIR, MCAM, RANBP1, NAMPT, NAMPTL, PSMC4, PPIC, VDAC2, USP5, MAPK9, MAPK10, CRKL, GSTM5, BDKRB1, RPL5, RPS9, MAP1B, NEDD4, UTRN, IQGAP1, RABIF, CAPZA2, CAPZB, EIF1AX, EIF1AY, RPL29, XDH, SLC6A8, LIMS1, GLIPR1, CXCL12, PREP, TFPI2, GCLM, CD151, PSMD8, GSS, CCT5, CSNK1A1, CSNK1A1L, CD97, MARCKSL1, DNASE1L1, ALDH9A1, RPL34, LMAN1, FASN, CCT3, TUFM, ALDH7A1, AARS, SARS, PSMB3, PSMB2, THBS3, ACADVL, TMED10, HINT1, RGS19, GSK3B, NT5C2, GMPS, GNAQ, GNG10, MMP14, SLC26A2, SERPINB8, SERPINB9, SERPINH1, PDLIM4, VASP, DNM2, BCAM, CCT8, ANXA11, RAB5C, RAB7A, RAB13, RAB27A, PLCD1, DUSP3, BCAP31, TPMT, CAV2, PLXNA3, VAMP7, ADCY7, AKR1D1, LUM, RAP1GDS1, SLC7A2, SMS, EFNB2, STC1, THOP1, CAPZA1, BLVRA, ARFIP1, ACLY, PGGT1B, COPB1, COPA, SLC5A3, SLC16A1, IST1, SUB1, RARS, CACNA2D1, YARS, USP14, HSPA2, BCAT1, ATP12A, ATP1B3, RAD23B, EPHB4, GAS1, ALDH18A1, NAPA, MFAP2, EIF5, SLC12A2, CSE1L, VCP, ADK, LAMB2, CDH11, CDH13, SEC13, HNRNPH2, EIF3B, FCGRT, BID, ITGA1, EIF6, ANTXR2, CD81, TPI1, ACTB, EIF4A1, RPS20, PRPS1, S100A10, CDC42, DSTN, RAB8A, SPCS3, RAB2A, RAB5B, RAB10, UBE2D3, UBE2D2, UBE2M, UBE2N, RAB14, ACTR3, ACTR2, ACTR1A, COPS2, RAP1B, RAP2B, RPS3A, RPL15, RPL27, RHOA, VBP1, STXBP1, UFM1, NUTF2, HNRNPK, YWHAG, RPS7, PPP1CA, PPP1CB, NCS1, PSMC1, PSMC5, RPS8, YWHAE, RPS14, RPS18, RPS29, RPS11, SNRPE, LSM3, TMSB4XP4, TMSB4X, ARF6, PSMC6, RPL7A, ETF1, CNBP, RPS4X, RPS4Y1, RPS4Y2, PPP2CB, ACTA2, ACTG2, RHOB, RPS6, HIST1H4A, RPL23, RAP1A, RPS25, RPS26P11, RPS26, RPS28, GNB1, GNB2, RPL10A, RPL11, PPIA, FKBP1A, RPS27A, UBB, UBC, UBA52, UBBP4, GRB2, RAC1, AP2B1, GNAS, GNAS, GNAS, GNAI1, YWHAZ, PPP2R2A, PPP2R2D, DYNLL1, DYNLT1, GNG5, RPS21, GNB2L1, ACTG1, TMSB10, PPP2CA, YBX1, CSNK2B-LY6G5B-1181, CSNK2B, TPM4, ACTC1, ACTA1, ACTG2, UBE2L3, EEF1A1, EEF1A1P5, TUBA1B, KLK9, TUBB4B, PAFAH1B2, HBB, SIRPA, SIRPB1, PIP4K2B, CSNK1G2, GSTO1, ADAM17, SRPX, BASP1, DCD, SMAD3, ARF1, ARF3, ARF5, RHOG, MXRA7, TNFAIP6, DAB2, HSPG2, EFNB1, ATP8B2, HDLBP, CDK6, CDK5, CLTC, FKBP3, HNRNPU, SPTBN1, SET, FABP5, CAP1, CAP1, SLC7A5, PFKP, OCRL, PLCB3, ROR2, TAGLN, DSG1, MAP2K1, TEK, FKBP4, NUCB1, RPL6, AKAP12, GNA12, CAV1, TNFAIP2, PLAUR, GBE1, NOTCH2, GLO1, ACVR1, YWHAH, PLP2, PRKCD, PTPN11, GFPT1, FMOD, PRDX1, C1QBP, CKAP4, ENPEP, COL16A1, SPAG1, BAX, LRP1, ARHGAP1, TGM3, DHX9, CRYZ, LGALS3BP, LOXL1, MFGE8, MFGE8, DSC1, SPOCK1, VAC14, AHNAK, SMAGP, GALNT2, AP1B1, BST2, ST3GAL1, SCRN1, KIAA0196, TWF1, ASPH, EFEMP1, FSTL1, STX4, DPYD, FAP, AIMP1, ILF3, PTPRJ, DLG1, MYO1E, PTP4A2, ABR, ARHGAP5, STRN3, STRN4, FLII, COASY, SPP2, PRKAA1, PPFIA1, PPFIA3, PPFIA2, PPFIA4, PAK2, PSMD2, DNAJC3, PAPPA, PTK7, SGCG, SLC14A1, EIF3I, PLD1, DYNC1I2, BTN1A1, ILK, SNTB2, SLC39A6, PDAP1, ADAM9, ROCK1, TCIRG1, PICALM, TUBB3, CAMK2G, CAMK2B, NAE1, CUL1, CUL2, CUL3, CUL4A, RAB31, RAB32, TPBG, FHL1, FHL3, ALCAM, PKP1, BMPR2, TUBB2A, TUBB2B, IDI1, PRKG1, CKAP5, COTL1, SCARB2, NID2, DAG1, DSG2, SCRIB, TTLL12, DPYSL3, DYNC1H1, CTTN, FLOT2, FLNC, FZD2, GNA13, GAMT, GALE, LRRC32, FAT1, DSC3, INPP5A, TRIP12, GANAB, RFTN1, MVP, LASP1, PTGR1, RAB39A, KPNB1, NAA25, VEPH1, CHMP4A, PSMD6, Sep-02, SNX17, RAB3GAP1, SLC39A14, KARS, EIF4H, POSTN, PCOLCE, PLCB4, PLEC, PPA1, STK38, PTPRK, RASA2, RAB35, LLGL1, PCBP1, RHEB, RSU1, TGFBI, TRIP10, TRIP6, MAPRE1, MYLK, SLC1A5, SMAD1, STXBP2, ZNF14, VAMP3, VAMP2, ATP6AP1, RAB11B, RAB11A, ZYX, ADRM1, CCDC6, UAP1, IGFBP7, LAMA4, EXT1, PSMD5, PKN2, DDB1, DPYSL2, SYPL1, SGCB, ECM1, DBN1, PTGIS, FSCN1, ATP2B3, CA9, MEP1A, DDR2, UGP2, TMEM132A, INF2, KIF26B, QRICH1, LEPRE1, DAK, SERPINB12, TUBB8, PREPL, TBC1D10B, ANO6, SVEP1, TMEM119, FNDC1, RFTN2, TP5313, PLEKHO1, ALF, STON1, CYBRD1, NAALADL2, HSP90AB4P, HSP90AB2P, HERC4, TMEM67, DPCD, VPS16, COLEC12, DNMBP, LDLRAP1, OTUD7B, OTUD7A, WASF1, TPRG1L, SH3BGRL3, SLC39A1, UBR4, C9orf64, KPRP, XP32, TM9SF3, OGFRL1, SPO11, STRIP1, STRIP2, FAM171A1, BROX, FAM208B, PEAR1, ARHGEF2, RRAGB, RRAGA, RAB18, CD276, STEAP3, HGSNAT, MBLAC2, ARHGAP17, NXN, VASN, PTRHD1, LAMTOR1, TWF2, RAB12, TENM4, PTRF, CC2D1A, FAHD2A, FAHD2B, CNNM4, FAM171B, TLDC1, RHBDF2, TRAF7, CSPG4, MOXD1, LRSAM1, HHIPL2, PI16, FAT4, PACS1, CD109, C1QTNF1, FAM65A, ANKRD13D, RASSF6, UBN2, LHFPL2, VPS13C, MOB3C, UBE2R2, TUBA1A, TUBA1C, TUBA3C, TUBA3E, TUBA8, CCDC80, BTN2A1, SND1, BZW1, EIF3M, CYFIP1, TAOK1, MOB1B, CHMP1B, ZC3HAV1, NEGR1, LIMS2, GOLGA7, PODN, SRGAP1, HUWE1, TMEM179B, AMIGO2, TMEM55B, TTC7B, PHLDB1, TXNDC5, SERINC5, VPS36, CAND1, TMEM200A, PPFIBP1, SBF2, SBF1, TICAM2, TMED7, TICAM2, XYLT1, STX12, AEBP1, PLD3, LIX1L, AHNAK2, CCDC50, SLITRK4, SLC44A2, SLC44A2, WDFY1, TEX2, FAM114A1, DCUN1D3, LRRC8A, SULF1, UBR1, UEVLD, CMIP, EXOC8, SLC6A16, ANKRD13A, UNC5B, SPG20, LRRC47, LYPD1, DOS, SLC35F6, C2orf18, ARHGAP18, ASCC3, EHBP1L1, PLCD3, SFRP1, MINK1, FAM26E, SLC15A4, ADAMTSL1, CCNYL1, ENAH, BMPER, DCBLD1, TDRD5, ATP11C, GOLM1, FAM63B, FAM63A, SERBP1, APOA1BP, CCNY, LRRN4CL, MAPK1IP1L, APPL2, GPRC5A, STXBP6, TSPAN14, SVIP, VANGL1, WDR48, NDNF, UBA3, TMEM167A, SPPL2B, HM13, CD99L2, PLEKHO2, NEK7, MICAL1, DTD1, IPO4, PPP4R1, UBASH3B, LRRC15, FRS2, RAB2B, PPP1R13L, CEMIP, PDCD6IP, UBTD2, FBLIM1, BRK1, SLC38A5, PHLDA1, SNX33, UBLCP1, APH1B, C1orf85, SLC44A1, PALLD, TTN, OVCA2, DDX1, PIEZO1, SLC7A6, GBF1, NCSTN, TM9SF4, NDRG1, HSPH1, GCN1L1, PXDN, SGCD, PVRL2, PVRL2, RABGGTA, HTRA1, ARPC1A, STAM, HAS2, GGH, NEO1, OSTF1, GLG1, UPF1, COPS5, RAB8B, RIT1, TNPO1, NINJ1, DVL3, USP9X, USP9Y, CUL5, LPP, PTP4A1, SCAMP4, IGSF8, ERGIC1, SYAP1, FERMT2, LRRC59, MRGPRF, AIDA, ARL8A, ARL8B, MOB3A, DOCK10, EFHD2, EFHD1, PPP1R14B, LIMK2, RHBDF1, CTHRC1, ISOC1, KCTD12, SHISA4, CMBL, RSPRY1, L3HYPDH, CNRIP1, DYNLL2, CPNE2, S100A16, PERP, CHMP6, PGM2, SCARF2, PDLIM5, ERO1L, GMPPA, ITCH, KIRREL, LRIG1, LOXL4, DCHS1, MEGF10, EXOC2, CNDP2, SNX27, IFT74, DOCK7, LRRC7, IPO9, DCBLD2, GPR124, FMNL2, TRNT1, TMEM237, GSDMA, SLC38A2, VPS35, PURB, PANX1, SNX18, NUDCD1, ERBB2IP, C16orf13, MYADM, FAM129B, PSMB7, PSMD1, PFDN5, PARK7, VAT1, S100A13, TTC1, DNAJC7, C12orf57, OSMR, CHP1, HSD17B10, NAP1L4, TM9SF2, CCT7, AGPAT1, PKP2, SH3GL1, GDF15, ARPC5L, PDCD1LG2, TMEM47, CORO1B, CPPED1, VPS25, MXRA8, SDF4, MIEN1, PELO, ERP44, LXN, ESYT1, MARVELD1, CCM2, COPS4, DCTN5, LRRC1, TUBB6, PDCD10, BDH2, NTMT1, TMED9, ACAT2, JAM3, RAB11FIP5, TBC1D10A, NAA15, SLC12A9, AP1M1, ITPA, CADM1, FRMD8, ULBP3, ULBP2, FAM129A, ZDHHC5, TTYH3, TINAGL1, C20orf27, TOLLIP, ARL6, ITFG3, WNT5B, MESDC1, EHD4, C1orf21, TRIOBP, SLK, TAOK3, SLC12A5, SLC12A7, C11orf68, TXNIP, ACBD3, UNC45A, DNAJC5, CHMP4B, RNPEP, SMOC1, EPB41L1, GLIPR2, EHD1, CDCP1, CLMP, EPS8L2, ANTXR1, SH2D4A, DOCK5, ATP13A3, UBE2Z, FAM188A, MOB1A, GORASP2, C6orf211, LRRC40, SLC52A2, PPCS, UBTD1, SMURF2, GNB4, BCL2L12, CACYBP, RRAGC, RRAGD, PARVB, PROK2, GLOD4, ANKH, VAT1L, EPB41L5, EPB41L4B, CSNK1G1, CD248, S100A14, MYO10, NRXN3, VTA1, TNFRSF12A, IL1RAP, RIC8A, PLCB1, TIGAR, HINT3, NIT2, PVRL3, MYO5C, PDLIM7, SAR1A, NANS, MXRA5, SLC17A5, OLFML3, OSTC, CDC42SE1, HEBP1, VPS45, PHPT1, SERINC1, ARHGAP35, PLSCR3, TMEM256-PLSCR3, LANCL2, STARD5, ATG3, ECHDC1, LIN7C, FAM49B, NUDT15, EXOC1, TMEM30A, EVA1B, TMEM51, COMMD8, RAB20, CMTM6, ARL15, ACTR10, IGF2BP1, HSPBP1, MYOF, EHD3, EHD2, CD274, FLRT3, LMCD1, MPP6, CHMP5, VAPA, SH3BP4, VPS18, DIP2B, TENM3, PTGFRN, PCDH10, RRBP1, ANKIB1, ANKFY1, ATXN10, NCDN, MRC2, CRNN, GNG12, TNFRSF10D, SPAST, GULP1, GRHPR, CTSZ, CKLF, CTNNAL1, PEF1, DNAJB4, STK39, ADD3, ABCF2, SLC23A2, TES, SUSD2, LAMTOR3, NPC1L1, CHORDC1, TMEM2, PFDN2, SLCO3A1, LNPEP, NAGK, ANXA10, DBNL, DCTN4, VPS28, LSM7, PACSIN3, TRHDE, ANGPTL2, ITGA11, CDV3, RAB21, RAB22A, PSME2, RAB23, MCTS1, ZDHHC8, SLC39A10, ASAP1, HEG1, ANKRD50, TBC1D24, CORO1C, PYCARD, NOTCH3, ICAM5, UBQLN1, SNX12, VPS4A, PCDHGC3, STUB1, PACSIN2, STX8, PLA2G2D, PSMD13, PROCR, ABCG2, COPS3, TTF2, FZD1, SLC7A11, WASF3, SHOC2, PA2G4, CHMP2B, GNE, C14orf166, RUVBL1, NUDC, CFL2, ITM2B, SLC5A6, NCKAP1, EXOC6B, DIP2C, STK38L, EPB41L3, FAN1, LAMTOR2, TMA7, AP3M1, AP3M2, MEMO1, LSM2, SH3GLB1, CAB39, SBDS, PPIL1, UFC1, RTCB, FBXO7, RAP2C, TLN1, DAAM1, PLXND1, IRS2, LOXL2, RNF114, PPME1, PCDHGB7, PCDHGB6, PCDHGB5, PCDHA9, PHLDA3, GMPPB, TRPV2, CDC42BPB, IER3IP1, SNX9, SNX8, HEBP2, PSAT1, F11R, GPC6, NPTN, DKFZp566H1924, COPG1, LHFP, CLIC4, CFAP20, EMILIN1, DYNC1LI1, EPN1, CSNK1G3, SLC30A1, SLC4A7, ROBO1, SLC4A4, FCGBP, PCLO, CAPN7, WASF2, and combinations thereof.

In some cases, proteins that contribute to therapeutic efficacy or that mediate paracrine signaling to effect therapeutic efficacy of exosomes isolated using CD39 binding agents comprise CD39, CD39L3, and/or CD73, or structural or functional analogues thereof differing in sequence, length or sequence and length, but retaining a collective ability to reduce ATP or ADP to the free purine adenosine. In some cases, proteins that contribute to therapeutic efficacy or that mediate paracrine signaling to effect therapeutic efficacy comprise CD39. In some cases, proteins that contribute to therapeutic efficacy or that mediate paracrine signaling to effect therapeutic efficacy comprise CD39L3. In some cases, proteins that contribute to therapeutic efficacy or that mediate paracrine signaling to effect therapeutic efficacy comprise CD73. In some cases, exosomes disclosed herein deliver one or more of the above proteins to reduce inflammation. Some exosomes deliver proteins that affect local ATP, ADP and/or AMP concentrations, for example by catalyzing the transformation of ATP into ADP, AMP or free purine, so as to reduce at least one of ATP concentration, ADP concentration and AMP concentration. Alternately or in combination, some exosomes deliver proteins that increase free purine concentration, for example by converting at least one of ATP, ADP and AMP to free purine. Conversion of ATP, ADP and AMP to free purine is accomplished in some cases through a combination of proteins comprising CD39 and CD73. Alternately, in some cases a single enzymatic activity releases free purine from at least one of ATP, ADP and AMP. Some exosomes deliver an enzyme having at least one of ATPase, ADPase, AMPase, and adenosine depurinase activity. In various embodiments, exosomes comprise not more than 2, 3, 4, 5, 6, 7, 8, 9, 10, 15, 20, 30, 40, 50, 60, 70, 80, 90, 100 or more than 100 proteins from the above list. In various embodiments, exosomes comprise at least 2, 3, 4, 5, 6, 7, 8, 9, 10, 15, 20, 30, 40, 50, 60, 70, 80, 90, 100 or more than 100 proteins from the above list. In various embodiments, exosomes comprise not more than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list. In various embodiments, exosomes comprise not less than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list. In various embodiments, not more than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list are purified, for example from exosome compositions, for treatment of disease. In various embodiments, not less than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list are purified, for example from exosome compositions, for treatment of disease. In some cases, purified proteins from the above list are combined with exosome compositions, for example using the exosomes as a delivery mechanism, for treatment of disease.

Some exosome compositions isolated using CD39 binding agents disclosed herein comprise nucleic acids, such as miRNAs that contribute to therapeutic efficacy, or that mediate paracrine signaling to effect therapeutic efficacy. In some aspects, the composition comprises microRNAs (miRNAs). miRNAs include but are not limited to let7b miRNA. In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

A therapeutically active exosome composition such as a paracrine signaling exosome composition disclosed herein, in some cases, comprises an immunosuppressive drug. Immunosuppressive drugs contemplated herein include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. Some exosome compositions comprise anti-TNF antibodies, including but not limited to infliximab, adalimumab, certolizumab, and golimumab. Exosome compositions comprise TNF inhibitors including but not limited to etanercept, xanthine derivatives, and bupropion. In some cases, exosome compositions comprise at least one NSAID. In some cases, exosome compositions comprise at least one steroid.

Methods of Treatment

SDC2+ and SDC2+CD39+ stromal stem cell and SDC2+ and SDC2+CD39+ exosome compositions isolated based on expression of CD39 disclosed herein include therapeutic compositions for methods and uses in treatment of disease, in some cases via paracrine signaling activity. Some SDC2+ and SDC2+CD39+ stromal stem cell and SDC2+ and SDC2+CD39+ exosome compositions modulate an inflammation response in a mammal. Therefore, disclosed herein are methods of modulating an inflammation response in a mammal by administering at least one purified SDC2+ or SDC2+CD39+ stromal stem cell and SDC2+ or SDC2+CD39+ exosome compositions to the site of the inflammation response. Also disclosed herein are purified SDC2+ and SDC2+CD39+ stromal stem cell and SDC2+ and SDC2+CD39+ exosome compositions for use in modulating an inflammation response in a mammal by administering at least one purified SDC2+ and SDC2+CD39+ stromal stem cell or SDC2+ and SDC2+CD39+ exosome composition to the site of the inflammation response. Also disclosed herein are purified SDC2+ and SDC2+CD39+ stromal stem cell and SDC2+ and SDC2+CD39+ exosome compositions for use in preparation of a medicament for modulating an inflammation response in a mammal by administering at least one purified SDC2+ and SDC2+CD39+ stromal stem cell or SDC2+ and SDC2+CD39+ exosome composition to the site of the inflammation response.

Methods and uses include various routes of administration suitable for reaching sites of inflammation, which vary depending on the inflammation response which requires treatment. Routes of administration include but are not limited to parenteral (including subcutaneous, intravenous, intra-arterial, intraosseous, intracerebral, intra-cerebroventricular, intrathecal, intramedullary, intra-articular, intramuscular, or intraperitoneal injection), rectal, respiratory or inhalation, topical, transdermal, and oral (for example, in capsules, suspensions, or tablets). For some indications, it is desirable to administer SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein via intravenous administration. In particular, intravenous administration is often preferred to deliver SDC2+ and SDC2+CD39+ stromal stem cell or SDC2+ and SDC2+CD39+ exosome compositions or compositions derived from SDC2+ and SDC2+CD39+ stromal stem cell or SDC2+ and SDC2+CD39+ exosomes to a mammalian lung such as a human lung.

For some indications, it is desirable to administer SDC2+ and SDC2+CD39+ stromal stem cell and SDC2+ and SDC2+CD39+ exosome compositions such as paracrine signaling SDC2+ and SDC2+CD39+ stromal stem cell or SDC2+ and SDC2+CD39+ exosome compositions disclosed herein via a respiratory or inhalation route using an inhalation device. An inhalation device is capable of administering therapeutic compositions to the respiratory airways of a patient. In halation devices include conventional inhalation devices such as metered dose inhalers, dry powder inhalers, jet nebulizers, ultrasonic wave nebulizers, heat vaporizers, soft mist inhalers, and high efficiency nebulizers. Nebulizers, metered dose inhalers, and soft mist inhalers deliver therapeutics by forming an aerosol, which includes droplet sizes that can easily be inhaled. A patient within the bounds of an inhalation therapy can use the aerosol. A nebulizer is able to turn a therapeutic or medication into a fine aerosol mist that is delivered to the lungs of an individual.

Nebulizers include high efficiency nebulizers. High efficiency nebulizers are inhalation devices that comprise a micro-perforated membrane through which a liquid solution is converted through electrical or mechanical means into aerosol droplets suitable for inhalation. High efficiency nebulizers can deliver a large fraction of a loaded dose to a patient. In some embodiments, the high efficiency nebulizer also utilizes one or more actively or passively vibrating microperforated membranes. In some embodiments, the high efficiency nebulizer contains one or more oscillating membranes. In some embodiments, the high efficiency nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the patient inhales the aerosol from the mixing chamber. Still yet, in some embodiments, the high efficiency nebulizer contains a pulsating membrane. In some embodiments, the high efficiency nebulizer is continuously operating.

For some indications, diseases or disorders, it is desirable to administer SDC2+ and SDC2+CD39+ stromal stem cell and SDC2+ and SDC2+CD39+ exosome compositions such as paracrine signaling SDC2+ and SDC2+CD39+ stromal stem cell and SDC2+ and SDC2+CD39+ exosome compositions topically (e.g., applied directly to the skin of the individual being treated). In some cases, topical administration is used to treat diseases of the skin. Topical administration includes epicutaneous administration. SDC2+ and SDC2+CD39+ stromal stem cell or SDC2+ and SDC2+CD39+ exosome compositions for topical administration are formulated specifically to be administered to the skin. Such topical SDC2+ and SDC2+CD39+ stromal stem cell or SDC2+ and SDC2+CD39+ exosome compositions include but are not limited to solutions, lotions, creams, ointments, gels (including hydrogels or collagen gels), foams, transdermal patches, powders, pastes, and tinctures. In some cases, SDC2+ and SDC2+CD39+ stromal stem cell or SDC2+ and SDC2+CD39+ exosome compositions comprise a hydrogel or a collagen gel.

Certain indications, diseases, or disorders benefit from administration of SDC2+ and SDC2+CD39+ stromal stem cell and SDC2+ and SDC2+CD39+ exosome compositions such as paracrine signaling SDC2+ and SDC2+CD39+ stromal stem cell and SDC2+ and SDC2+CD39+ exosome compositions to the eye (e.g., intraocular or ophthalmic). SDC2+ and SDC2+CD39+ stromal stem cell or SDC2+ and SDC2+CD39+ exosome compositions for administration to the eye comprise formulations (e.g., buffers or excipients) suitable for administration to the eye.

Injection of SDC2+ and SDC2+CD39+ stromal stem cell and SDC2+ and SDC2+CD39+ exosome compositions such as paracrine signaling SDC2+ and SDC2+CD39+ stromal stem cell and SDC2+ and SDC2+CD39+ exosome compositions to a subject is effective in treating certain indications, diseases, or disorders. Delivery of an SDC2+ and SDC2+CD39+ stromal stem cell and SDC2+ and SDC2+CD39+ exosome composition via injection includes but is not limited to injection to the lymph nodes, subcutaneous injection, intramuscular injection, intravenous injection, intraperitoneal injection, intrathecal injection, intradermal injection, intraarticular injection, and other injection methods suitable for methods herein. SDC2+ and SDC2+CD39+ stromal stem cell and SDC2+ and SDC2+CD39+ exosome compositions for injection comprise formulations or physiologically acceptable buffers or excipients for injection.

Certain indications, diseases, or disorders benefit from administration of SDC2+ and SDC2+CD39+ stromal stem cell and SDC2+ and SDC2+CD39+ exosome compositions such as paracrine signaling SDC2+ and SDC2+CD39+ stromal stem cell and SDC2+ and SDC2+CD39+ exosome compositions directly to the heart. Direct cardiac application of SDC2+ and SDC2+CD39+ stromal stem cell and SDC2+ and SDC2+CD39+ exosome compositions such as paracrine signaling SDC2+ and SDC2+CD39+ stromal stem cell or SDC2+ and SDC2+CD39+ exosome compositions include but are not limited to intra-cardiac, intra-pericardial, or intra-coronary artery injection.

SDC2+ and SDC2+CD39+ exosome compositions such as paracrine signaling SDC2+ and SDC2+CD39+ exosome compositions used in methods of treatment and uses in a mammal, in some cases, include one or more antigens. In methods of treatment and uses where the SDC2+ and SDC2+CD39+ exosome composition includes one or more antigens, the antigen is not exposed to the individual's humoral immune system. In these cases, the individual does not develop a humoral immune response to the antigen.

SDC2+ and SDC2+CD39+ stromal stem cell and SDC2+ and SDC2+CD39+ exosome compositions such as paracrine signaling SDC2+ and SDC2+CD39+ stromal stem cell and SDC2+ and SDC2+CD39+ exosome compositions used in methods of treatment and uses in a mammal comprise SDC2 and/or CD39 or are SDC2+ and SDC2+CD39+. When the stromal stem cell or exosome composition is analyzed, at least 20% of the stromal stem cells or exosomes comprise SDC2 and at least 20% of the stromal stem cells or exosomes comprise CD39. In some cases, the SDC2+ and SDC2+CD39+ stromal stem cell or SDC2+ and SDC2+CD39+ exosome composition used in methods of treatment and uses comprise a composition where at least 30%, 40%, 50%, 60%, 70%, 80%, 90%, 95%, 99%, or more of the stromal stem cells or exosomes comprise SDC2 and at least 30%, 40%, 50%, 60%, 70%, 80%, 90%, 95%, 99%, or more of the stromal stem cells or exosomes comprise CD39. The proportion of stromal stem cells or exosomes in the composition comprising SDC2 and CD39 is determined by immunofluorescence, for example flow cytometry, fluorescence microscopy, electron microscopy, or other suitable method.

Stromal cell compositions used in methods of treatment herein, in some cases, are modified to increase the therapeutic efficacy of the stromal stem cell composition. In some cases, cells are genetically modified to overexpress an apyrase as disclosed herein, such as CD39, a structural or functionally active variant of CD39 or other protein having apyrase activity. In some cases, cells are genetically modified to overexpress CD39L3. Genetic modification of stromal cells is accomplished by methods including but not limited to transfection of the stromal cells with one or more plasmids that comprise the CD39 or CD39L3 coding sequence and a promoter, such as a CMV, SV40, EF1a, or CAG promoter. Genetic modification of stromal cells, in some cases, is accomplished by infection of the stromal cells with a virus that comprises the CD39 or CD39L3 coding sequence and a promoter.

While SDC2+ and SDC2+CD39+ exosome compositions such as paracrine signaling SDC2+ and SDC2+CD39+ exosome compositions described herein, in some cases, are derived from cells isolated based on expression of CD39, the exosome compositions do not comprise living cells. The exosome compositions, therefore, are non-tumorigenic, that is, they do not increase the susceptibility of a subject to developing a tumor or cancer.

Methods of treatment and uses disclosed herein comprise administering to a mammal an SDC2+ and SDC2+CD39+ stromal stem cell or SDC2+ and SDC2+CD39+ exosome composition comprising SDC2+ and SDC2+CD39+ stromal stem cell or SDC2+ and SDC2+CD39+ exosomes, for example paracrine signaling SDC2+ and SDC2+CD39+ stromal stem cell or SDC2+ and SDC2+CD39+ exosomes or in vitro SDC2+ and SDC2+CD39+ stromal stem cell or SDC2+ and SDC2+CD39+ exosomes, and mixtures of SDC2+ and SDC2+CD39+ exosomes and SDC2+ and SDC2+CD39+ mesenchymal stem cells (e.g., SDC2+ and SDC2+CD39+ mesenchymal stromal stem cells). In some instances, methods of treatment and uses use exosome compositions that include compositions comprising SDC2+ and SDC2+CD39+ exosomes or in vitro exosomes and regulatory T cells. Regulatory T cells include CD25+ regulatory T cells, CD4+ regulatory T cells, FoxP3+ regulatory T cells, CD25+CD4+FoxP3+ regulatory T cells, and combinations thereof. In some instances, methods of treatment and uses that use exosome compositions include compositions comprising in vitro SDC2+ and SDC2+CD39+ exosomes, SDC2+ and SDC2+CD39+ mesenchymal stem cells, and regulatory T cells.

Methods of treatment and uses herein use SDC2+ and SDC2+CD39+ exosome compositions such as paracrine signaling SDC2+ and SDC2+CD39+ exosome compositions that retain potency or activity after being frozen or cryopreserved without the use of a cryoprotectant. Cryoprotectants include DMSO, glycerol, polyethylene glycol, propylene glycol, glycerine, polyvinylpyrolidone, sorbitol, dextran, and trehalose. The exosome compositions used in methods of treatment and uses also retain potency after being frozen without using special freezing protocols. Special freezing protocols include flash freezing, programmable rate freezer, and freezing in an insulated container. The exosome compositions used for methods of treatment and uses are frozen in buffer or culture media. Buffers include physiologically acceptable buffers such as phosphate buffer, histidine buffer, citrate buffer, acetate buffer, and other suitable buffers. In some cases, methods of treatment and uses herein use exosome compositions are lyophilized or have been lyophilized.

Methods of treatment and uses disclosed herein use SDC2+ and SDC2+CD39+ stromal stem cell compositions that retain potency or activity after being frozen or cryopreserved. Cryoprotectants include DMSO, glycerol, polyethylene glycol, propylene glycol, glycerine, polyvinylpyrolidone, sorbitol, dextran, and trehalose. The SDC2+ and SDC2+CD39+ stromal stem cell compositions used in methods of treatment and uses also retain potency after being frozen using special freezing protocols. Special freezing protocols include flash freezing, programmable rate freezer, and freezing in an insulated container. The SDC2+ and SDC2+CD39+ stromal stem cell compositions used for methods of treatment and uses are frozen in buffer or culture media mixed with a cryoprotectant. Buffers include physiologically acceptable buffers such as phosphate buffer, histidine buffer, citrate buffer, acetate buffer, and other suitable buffers.

Methods of treatment and uses disclosed herein comprise administration of compositions comprising SDC2+ stromal stem cells isolated based on expression of CD39 in a therapeutically effective amount. Administration of a therapeutically effective amount of SDC2+ and SDC2+CD39+ stromal stem cells, in some cases, comprises administration of $10^3$ to $10^8$ SDC2+ and SDC2+CD39+ stromal stem cells, for example $10^3$, $10^4$, $10^5$, $10^6$, $10^7$, $10^8$, or more SDC2+ and SDC2+CD39+ stromal stem cells of the composition. Methods of treatment and uses include administration of SDC2+ and SDC2+CD39+ stromal stem cells compositions, which in some cases, are concentrated to be diluted by the individual or health care provider prior to administration. In some cases, methods of treatment and uses comprise administration of SDC2+ and SDC2+CD39+ stromal stem cells compositions that are diluted and ready to be administered by the individual or health care provider. In some cases, methods of treatment and uses comprise administration of SDC2+ and SDC2+CD39+ stromal stem cells compositions that are contained in single use vials, syringes, or IV bags. In some cases, methods of treatment and uses comprise administration of a dose from a container comprising multiple doses.

Methods of treatment and uses disclosed herein comprise administration of compositions comprising exosomes such as paracrine signaling exosomes in a therapeutically effective amount. Administration of a therapeutically effective amount of exosomes, in some cases, comprises administration of $10^6$-$10^8$ exosomes, for example $10^6$, $10^7$, $10^8$, or more exosomes of the composition. In some cases, administration of a therapeutically effective amount of exosomes comprises administration of 1 µg to 700 mg of exosomes, for example 1 µg, 10 µg, 20 µg, 50 µg, 100 µg, 150 µg, 200 µg, 250 µg, 500 µg, 750 µg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Methods of treatment and uses include administration of exosome compositions, which in some cases, are concentrated to be diluted by the individual prior to administration. In some cases, methods of treatment and uses comprise administration of exosome compositions that are diluted and ready to be administered by the individual. In some cases, methods of treatment and uses comprise administration of exosome compositions that are contained in single use vials or syringes. In some cases, methods of treatment and uses comprise administration of a dose from a container comprising multiple doses.

Methods of treatment and uses disclosed herein comprise administration of SDC2+ and SDC2+CD39+ exosome compositions such as paracrine signaling SDC2+ and SDC2+CD39+ exosome compositions comprising proteins with or without therapeutic efficacy. Proteins include but are not limited to IL-12, suppressor of cytokine signaling (SOCS), p53, PTEN, CD52, TSC1, FOXP3, Soluble Immune Response Suppressor (SIRS), TGFB, CD39, CD39L3, CD73, and Maspin. Some methods and uses comprise administration of an enzyme having ATPase, ADPase, AMPase, or adenosine depurinase activity.

Methods of treatment and uses herein, in some cases, comprise administration of a therapeutically active SDC2+ and SDC2+CD39+ stromal stem cell or SDC2+ and SDC2+CD39+ exosome composition such as paracrine signaling SDC2+ and SDC2+CD39+ stromal stem cell or SDC2+ and SDC2+CD39+ exosome composition that comprises an immunosuppressive drug. Non-limiting examples of immunosuppressive drugs used in SDC2+ and SDC2+CD39+ stromal stem cell or SDC2+ and SDC2+CD39+ exosome compositions for treatment include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. SDC2+ and SDC2+CD39+ stromal stem cell or SDC2+ and SDC2+CD39+ exosome compositions for methods of treatment and uses comprise anti-TNF antibodies, including but not limited to infliximab, adalimumab, certolizumab, and golimumab. Methods of treatment and uses comprise administration of SDC2+ and SDC2+CD39+ stromal stem cell or SDC2+ and SDC2+CD39+ exosome compositions that comprise TNF inhibitors including but not limited to etanercept, xanthine derivatives, and bupropion. SDC2+ and SDC2+CD39+ stromal stem cell or SDC2+ and SDC2+CD39+ exosome compositions for methods of treatment and uses herein, in some cases, comprise NSAIDs. In some cases SDC2+ and SDC2+CD39+ stromal stem cell or SDC2+ and SDC2+CD39+ exosome compositions for methods of treatment and uses comprise one or more steroids.

Inflammatory diseases and disorders of the immune system result because of an over activation or inappropriate activation of the immune system. One or more cell types in the immune system may contribute to inflammatory and immune disease, for example CD4+ helper T cells, CD8+ cytotoxic T cells, Th17 cells, dendritic cells, macrophages, mast cells, leukocytes, neutrophils, eosinophils, basophils, monocytes, and combinations thereof. Often these cells synergize and amplify the inflammatory response through cell derived mediators such as enzymes, cytokines, chemokines, and other immune mediators. Immune mediators include but are not limited to lysosome granules, histamine, IFNγ, IL-8, leukotriene B4, nitric oxide, prostaglandins, TNFα, IL-1, IL-1β, IL-17, IL-2, and combinations thereof. Acute inflammation is a necessary component of the immune response to disease; however, chronic inflammation generally leads to inflammatory disease resulting in tissue destruction by inflammatory cells. In some cases, inflammation is caused, at least in part, by increased extracellular ATP at the site of inflammation. In some cases, SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein, reduce extracellular ATP thereby reducing inflammation. In some cases, inflammation is caused, at least in part, by increased extracellular ADP at the site of inflammation. In some cases, SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein, reduce extracellular ADP thereby reducing inflammation. In some cases, inflammation is caused, at least in part, by increased extracellular AMP at the site of inflammation. In some cases, SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein, reduce extracellular AMP thereby reducing inflammation. In some cases, inflammation is caused, at least in part, by increased extracellular adenosine at the site of inflammation. In some cases, SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein, reduce extracellular adenosine thereby reducing inflammation. In some cases, SDC2+ and SDC2+CD39+ stromal stem cell or SDC2+ and SDC2+CD39+ exosome compositions, such as paracrine signaling compositions reduce inflammation by delivery of at least one enzyme having ATPase, ADPase, AMPase, or adenosine depurinase activity. In some cases, SDC2+ and SDC2+CD39+ stromal stem cell or SDC2+ and SDC2+CD39+ exosome compositions, such as paracrine signaling compositions reduce inflammation by delivery of at least one of or both of the CD39 and CD73 enzymes, or structural or functional analogues thereof differing in sequence, length or sequence and length, but retaining a collective ability to reduce ATP or ADP to the free purine adenosine in the extracellular space. While inflammatory diseases present with a variety of symptoms that depend on the tissue or organ affected by inflammation, some commonalities include pain, heat, redness, swelling, and loss of tissue or organ function. In some cases, SDC2+ and SDC2+CD39+ stromal stem cell or SDC2+ and SDC2+CD39+ exosome compositions prevent or reverse all or some of the above inflammatory responses.

Disclosed herein are methods of modulation of an inflammatory response in a mammal using SDC2+ and SDC2+CD39+ stromal stem cell or SDC2+ and SDC2+CD39+ exosome compositions. Also disclosed are SDC2+ and SDC2+CD39+ stromal stem cell or SDC2+ and SDC2+CD39+ exosome compositions for use in modulation of an inflammatory response in a mammal. Also disclosed are SDC2+ and SDC2+CD39+ stromal stem cell or SDC2+ and SDC2+CD39+ exosome compositions for use in preparation of a medicament for modulation of an inflammatory response in a mammal. An inflammatory response, in some cases, is an immune response. In some cases, an inflammatory response is an autoimmune response. Immune responses, inflammatory responses, and autoimmune responses, often lead to the development of diseases or disorders in need of treatment in a mammal. Diseases and disorders caused by an immune response, inflammatory response, or autoimmune response affect nearly every tissue of the body and are generally characterized by an overactive or otherwise inappropriate response by the immune system of a mammal. In some cases, the immune response, inflammatory response, or autoimmune response is from the adaptive immune system. In some cases, the immune response, inflammatory response, or autoimmune response is from the innate immune response. In some cases, the immune response, inflammatory response, or autoimmune response results in excess secretion of cytokines, cytotoxic T cell activity, antibody production, T cell proliferation, swelling, redness, fever, edema, or other response by a cell or tissue of the immune system. In some cases the immune response is mediated or alleviated by administration of an SDC2+ and SDC2+CD39+ stromal stem cell or SDC2+ and SDC2+ CD39+ exosome composition such as a paracrine signaling SDC2+ and SDC2+CD39+ stromal stem cell or SDC2+ and SDC2+CD39+ exosome composition.

Disclosed herein are methods of treatment of an inflammation response or immune response comprising administration of an SDC2+ and SDC2+CD39+ stromal stem cell or SDC2+ and SDC2+CD39+ exosome composition. Also disclosed herein are SDC2+ and SDC2+CD39+ stromal stem cell or SDC2+ and SDC2+CD39+ exosome compositions for use in treatment of an inflammation response or immune response. Also disclosed herein are SDC2+ and SDC2+ CD39+ stromal stem cell or SDC2+ and SDC2+CD39+ exosome compositions for use in preparation of a medicament for treatment of an inflammation response or immune response. The response includes but is not limited to sepsis, acute respiratory distress syndrome (ARDS), Crohn's disease, inflammatory bowel syndrome, rheumatoid arthritis, osteoarthritis, graft versus host disease, multiple sclerosis, amyotrophic lateral sclerosis, motor neuron disorders, Sjogren's syndrome, non-healing dermal wounds, bone fractures, concussion wounds, burns, cachexia, sarcophenia, Dermatomyositis, Fibromyalgia, Inclusion body myositis, Myositis, Myasthenia gravis, Neuromyotonia, Paraneoplastic cerebellar degeneration, Polymyositis, and combinations thereof. In some cases, the inflammatory response comprises an inflammatory liver disease. In some cases the inflammation response is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

An inflammatory response in need of treatment using SDC2+ and SDC2+CD39+ stromal stem cell or SDC2+ and SDC2+CD39+ exosome compositions disclosed herein, in some cases, comprises a diabetic complication. Diabetic complications are often seen in individuals with diabetes. In some cases, the diabetic complications occur in individuals with type 1 diabetes. In some cases, the diabetic complications occur in individuals with type 2 diabetes. Diabetic complications include, but are not limited to atherosclerosis, nephropathy, cardiomyopathy, neuropathy, a kidney disorder, kidney failure, diabetic ulcers, leg ulcers, and other conditions occurring in patients with diabetes. In some cases the diabetic complication is mediated or alleviated by administration of a SDC2+ and SDC2+CD39+ stromal stem cell or SDC2+ and SDC2+CD39+ exosome composition such as a paracrine signaling SDC2+ and SDC2+CD39+ stromal stem cell or and SDC2+CD39+ SDC2+ and SDC2+ CD39+ exosome composition. Upon SDC2+ and SDC2+ CD39+ stromal stem cell or SDC2+ and SDC2+CD39+ exosome administration, symptoms of the diabetic condition are ameliorated, such that some function is regained in some cases. Often, these benefits are observed in diabetic individuals without impacting blood glucose levels.

SDC2+ and SDC2+CD39+ stromal stem cell or SDC2+ and SDC2+CD39+ exosome compositions disclosed herein, in some cases, are useful for treating or alleviating type 2 diabetes, also known as noninsulin-dependent diabetes mellitus or adult onset diabetes. Type 2 diabetes is associated with increased systemic inflammation which reduces sensitivity to insulin in patients with type 2 diabetes. In some cases, systemic inflammation is associated with obesity, heart disease, atherosclerosis and metabolic syndrome. Symptoms of type 2 diabetes include but are not limited to fatigue, hunger, non-healing sores, heart disease, stroke, diabetic retinopathy, blindness, kidney failure, reduced blood flow, hyperosmolar hyperglycemia, and combinations thereof. Reduction of inflammation, by anti-inflammatory drugs or compositions, such as SDC2+ and SDC2+CD39+ stromal stem cell or SDC2+ and SDC2+CD39+ exosome compositions disclosed herein, reduce one or more symptoms and in some cases cure type 2 diabetes. In particular, SDC2+ and SDC2+CD39+ stromal stem cell or SDC2+ and SDC2+CD39+ exosome administration in some cases ameliorates diabetes-associated kidney damage, in some cases without impacting glucose levels in the exosome recipient.

In some cases, an inflammatory response in need of treatment using SDC2+ and SDC2+CD39+ stromal stem cell or SDC2+ and SDC2+CD39+ exosome compositions disclosed herein comprises a heart disorder. Heart disorders include but are not limited to myocarditis, postmyocardial infarction syndrome, postperiocardiotomy syndrome, and subacute bacterial endocarditis. In some cases the heart disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

In some cases, an inflammatory response in need of treatment using SDC2+ and SDC2+CD39+ stromal stem cell or SDC2+ and SDC2+CD39+ exosome compositions disclosed herein comprises a kidney disorder. Kidney disorders include but are not limited to anti-glomerular basement membrane nephritis, interstitial cystitis, and lupus nephritis. Some kidney disorders result from or are associated with diabetes such as type 1 diabetes or type 2 diabetes. In some cases the kidney disorder is treated, mediated or alleviated by administration of an SDC2+ and SDC2+ CD39+ stromal stem cell or SDC2+ and SDC2+CD39+ exosome composition. An example of an SDC2+ and SDC2+CD39+ stromal stem cell or SDC2+ and SDC2+ CD39+ exosome composition mediating a kidney disorder is a paracrine signaling SDC2+ and SDC2+CD39+ stromal stem cell or SDC2+ and SDC2+CD39+ exosome composition. Upon SDC2+ and SDC2+CD39+ stromal stem cell or SDC2+ and SDC2+CD39+ exosome administration, symptoms of the kidney condition are ameliorated, such that some kidney function is regained in some cases. Often, these benefits are observed in diabetic individuals without impacting blood glucose levels.

Some inflammatory responses in need of treatment using SDC2+ and SDC2+CD39+ stromal stem cell or SDC2+ and SDC2+CD39+ exosome compositions herein comprise a liver disorder. Liver disorders include but are not limited to autoimmune hepatitis, Primary biliary cirrhosis, and Primary sclerosing cholangitis. In some cases the liver disorder is mediated or alleviated by administration of an SDC2+ and SDC2+CD39+ stromal stem cell or SDC2+ and SDC2+ CD39+ exosome composition such as a paracrine signaling SDC2+ and SDC2+CD39+ stromal stem cell or SDC2+ and SDC2+CD39+ exosome composition.

In some cases, an inflammatory response in need of treatment using SDC2+ and SDC2+CD39+ stromal stem cell or SDC2+ and SDC2+CD39+ exosome compositions disclosed herein comprises a lung disorder. Lung disorders include but are not limited to acute respiratory distress syndrome (ARDS), Antisynthetase syndrome, asthma, chronic obstructive pulmonary disease, cystic fibrosis, atelectasis, bronchitis, emphysema, pneumonia, and pulmonary edema. In some cases the lung disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

In some cases, an inflammatory response in need of treatment using SDC2+ and SDC2+CD39+ stromal stem cell or SDC2+ and SDC2+CD39+ exosome compositions disclosed herein comprises a skin disorder. Skin disorders include but are not limited to Alopecia Areata, Autoimmune Angioedema, autoimmune progesterone dermatitis, autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, autoimmune polyendocrine syndrome, autoimmune polyendocrine syndrome type 2, and autoimmune polyendocrine syndrome type 3. In some cases the skin disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

Some inflammatory responses in need of treatment using SDC2+ and SDC2+CD39+ stromal stem cell or SDC2+ and SDC2+CD39+ exosome compositions herein, comprise a pancreas disorder. Pancreas disorders include but are not limited to autoimmune pancreatitis and diabetes mellitus type 1. In some cases the pancreatic disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

SDC2+ and SDC2+CD39+ stromal stem cell or SDC2+ and SDC2+CD39+ exosome compositions disclosed herein, in some cases, are useful in treating or alleviating Diabetes mellitus type 1, also known as type 1 diabetes. Diabetes mellitus type 1 is caused by destruction of insulin secreting beta cells in the pancreas, at least in part, by autoreactive T cells. Symptoms of Diabetes mellitus type 1 include but are not limited to increased blood and urine glucose levels, polyuria (frequent urination), polydipsia (increased thirst), polyphagia (increased hunger), weight loss, diabetic ketoacidosis, nonketoic hyperosmolar coma, heart disease, stroke, kidney failure, foot ulcers, eye damage, and combinations thereof. In the latent autoimmune or early stage of diabetes, immunosuppression or reduction of the immune response, by anti-inflammatory drugs or compositions, such as SDC2+ and SDC2+CD39+ stromal stem cell or SDC2+ and SDC2+CD39+ exosome compositions disclosed herein, reverse, slow, and prevent increased destruction of the beta cells, leading to a reduction in one or more symptoms, and in some cases, a cure of the diabetes mellitus type 1. In particular, administration of an SDC2+ and SDC2+CD39+ stromal stem cell or SDC2+ and SDC2+CD39+ exosome composition in some cases treats, mediates, or ameliorates the symptoms of type 1 diabetes-related kidney disorders. In some cases this beneficial effect of SDC2+ and SDC2+CD39+ stromal stem cell or SDC2+ and SDC2+CD39+ exosome administration is independent of any impact on glucose levels of SDC2+ and SDC2+CD39+ stromal stem cell or SDC2+ and SDC2+CD39+ exosome administration.

In some cases, an inflammatory response in need of treatment using SDC2+ and SDC2+CD39+ stromal stem cell or SDC2+ and SDC2+CD39+ exosome compositions disclosed herein, comprises a thyroid disorder. Thyroid disorders include but are not limited to autoimmune thyroiditis, Ord's thyroiditis and Graves' disease. In some cases the thyroid disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

In some cases, an inflammatory response in need of treatment using SDC2+ and SDC2+CD39+ stromal stem cell or SDC2+ and SDC2+CD39+ exosome compositions disclosed herein, comprises an exocrine disorder. Exocrine disorders include but are not limited to a reproductive organ disorder, autoimmune oophoritis, endometriosis, and autoimmune orchitis. In some cases the exocrine disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

In some cases, an inflammatory response in need of treatment using SDC2+ and SDC2+CD39+ stromal stem cell or SDC2+ and SDC2+CD39+ exosome compositions disclosed herein, comprises a digestive system disorder. Digestive disorders include but are not limited to autoimmune enteropathy, Celiac disease, Crohn's disease, microscopic colitis, inflammatory bowel disease, and ulcerative colitis. In some cases the digestive system disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

Some inflammatory responses in need of treatment using SDC2+ and SDC2+CD39+ stromal stem cell or SDC2+ and SDC2+CD39+ exosome compositions herein, comprise a blood disorder. Blood disorders include but are not limited to antiphospholipid syndrome, aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, and Thrombocytopenia. Often, the blood disorder is mediated or alleviated by administration of an SDC2+ and SDC2+CD39+ stromal stem cell or SDC2+ and SDC2+CD39+ exosome composition, such as a paracrine signaling SDC2+ and SDC2+CD39+ stromal stem cell or SDC2+ and SDC2+CD39+ exosome composition.

Often, an inflammatory response in need of treatment using SDC2+ and SDC2+CD39+ stromal stem cell or SDC2+ and SDC2+CD39+ exosome compositions disclosed herein comprises a connective tissue, multi-organ or systemic disorder. Connective tissue, multi-organ, or systemic disorders include but are not limited to adiposis dolorosa, Adult-onset Still's disease, Ankylosing Spondylitis, CREST syndrome, Drug-induced lupus, enthesitis-related arthritis, Eosinophilic fasciitis, Felty syndrome, juvenile Arthritis, Lyme disease (Chronic), mixed connective tissue disease, palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, schnitzler syndrome, Systemic Lupus Erythematosus, and undifferentiated connective tissue disease. In some cases the connective tissue, multi-organ or systemic disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

In some cases, an inflammatory response in need of treatment using SDC2+ and SDC2+CD39+ stromal stem cell or SDC2+ and SDC2+CD39+ exosome compositions disclosed herein, comprises a nervous system disorder. Nervous system disorders include but are not limited to acute disseminated encephalomyelitis, acute motor axonal neuropathy, anti-N-methyl-D-aspartate receptor encephalitis, Balo concentric sclerosis, Bickerstaff's encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis, pediatric autoimmune neuropsychiatric disorder associated with Streptococcus, progressive inflammatory neuropathy, restless leg syndrome, Stiff person syndrome, Sydenham chorea, Alzheimer's disease, Parkinson's disease, ALS, and transverse myelitis. In some cases, the nervous system disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition. In some cases, the nervous system disorder is a central nervous system disorder. In some cases, administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition disclosed herein results in exosomes or other factors crossing the blood brain barrier thereby reducing inflammation in the brain.

Some inflammatory responses in need of treatment using SDC2+ and SDC2+CD39+ stromal stem cell or SDC2+ and SDC2+CD39+ exosome compositions herein, comprise an eye disorder. Eye disorders include but are not limited to autoimmune retinopathy, autoimmune uveitis, Cogan syndrome, Graves's ophthalmopathy, intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, and Tolosa-Hunt syndrome. Often the eye disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

Additional inflammatory responses in need of treatment using SDC2+ and SDC2+CD39+ stromal stem cell or SDC2+ and SDC2+CD39+ exosome compositions herein, comprises an ear disorder. Ear disorders include but are not limited to autoimmune inner ear disease and Meniere's disease. In some cases the ear disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

In some cases, an inflammatory response in need of treatment using SDC2+ and SDC2+CD39+ stromal stem cell or SDC2+ and SDC2+CD39+ exosome compositions disclosed herein, comprises a vascular system disorder. Vascular system disorders include but are not limited to Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, and Vasculitis. In some cases the vascular system disorder is mediated or alleviated by administration of an SDC2+ and SDC2+CD39+ stromal stem cell or SDC2+ and SDC2+CD39+ exosome composition such as a paracrine signaling SDC2+ and SDC2+CD39+ stromal stem cell or SDC2+ and SDC2+CD39+ exosome composition.

Methods of treatment and uses disclosed herein comprise identification of a patient or a group of patients for treatment by administration of SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions. Identification of a patient group, in some cases, is done by a physician or other healthcare professional. The physician or other healthcare professional uses criteria known by those in the medical field to determine whether an individual, patient, or group of patients is a candidate for treatment of an inflammation, immune or autoimmune response.

Methods of Delivery

SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions, purified based on expression of CD39, as described herein, are used in methods of delivery of immuno-modulatory signals to the intracellular space of a mammal. SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions, as described herein, are also for use in delivery of immuno-modulatory signals to the intracellular space of a mammal. Immuno-modulatory signals comprise compositions that modulate the inflammatory or immune response in a mammal. In some cases, the exosome composition is isolated or purified from a stromal cell, a SDC2+ cell, mesenchymal stem cell, or a SDC2+ mesenchymal stem cell, wherein cells are purified based on expression of CD39. The exosome composition contains the immuno-modulatory signal thereby delivering the immuno-modulatory signal to the intracellular space of the mammal when administered to the mammal without exposing the contents of the exosome composition to the humoral immune system of the mammal.

Once administered, delivery of the SDC2+ and SDC2+CD39+ stromal stem cell or SDC2+ and SDC2+CD39+ exosome composition such as paracrine signaling SDC2+ and SDC2+CD39+ stromal stem cell or SDC2+ and SDC2+CD39+ exosome composition to the intracellular space of the mammal occurs though processes including but not limited to phagocytosis, endocytosis, or fusion. The SDC2+ and SDC2+CD39+ stromal stem cell or SDC2+ and SDC2+CD39+ exosome composition is administered to the mammal in need of immuno-modulatory signaling by suitable routes of administration, appropriate to the need of the mammal. Routes of administration include but are not limited to parenteral (including subcutaneous, intravenous, intra-arterial, intraosseous, intracerebral, intracerebroventricular, intrathecal, intramedullary, intraarticular, intramuscular, or intraperitoneal injection), rectal, respiratory or inhalation, topical, transdermal, or oral (for example, in capsules, suspensions, or tablets).

Methods and uses of delivery use SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein that are formulated in a physiologically acceptable buffer and at least one excipient. Non-limiting examples of excipients include sucrose, trehalose, polyethylene glycol, a polysaccharide, a carrier protein, an inert protein, dextran, hydroxyl ethyl starch (BETA), PEG-4000, gelatin, PLGA, Eudragit RS 100 Nanoparticles, and combinations thereof. Such SDC2+ and SDC2+CD39+ stromal stem cell or SDC2+ and SDC2+CD39+ exosome compositions are stored at a temperature determined to be most stable (i.e., wherein the SDC2+ and SDC2+CD39+ stromal stem cell or SDC2+ and SDC2+CD39+ exosome composition retains highest potency). In some cases, addition of one or more excipients allows the composition to retain potency when stored at a higher temperature than otherwise would be possible.

Methods and uses of delivery of SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein include compositions that comprise mixtures of SDC2+ and SDC2+CD39+ exosomes and SDC2+ mesenchymal stem cells (e.g., SDC2+ mesenchymal stromal stem cells). In some instances, SDC2+ and SDC2+CD39+ stromal stem cell or SDC2+ and SDC2+CD39+ exosome compositions include compositions comprising in vitro SDC2+ and SDC2+CD39+ stromal stem cell or SDC2+ and SDC2+CD39+ exosomes and regulatory T cells. Regulatory T cells include CD25+ regulatory T cells, CD4+ regulatory T cells, FoxP3+ regulatory T cells, CD25+CD4+FoxP3+ regulatory T cells, and combinations thereof. In some instances, SDC2+ and SDC2+CD39+ stromal stem cell or SDC2+ and SDC2+CD39+ exosome compositions include compositions comprising in vitro exosomes, SDC2+ mesenchymal stem cells (e.g., SDC2+ mesenchymal stromal stem cells), and regulatory T cells.

Stromal cell compositions for methods of delivery herein, in some cases, are modified to increase the therapeutic efficacy of the stromal stem cell composition. In some cases, cells are genetically modified to overexpress CD39. In some cases, cells are genetically modified to overexpress CD39L3. In some cases, cells are genetically modified to overexpress an apyrase as disclosed herein, such as CD39, a structural or functionally active variant of CD39 or other protein having apyrase activity. Genetic modification of stromal cells is accomplished by methods including but is not limited to transfection of the stromal cells with one or more plasmids that comprise the CD39 or CD39L3 coding sequence and a promoter, such as a CMV, SV40, EF1a, or CAG promoter. Genetic modification of stromal cells, in some cases, is accomplished by infection of the stromal cells with a virus that comprises the CD39 or CD39L3 coding sequence and a promoter.

Methods and uses of delivery comprise administration of compositions comprising SDC2+ and SDC2+CD39+ stromal stem cells isolated based on expression of CD39 in a therapeutically effective amount. Administration of a therapeutically effective amount of SDC2+ and SDC2+CD39+ stromal stem cells, in some cases, comprises administration of $10^3$ to $10^8$ SDC2+ and SDC2+CD39+ stromal stem cells, for example $10^3$, $10^4$, $10^5$, $10^6$, $10^7$, $10^8$, or more SDC2+ and SDC2+CD39+ stromal stem cells of the composition. Methods and uses of delivery include administration of SDC2+ and SDC2+CD39+ stromal stem cells compositions, which in some cases, are concentrated to be diluted by the individual or health care provider prior to administration. In some cases, methods and uses of delivery comprise administration of SDC2+ and SDC2+CD39+ stromal stem cells compositions that are diluted and ready to be administered by the individual or health care provider. In some cases, methods and uses of delivery comprise administration of SDC2+ and SDC2+CD39+ stromal stem cells compositions that are contained in single use vials, syringes, or IV bags. In some cases, methods and uses of delivery comprise administration of a dose from a container comprising multiple doses.

Methods and uses of delivery comprise administration of exosome compositions such as paracrine signaling exosome compositions in a therapeutically effective amount. A therapeutically effective amount of exosomes, in some cases, ranges from $10^6$-$10^8$ exosomes, for example $10^6$, $10^7$, $10^8$, or more exosomes in the composition. In some cases, a therapeutically effective amount of exosomes ranges from 1 µg to 700 mg of exosomes, for example 1 µg, 10 µg, 20 µg, 50 µg, 100 µg, 150 µg, 200 µg, 250 µg, 500 µg, 750 µg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Exosome compositions, in some cases, are concentrated to be diluted by the individual prior to administration. In some cases, exosome compositions are diluted and ready to be administered by the individual. In some cases, exosome compositions are contained in single use vials or syringes. In some cases, multiple doses are present in a single container.

Methods and uses of delivery use SDC2+ and SDC2+CD39+ exosome compositions such as paracrine signaling SDC2+ and SDC2+CD39+ exosome compositions that comprise proteins with or without therapeutic efficacy. Proteins include but are not limited to IL-12, suppressor of cytokine signaling (SOCS), p53, PTEN, CD52, TSC1, FOXP3, Soluble Immune Response Suppressor (SIRS), TGFB, CD39, CD39L3, CD73, and Maspin.

Methods and uses of delivery to an intracellular space include SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions topically (e.g., applied directly to the skin of the individual being treated). In some cases, topical administration is used to treat diseases of the skin. Topical administration includes epicutaneous administration. SDC2+ and SDC2+CD39+ stromal stem cell or SDC2+ and SDC2+CD39+ exosome compositions for topical administration are formulated specifically to be administered to the skin. Such topical SDC2+ and SDC2+CD39+ stromal stem cell or SDC2+ and SDC2+CD39+ exosome compositions include but are not limited to solutions, lotions, creams, ointments, gels (including hydrogels or collagen gels), foams, transdermal patches, powders, pastes, and tinctures. In some cases, SDC2+ and SDC2+

CD39+ stromal stem cell or SDC2+ and SDC2+CD39+ exosome compositions comprise a hydrogel or a collagen gel.

Methods and uses of delivery to an intracellular space include administration of SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions to the eye (e.g., intraocular or ophthalmic). SDC2+ and SDC2+CD39+ stromal stem cell or SDC2+ and SDC2+CD39+ exosome compositions for administration to the eye comprise formulations (e.g., buffers or excipients) suitable for administration to the eye.

Methods and uses of delivery to an intracellular space include administration by injection. Injection of SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions to a subject is effective in treating certain indications, diseases, or disorders. Delivery of an SDC2+ and SDC2+CD39+ stromal stem cell or SDC2+ and SDC2+CD39+ exosome composition via injection includes but is not limited to injection to the lymph nodes, subcutaneous injection, intramuscular injection, intravenous injection, intraperitoneal injection, intrathecal injection, intradermal injection, intraarticular injection, and other suitable injection methods. SDC2+ and SDC2+CD39+ stromal stem cell or SDC2+ and SDC2+CD39+ exosome compositions for injection comprise formulations or physiologically acceptable buffers or excipients for injection.

Methods and uses of delivery to an intracellular space include administration of SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions disclosed herein via a respiratory or inhalation route using an inhalation device. An inhalation device is capable of administering therapeutic compositions to the respiratory airways of a patient. Inhalation devices include conventional inhalation devices such as metered dose inhalers, dry powder inhalers, jet nebulizers, ultrasonic wave nebulizers, heat vaporizers, soft mist inhalers, and high efficiency nebulizers. Nebulizers, metered dose inhalers, and soft mist inhalers deliver therapeutics by forming an aerosol which includes droplet sizes that can easily be inhaled. The aerosol can be used by a patient within the bounds of an inhalation therapy. A nebulizer is able to turn a therapeutic or medication into a fine aerosol mist that is delivered to the lungs of an individual.

Methods and uses of delivery to an intracellular space include use of SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions comprising an immunosuppressive drug. Non-limiting examples of immunosuppressive drugs include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. SDC2+ and SDC2+CD39+ stromal stem cell or SDC2+ and SDC2+CD39+ exosome compositions comprise anti-TNF antibodies, including but not limited to infliximab, adalimumab, certolizumab, and golimumab. SDC2+ and SDC2+CD39+ stromal stem cell or SDC2+ and SDC2+CD39+ exosome compositions comprise TNF inhibitors including but not limited to etanercept, xanthine derivatives, and bupropion. In some cases, SDC2+ and SDC2+CD39+ stromal stem cell or SDC2+ and SDC2+CD39+ exosome compositions comprise one or more NSAIDs. In some cases, SDC2+ and SDC2+CD39+ stromal stem cell or SDC2+ and SDC2+CD39+ exosome compositions comprise one or more steroids.

Supplemented Stem Cell and Stromal Stem Cell Compositions

Disclosed herein are SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions comprising supplemented stem cell and stromal stem cell compositions, wherein SDC2+ and SDC2+CD39+ stromal stem cells are isolated based on expression of CD39. Supplemented stem cell and stromal stem cell compositions comprise cultured stem cells or stromal stem cells and at least one SDC2+ and SDC2+CD39+ stromal stem cell or SDC2+ and SDC2+CD39+ exosome composition disclosed herein. In some cases, the SDC2+ and SDC2+CD39+ stromal stem cell or SDC2+ and SDC2+CD39+ exosome composition is isolated from the cultured stem cells or stromal stem cells based on expression of CD39 and then combined with the cultured stem cells to enhance the therapeutic efficacy of the cultured stem cells.

Supplemented stem cell and stromal stem cell compositions comprise SDC2+ and SDC2+CD39+ stromal stem cell or SDC2+ and SDC2+CD39+ exosome compositions such as paracrine signaling SDC2+ and SDC2+CD39+ stromal stem cell or SDC2+ and SDC2+CD39+ exosome compositions, wherein the SDC2+ and SDC2+CD39+ stromal stem cells or SDC2+ and SDC2+CD39+ exosomes are isolated based on expression of CD39. In some compositions, at least 20% of the stromal stem cells or exosomes in the composition are SDC2+ or comprise SDC2. In some cases at least 20%, 30%, 40%, 50%, 60%, 70%, 80%, 90%, 95%, 99%, or more of the stromal stem cells or exosomes comprise SDC2. In some instances, SDC2 is found on the surface of the stromal stem cell or exosome or at least comprising a polypeptide portion that is found on the surface of the stromal stem cell or exosome. In some instances, SDC2 is found at the interior of the stromal stem cell or exosome. The proportion of SDC2+ stromal stem cell or SDC2+ and SDC2+CD39+ exosomes in the composition comprising SDC2 is determined by immunofluorescence, for example FACS, microscopy, or other suitable method.

Supplemented stem cell compositions herein, in some cases, comprise stromal stem cells modified to increase the therapeutic efficacy of the stromal stem cell composition. In some cases, cells are genetically modified to overexpress CD39. In some cases, cells are genetically modified to overexpress CD39L3. In some cases, cells are genetically modified to overexpress an apyrase as disclosed herein, such as CD39, a structural or functionally active variant of CD39 or other protein having apyrase activity. Genetic modification of stromal cells is accomplished by methods including but not limited to transfection of the stromal cells with one or more plasmids that comprise the CD39 or CD39L3 coding sequence and a promoter, such as a CMV, SV40, EF1a, or CAG promoter. Genetic modification of stromal cells, in some cases, is accomplished by infection of the stromal cells with a virus that comprises the CD39 or CD39L3 coding sequence and a promoter.

Supplemented stem cell compositions comprise cultured stem cells or stromal stem cells that in some cases are SDC2+. At least 20% of the cultured stem cells or stromal stem cells are SDC2+ in some cases. The cultured stem cell or stromal stem cell composition comprises, in some cases, 20% to 90% SDC2+ cells, for example 20%, 30%, 40%, 50%, 60%, 70%, 80%, 90% SDC+ cells or more than 90% SDC2 cells, up to and including a uniform population of 100% SDC2 positive cells.

Supplemented stem cell and stromal stem cell compositions in some cases, comprise SDC2+ and SDC2+CD39+ exosome compositions such as paracrine signaling SDC2+ and SDC2+CD39+ exosome compositions comprising proteins with or without therapeutic efficacy. Proteins include but are not limited to IL-12, suppressor of cytokine signaling (SOCS), p53, PTEN, CD52, TSC1, FOXP3, Soluble Immune Response Suppressor (SIRS), TGFB, CD39, CD39L3, CD73, and Maspin.

Supplemented stem cell and stromal stem cell compositions comprise, in some cases, an SDC2+ and SDC2+CD39+ exosome composition such as paracrine signaling SDC2+ and SDC2+CD39+ exosome composition comprising an immunosuppressive drug. Non-limiting examples of immunosuppressive drugs include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. Exosome compositions comprise anti-TNF antibodies, including but not limited to infliximab, adalimumab, certolizumab, and golimumab. Exosome compositions comprise TNF inhibitors including but not limited to etanercept, xanthine derivatives, and bupropion. In some cases, exosome compositions comprise one or more NSAIDs. In some cases, exosome compositions comprise at least one steroid.

Figure 1B:
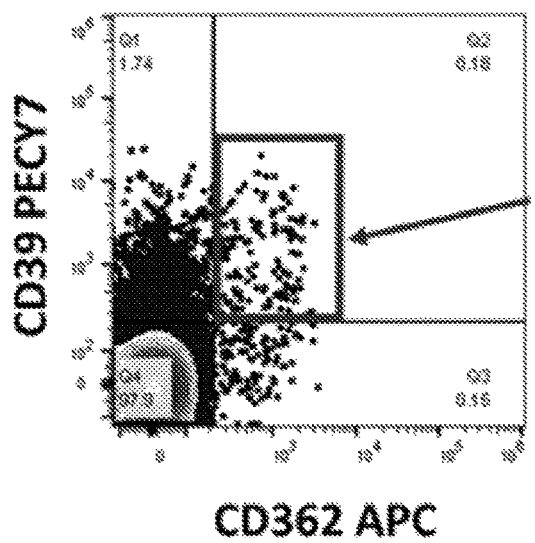
FIG. 1B shows an exemplary analysis of CD39 and CD362 (SDC2) expression in the studied umbilical cord cell population. Double positive cells are highlighted with a bolded box and an arrow.
Figure 1C:
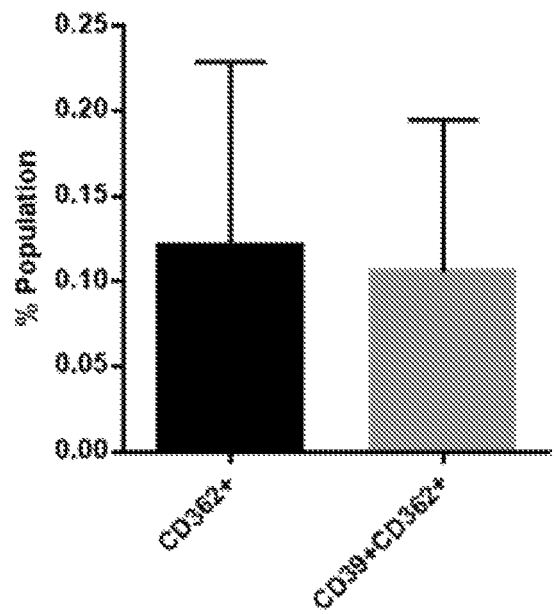
FIG. 1C shows relative population percentage of CD362+ versus CD39+/CD362+ cells.
Figure 1D:
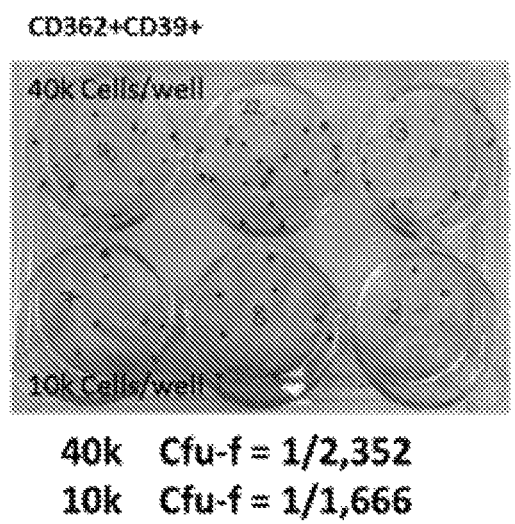
FIG. 1D shows an exemplary colony formation assay on CD362+/CD39+ cells.
Figure 1E:
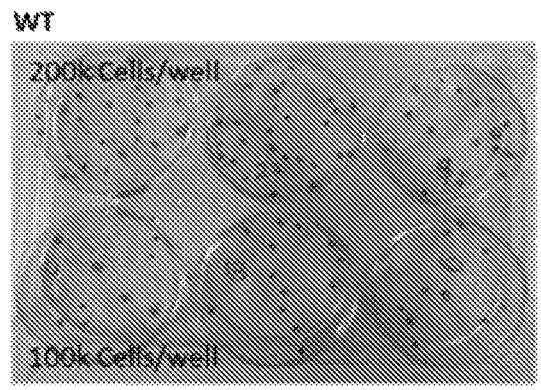
FIG. 1E shows an exemplary colony formation assay on unsorted (wildtype) cells.

Exosome compositions, methods of isolation, and methods and uses in treating disease are illustrated by the drawings provided herein. FIGS. 1A-1E show identification and isolation of novel CD39+CD362+ stromal cell population from human umbilical cord. FIG. 1A shows a representative gating strategy. FIG. 1B shows identification of CD39+CD362+ (highlighted in bolded square gate and arrow) stromal cell population. FIG. 1C shows CD362+ 0.121±0.054, CD39+CD362+ 0.105±0.045 (n=5% mean±SEM). FIG. 1D and FIG. 1E show CFU-f analysis and example of colonies formed from CD39+CD362+ sorted (FIG. 1D) and wildtype (FIG. 1E, WT unsorted) populations by Miltenyi MACSQuant Tyto microchip cell sorter, n=2.

FIGS. 2A-C show identification and isolation of novel CD39+CD362+ stromal cell population from human bone marrow. FIG. 2A shows a representative gating controls and identification of CD39+CD362+ (highlighted in bolded square gate) stromal cell populations. FIG. 2B shows CD362+ 0.4093±0.103, CD39+CD362+ 0.0147±0.002, (n=3% mean±SEM). FIG. 2C shows CFU-f analysis of colonies formed from wildtype (WT unsorted), CD362+, CD39+CD362+, CD39+ and double negative (−/−) populations by BD FACSAria cell sorter, n=3.

Figures 3A, 3B:
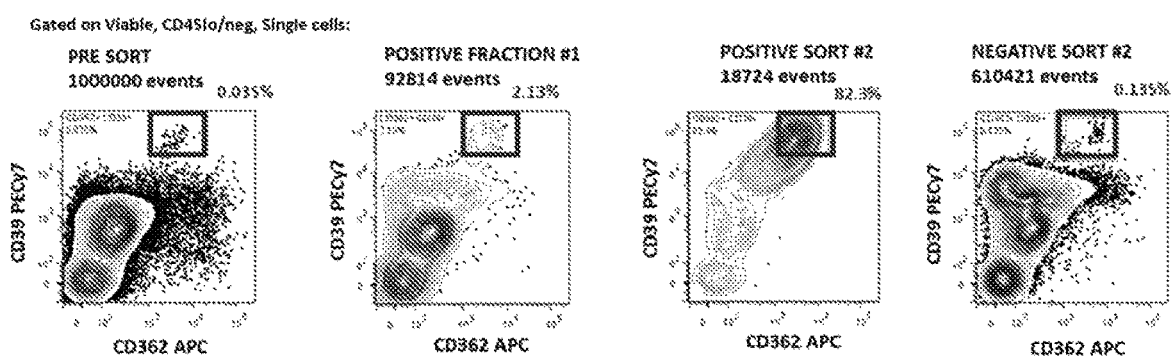
FIG. 3A shows a representative Miltenyi MACSQuant Tyto sort gate and analysis for identification of CD39+/CD362+ cells from human bone marrow (highlighted in bold squares).
FIG. 3B shows tabular results of colony formation assay for unsorted cells, CD39−/CD362+ cells, CD39+/CD362+ cells, CD39hi/CD362+, CD39+/CD362− cells, and double negative cells using both the Miltenyi MACSQuant Tyto sort and BD FACSAria cell sorters from human bone marrow.

FIGS. 3A-B show identification and isolation of novel CD271+CD362+ stromal cell population from human bone marrow using a novel closed microchip cell sorter Miltenyi Tyto. FIG. 3A shows a representative Miltenyi MACSQuant Tyto sort gate and post sort analysis gating strategy for identification of CD39+CD362+ (highlighted in bolded square gate) stromal cell population, n=1. FIG. 3B shows CFU-f analysis and example of colonies formed from CD39+CD362+ populations isolated by BD FACSAria cell sorter (n=3) and Miltenyi MACSQuant Tyto microchip cell sorter, (n=1).

Figure 4:
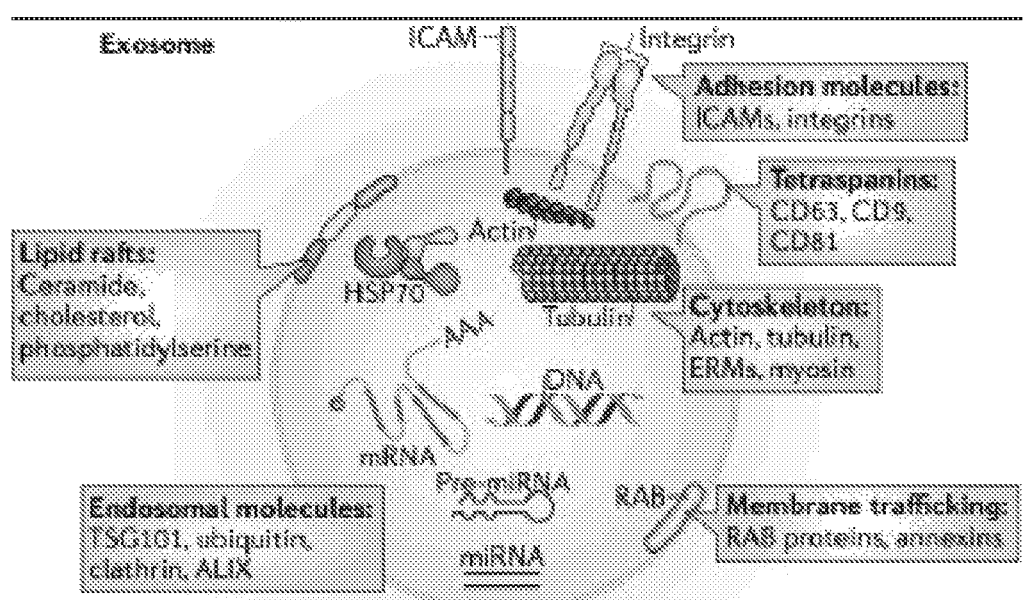
FIG. 4 illustrates exosome synthesis, release and uptake by an adjacent cell.

FIG. 4 provides a cartoon depiction of an exosome as contemplated herein. In this drawing, a number of components important to some exosomes are shown including adhesion molecules such as ICAMs and integrins; tetraspanins such as CD63, CD9, and CD81; cytoskeleton proteins such as actin, tubulin ERMs, and myosin; membrane trafficking proteins such as RABs and annexins; endosomal molecules such as TSG101, ubiquitin, clatherin, and ALIX; and lipid rafts including ceramide, cholesterol, and phosphatidylserine; nucleic acids such as mRNA molecules, for example mRNA molecules encoding a protein or proteins of interest, DNA fragments or entire DNA coding molecules of various lengths up to and including DNA molecules harboring multiple coding loci, miRNA or pre-miRNA, such as miRNA or pre-miRNA impacting he expression of a gene or transcript encoding a protein involved in an immune response. None, any or all of these components, up to and including various permutations or combinations up to all of these components or variants of one or more of these components, are present in some various SDC2+ exosomes as contemplated herein.

Figure 5:
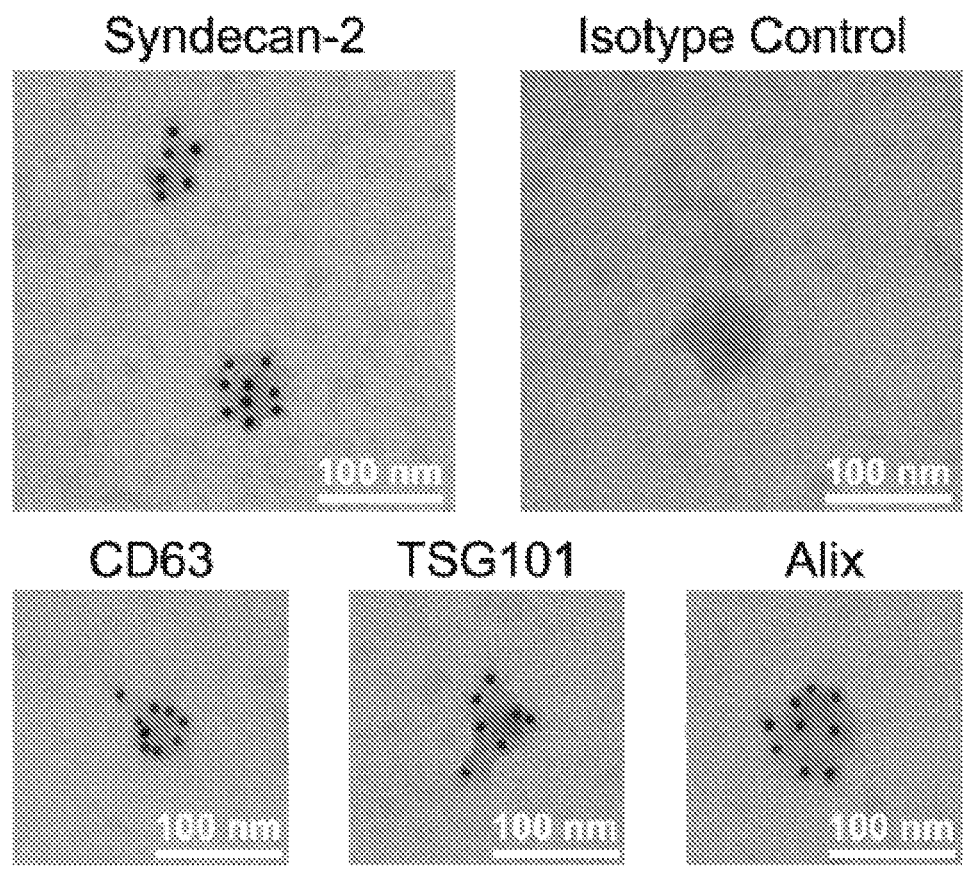
FIG. 5 shows SDC2 expression by exosomes derived from SDC2+ mesenchymal stromal cells (MSC) by transmission electron microscopy.

FIG. 5 shows SDC2 presence in exosomes derived from SDC2+ mesenchymal stromal cells (MSC) by transmission electron microscopy to detect gold-tagged anti-SDC2 antibody binding. Expression of CD63, TSG101 and Alix is similarly shown by transmission electron microscopy of metal-labeled antibodies to the respective proteins. The scale bar in each photomicrograph is 100 nm. The figure demonstrates that SDC2, CD63, TSG101 and Alix are present in the exosomes isolated from SDC2+ mesenchymal stem cells. The isotype control demonstrates that the antibodies bind specifically. The lack of Exosome labeling with a rat IgG2B APC-conjugated Isotype Control antibody (Cat #IC013A from R&D Systems) indicates the specificity of the anti-SDC2 labeling with an equivalent rat IgG2B APC-conjugated anti-SDC2 antibody.

Figure 6:
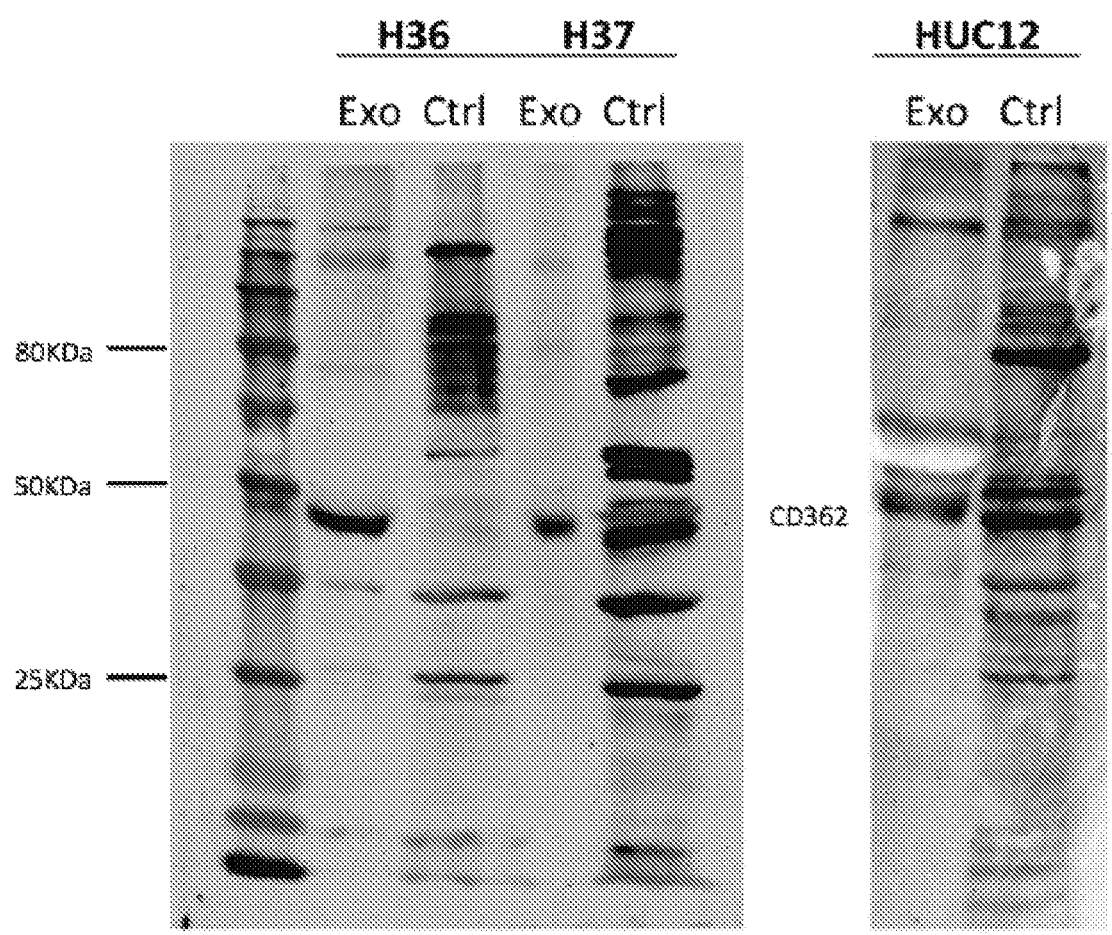
FIG. 6 shows SDC2 expression by exosomes derived from SDC2+ mesenchymal stromal cells (MSC) by Western blot.

FIG. 6 shows SDC2 expression in exosomes derived from SDC2+ mesenchymal stromal cells (MSC) by protein gel electrophoresis. In this experiment, H36 (marrow derived SDC2+ MSC), H37 (marrow derived SDC2+ MSC), and HUC12 (human umbilical cord derived SDC2+ MSC) cells and exosomes purified from those cells were homogenized in lysis buffer and run on an SDS-PAGE gel, along with unpurified whole sample protein extracts. Proteins from the gel were transferred to a membrane and stained with a rat IgG2B anti-human SDC2 antibody. In each 'exo' exosome protein extract lane, strong enrichment at below 50 kDa is observed, indicative of SDC2/CD362 being disproportionately present in the exosome fraction relative to the whole cell extract fraction.

SDC2+ exosomes were tested for their safety and efficacy to reduce inflammation-related damage in a mammalian model of inflammation damage.

Figure 7:
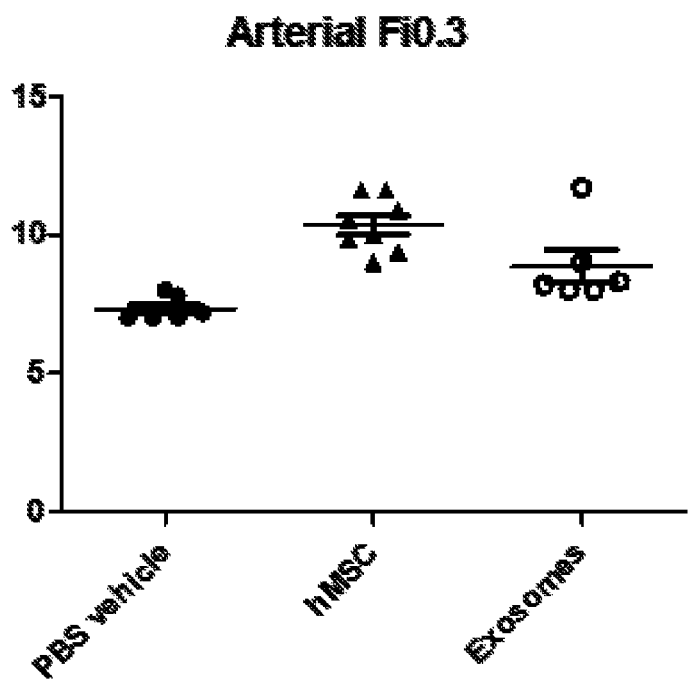
FIG. 7 shows arterial FI 0.3 in rats treated with PBS vehicle, human mesenchymal stem cells, or exosomes in a rat model of ARDS.

FIG. 7 shows arterial FI 0.3 in rats treated with phosphate buffered saline ('PBS') vehicle, human umbilical cord derived SDC2+ stromal cells, or exosomes in a rat model of acute respiratory distress syndrome ('ARDS'). In this experiment, 300 g Sprague Dawley rats were given an intrapulmonary dose of *E. coli* to induce ARDS lung injury. One hour later, the rats were treated with a 90-100 µg dose of exosomes or 4 million human mesenchymal stem cells (hMSC). The extent of lung injury was then measured 24 hours later by measurement of arterial oxygen at FI 0.3. This experiment shows that rats treated with only 90-100 µg of exosomes had improved lung function relative to those treated with PBS vehicle. It is expected that rats treated with a greater dose show increased improvement in lung function, such as at a level comparable to that of hMSC treatment.

Figure 8:
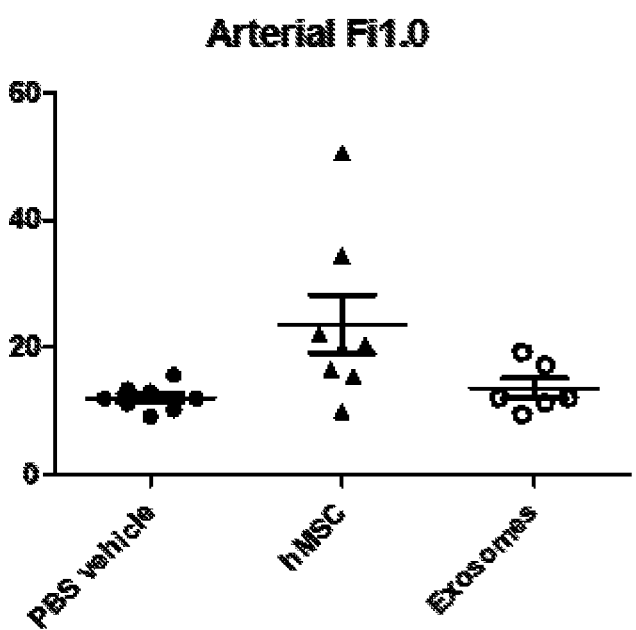
FIG. 8 shows arterial FI 1.0 in rats treated with PBS vehicle, human mesenchymal stem cells, or exosomes in a rat model of ARDS.

FIG. 8 shows arterial FI 1.0 in rats treated with PBS vehicle, human umbilical cord derived SDC2+ stromal cells, or exosomes in a rat model of ARDS. In this experiment, 300 g Sprague Dawley rats were given an intrapulmonary dose of E. coli to induce ARDS lung injury. One hour later, the rats were treated with a 90-100 µg dose of exosomes or 4 million human umbilical cord derived SDC2+ stromal cells. The extent of lung injury was then measured 24 hours later by measurement of arterial oxygen at FI 1.0. This experiment shows that rats treated with only 90-100 µg of exosomes had no decrease in lung function than those treated with PBS vehicle. This result indicates that exosome administration is not deleterious to animal lung recovery.

Figure 9:
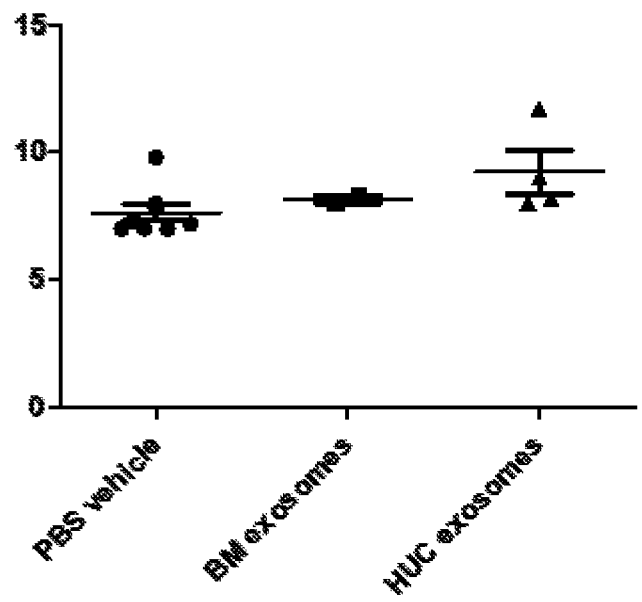
FIG. 9 shows arterial FI 0.3 in rats treated with PBS vehicle, bone marrow (BM) exosomes, or human umbilical cord (HUC) exosomes in a rat model of ARDS.

FIG. 9 shows arterial FI 0.3 in rats treated with PBS vehicle, bone marrow (BM) exosomes, or human umbilical cord (HUC) exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes purified from bone marrow mesenchymal stem cells or human umbilical cord mesenchymal stem cells. The extent of lung injury was then measured 24 hours later by measurement of arterial oxygen at FI 0.3. This experiment shows that rats treated with only 90-100 µg of exosomes had no decrease in lung function than those treated with PBS vehicle. It is expected that rats treated with a greater dose greater dose show increased improvement in lung function.

Figure 10:
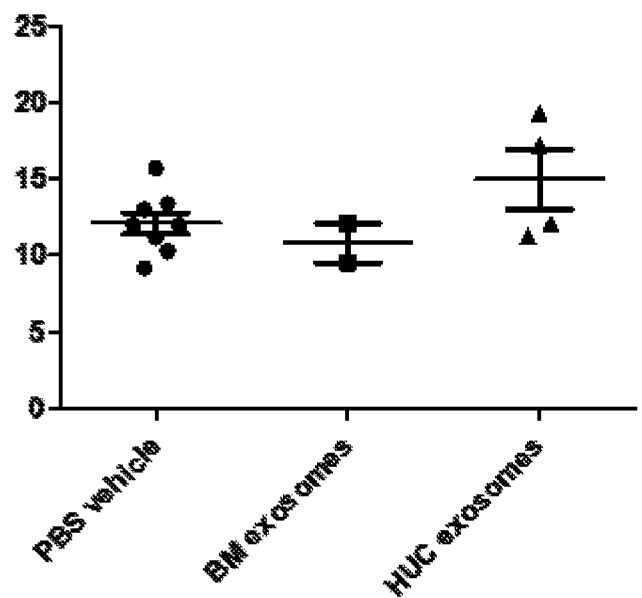
FIG. 10 shows arterial FI 1.0 in rats treated with PBS vehicle, bone marrow (BM) exosomes, or human umbilical cord (HUC) exosomes in a rat model of ARDS.

FIG. 10 shows arterial FI 1.0 in rats treated with PBS vehicle, bone marrow (BM) exosomes, or human umbilical cord (HUC) exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes purified from bone marrow mesenchymal stem cells or human umbilical cord mesenchymal stem cells. The extent of lung injury was then measured 24 hours later by measurement of arterial oxygen at FI 1.0. This experiment shows that rats treated with only 90-100 µg of exosomes had no decrease in lung function than those treated with PBS vehicle. It is expected that rats treated with a greater dose show increased improvement in lung function.

Figure 11:
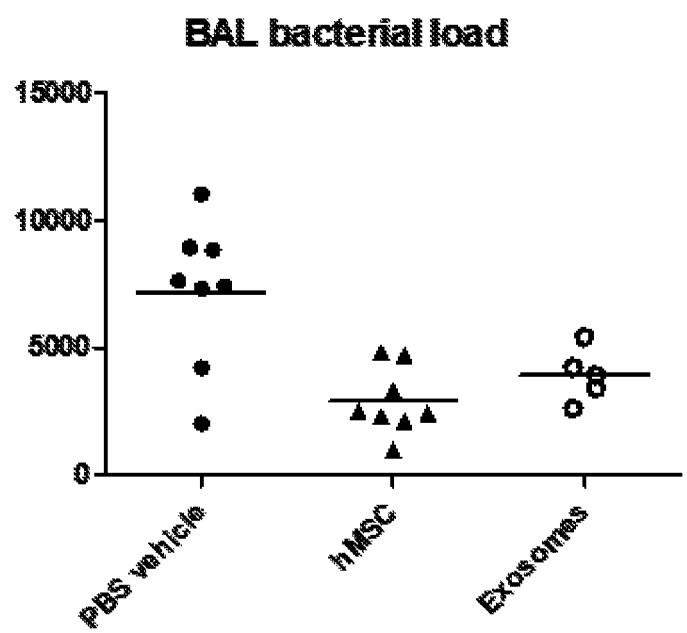
FIG. 11 shows bronchioaveolar lavage (BAL) bacterial load in rats treated with PBS vehicle, human mesenchymal stem cells, or exosomes in a rat model of ARDS.

FIG. 11 shows bronchioaveolar lavage (BAL) bacterial load in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of BAL bacterial load. This experiment shows that rats treated with only 90-100 µg of exosomes had reduced BAL bacterial load than those treated with PBS vehicle, demonstrating the efficacy of administering exosomes as a treatment. It is expected that rats treated with a greater dose show increased improvement in lung function.

Figure 12:
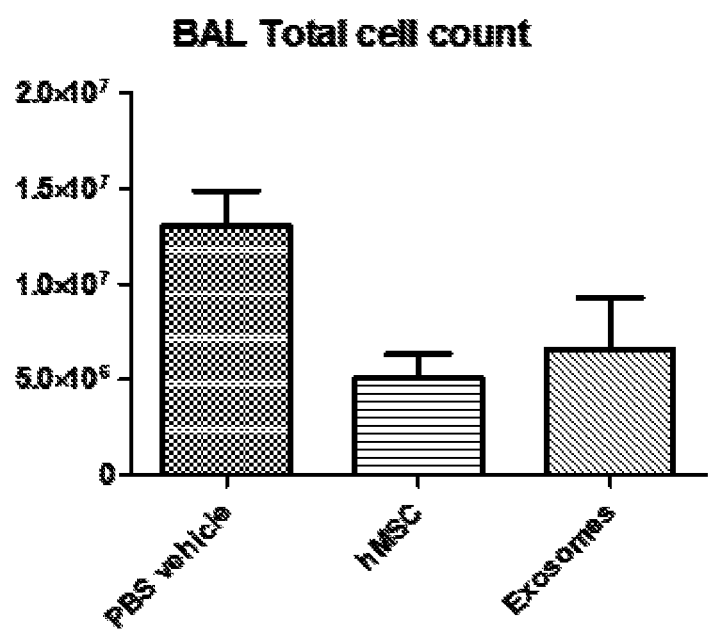
FIG. 12 shows bronchioaveolar lavage (BAL) total cell count in rats treated with PBS vehicle, human mesenchymal stem cells, or exosomes in a rat model of ARDS.

FIG. 12 shows bronchioaveolar lavage (BAL) total cell count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of BAL total cell count. This experiment shows that rats treated with only 90-100 µg of exosomes had reduced BAL total cell count compared to those treated with PBS vehicle, demonstrating the efficacy of administering exosomes as a treatment. It is expected that rats treated with a greater dose show even better improvement in lung function.

Figure 13:
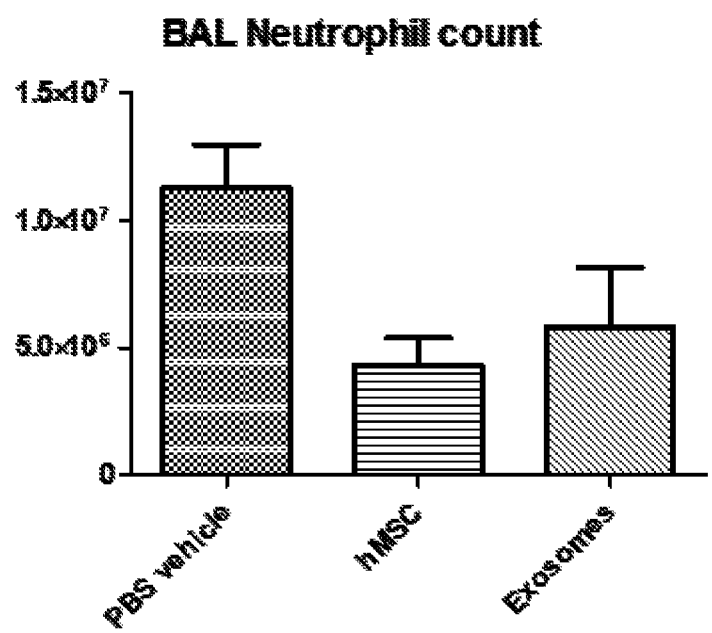
FIG. 13 shows bronchioaveolar lavage (BAL) neutrophil count in rats treated with PBS vehicle, human mesenchymal stem cells, or exosomes in a rat model of ARDS.

FIG. 13 shows bronchioaveolar lavage (BAL) neutrophil count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of BAL neutrophil count. This experiment shows that rats treated with only 90-100 µg of exosomes had fewer infiltrating neutrophils in the lung than those treated with PBS vehicle, demonstrating the efficacy of administering exosomes as a treatment. It is expected that rats treated with a greater dose show even better improvement in lung function.

Figure 14:
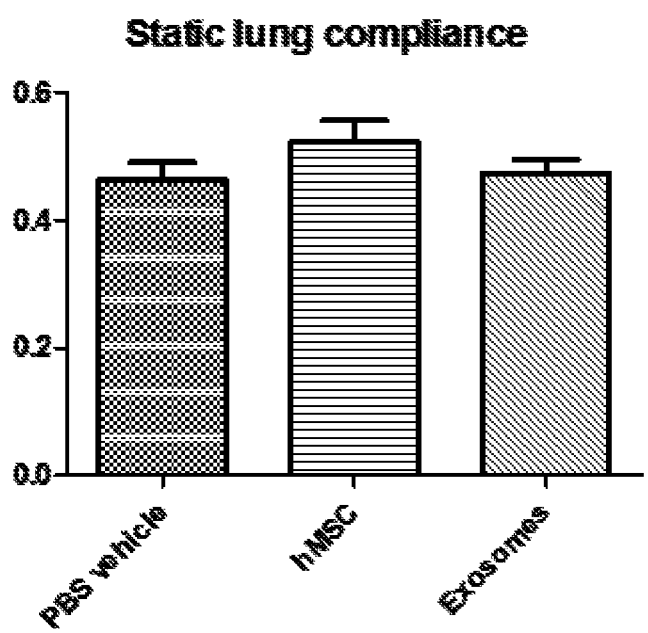
FIG. 14 shows static lung compliance in rats treated with PBS vehicle, human mesenchymal stem cells, or exosomes in a rat model of ARDS.

FIG. 14 shows static lung compliance in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of static lung compliance. This experiment shows that rats treated with only 90-100 µg of exosomes had no decrease in lung function than those treated with PBS vehicle. This result indicates that exosome administration is not deleterious to animal lung recovery.

Figure 15:
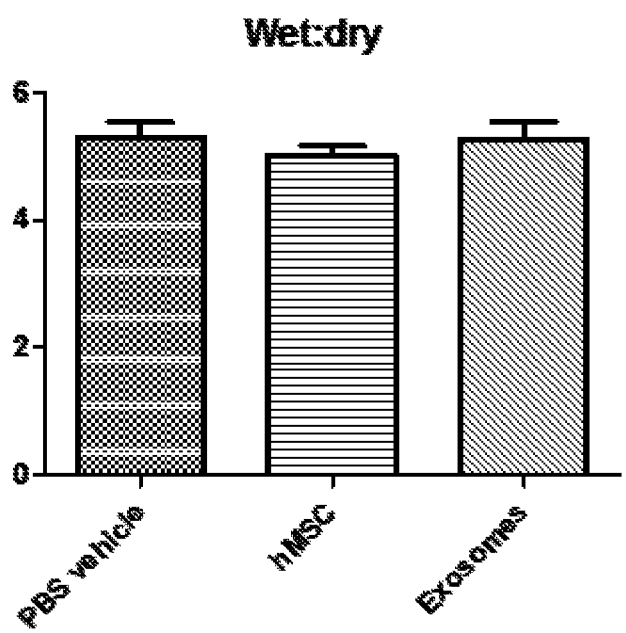
FIG. 15 shows lung wet dry ratio in rats treated with PBS vehicle, human mesenchymal stem cells, or exosomes in a rat model of ARDS.

FIG. 15 shows lung wet dry ratio in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of lung wet dry ratio. This experiment shows that rats treated with only 90-100 µg of exosomes had no decrease in lung function than those treated with PBS vehicle. This result indicates that exosome administration is not deleterious to animal lung recovery.

Figure 16:
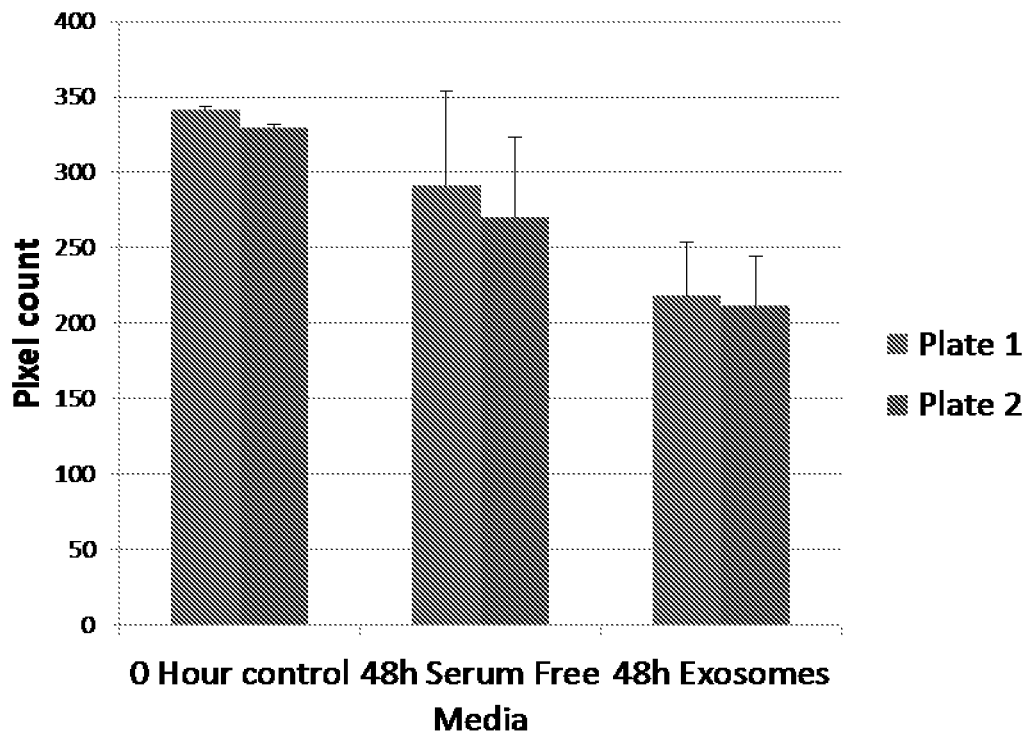
FIG. 16 shows results from a scratch assay with A549 cells treated with serum free media or exosomes for 48 hours.

FIG. 16 shows results from a scratch assay with A549 cells treated with serum free media or exosomes for 48 hours. The scratch assay measures cell migration into a scratch created in adherent cells growing in a culture dish. In this assay, 300,000 A549 cells were grown in a monolayer in a 24 well plate. The cells were scraped with a p200 pipet tip in a straight line to create a scratch. An image was taken at the time of scraping (0 h) and after a 48 hour incubation with serum free media or 2 µg exosomes in serum free media. Exosomes are shown there to reduce the size of the scratch, therefore increasing cell migration of A549 cells compared to the serum free media control. These results indicate that exosomes increase epithelial cell migration.

Figure 17:
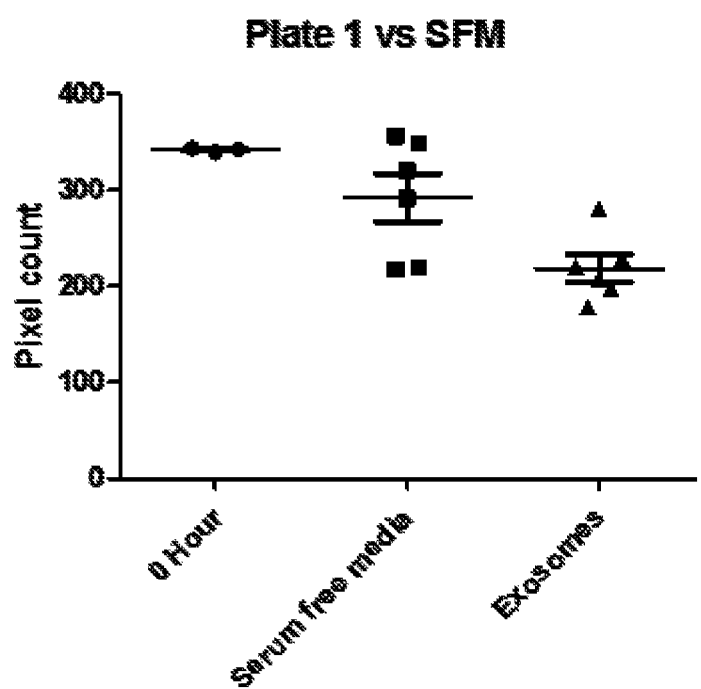
FIG. 17 shows results a scratch assay with A549 cells, plate 1.

FIG. 17 shows results a scratch assay with A549 cells, plate 1. An image was taken at the time of scraping (0 h) and after a 48 hour incubation with serum free media or 2 μg exosomes in serum free media. Exosomes are shown there to reduce the size of the scratch, therefore increasing cell migration of A549 cells compared to the serum free media control. These results indicate that exosomes increase epithelial cell migration.

Figure 18:
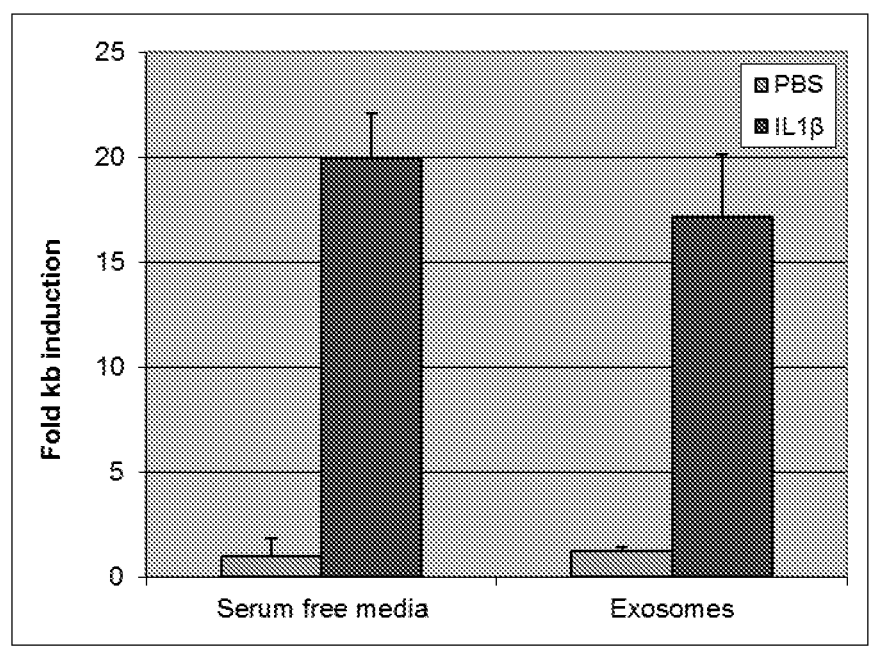
FIG. 18 shows a bar graph of NFκB reporter gene activation with IL1β stimulation in cells treated with serum free media or exosomes purified by ultrafiltration.

FIG. 18 shows a bar graph of NFκB reporter gene activation with IL1β stimulation in cells treated with serum free media or exosomes purified by ultrafiltration. In this assay, 30,000 A549 cells that were transfected with an NFκB-luciferase reporter gene were grown in a 96 well dish. The cells were treated with serum free media or 2 μg exosomes in serum free media for hours and then stimulated with human IL-1β for hours and luciferase activity was measured. A reduction was observed in luciferase activity in A549 cells treated with exosomes. Therefore, SDC2+ exosomes reduce NFκB activation.

Figure 19:
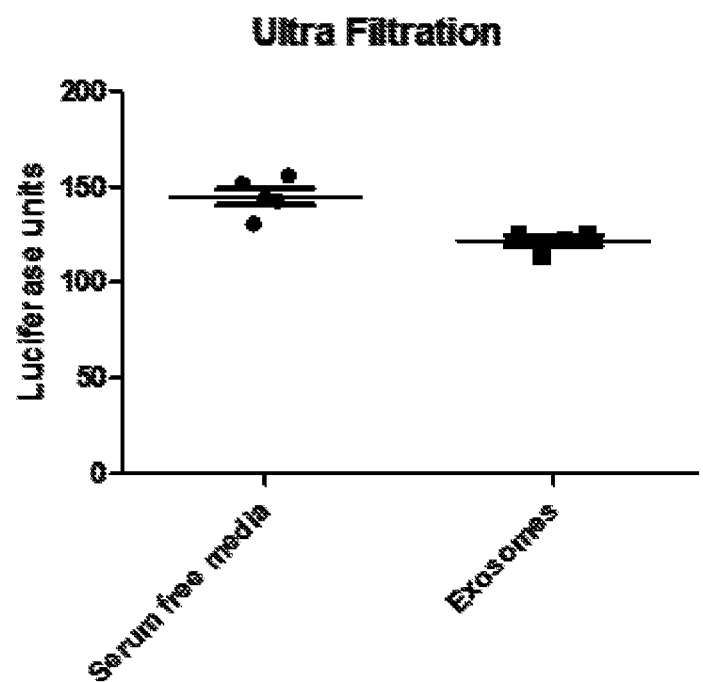
FIG. 19 shows a scatter graph of NFκB reporter gene activation with IL1β stimulation in cells treated with serum free media or exosomes purified by ultrafiltration.

FIG. 19 shows a scatter graph of NFκB reporter gene activation with IL1β stimulation in cells treated with serum free media or exosomes purified by ultrafiltration. In this assay, 30,000 A549 cells that were transfected with an NFκB-luciferase reporter gene were grown in a 96 well dish. The cells were treated with serum free media or 2 μg exosomes in serum free media and then stimulated with human IL-1β for hours and luciferase activity was measured. A reduction was observed in luciferase activity in A549 cells treated with exosomes. These results indicate that the exosome administration reduces NFκB activation.

Figure 20:
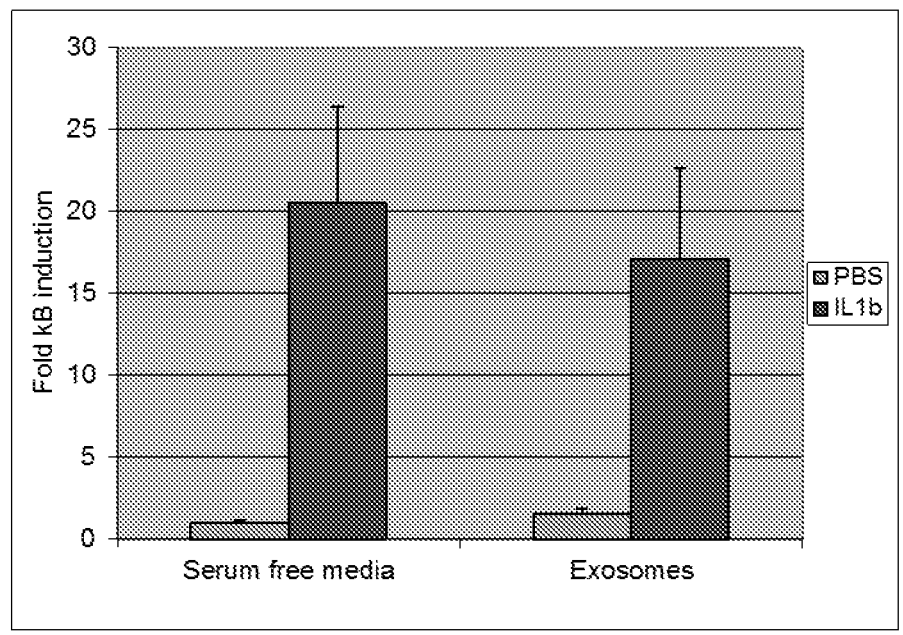
FIG. 20 shows a bar graph of NFκB reporter gene activation with IL1β stimulation in cells treated with serum free media or exosomes purified by ultracentrifugation.

FIG. 20 shows a bar graph of NFκB reporter gene activation with IL1β stimulation in cells treated with serum free media or exosomes purified by ultracentrifugation. In this assay, 30,000 A549 cells that were transfected with an NFκB-luciferase reporter gene were grown in a 96 well dish. The cells were treated with serum free media or 2 μg exosomes in serum free media for hours and then stimulated with human IL-1β for hours and luciferase activity was measured. A reduction was observed in luciferase activity in A549 cells treated with exosomes. Therefore, exosomes reduce NFκB activation.

Figure 21:
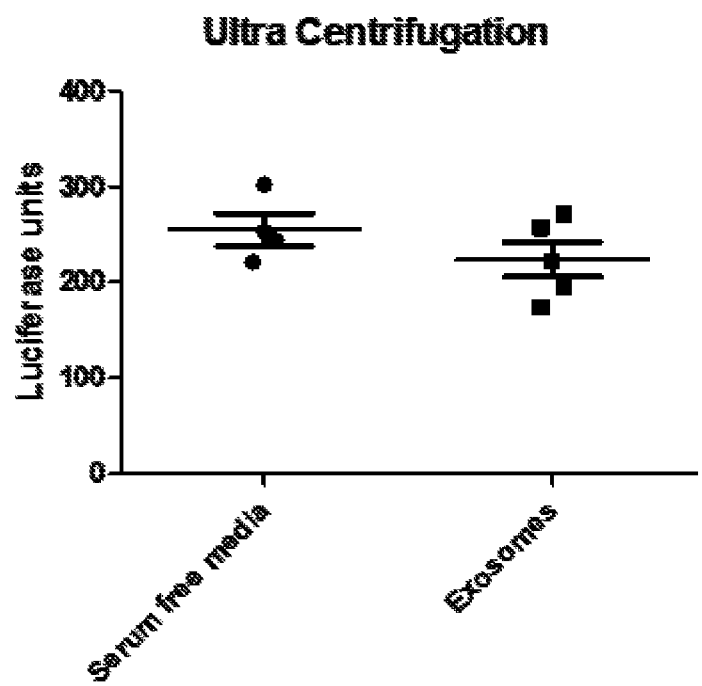
FIG. 21 shows a scatter graph of NFκB reporter gene activation with IL1β stimulation in cells treated with serum free media or exosomes purified by ultracentrifugation.

FIG. 21 shows a scatter graph of NFκB reporter gene activation with IL1β stimulation in cells treated with serum free media or exosomes purified by ultracentrifugation. In this assay, 30,000 A549 cells that were transfected with an NFκB-luciferase reporter gene were grown in a 96 well dish. The cells were treated with serum free media or 2 μg exosomes in serum free media for hours and then stimulated with human IL-1β for hours and luciferase activity was measured. A reduction was observed in luciferase activity in A549 cells treated with exosomes. These results indicate that the exosome administration reduces NFκB activation.

Figure 22:
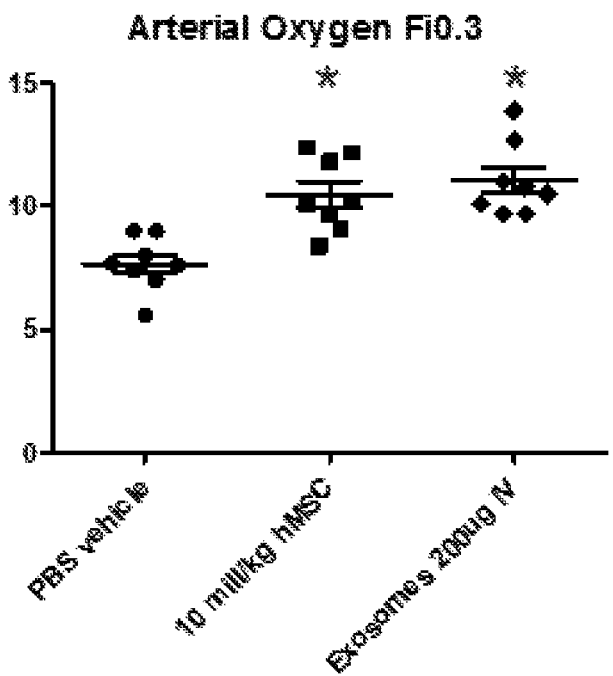
FIG. 22 shows arterial FI 0.3 in rats treated with PBS vehicle, human mesenchymal stem cells (10 mill/kg), or exosomes (200 μg, IV) in a rat model of ARDS.

FIG. 22 shows arterial FI 0.3 in rats treated with PBS vehicle, hMSC, or exosomes in a rat model of ARDS. In this experiment, 300 g Sprague Dawley rats were given an intrapulmonary dose of E. coli to induce ARDS lung injury, one hour later, the rats were treated with a 200 μg dose of exosomes or 10 million/kg human MSC by intravenous administration. The extent of lung injury was then measured 24 hours later by measurement of arterial oxygen at FI 0.3. This experiment shows that rats treated with 200 μg of exosomes or 10 million/kg human MSC had significantly improved lung function compared to those treated with PBS vehicle (one way anova p<0.0001). This result indicates that exosome administration is effective in treating animal lung injury and suggests that exosome treatment is comparable to hMSC treatment.

Figure 23:
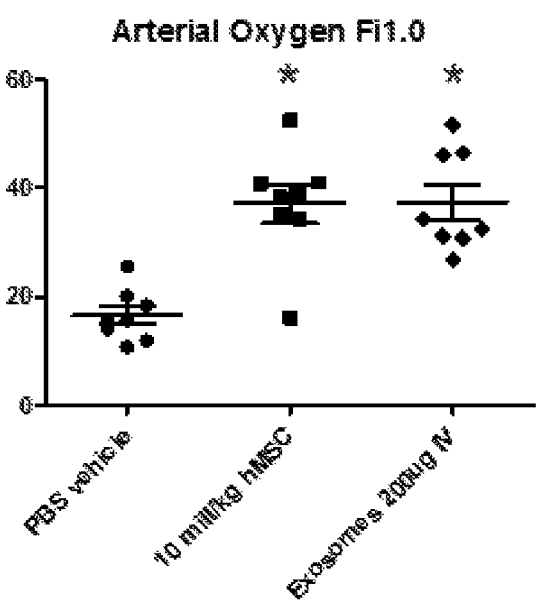
FIG. 23 shows arterial FI 1.0 in rats treated with PBS vehicle, human mesenchymal stem cells (10 mill/kg), or exosomes (200 μg, IV) in a rat model of ARDS.

FIG. 23 shows arterial FI 1.0 in rats treated with PBS vehicle, hMSC, or exosomes in a rat model of ARDS. In this experiment, 300 g Sprague Dawley rats were given an intrapulmonary dose of E. coli to induce ARDS lung injury, one hour later, the rats were treated with a 200 μg dose of exosomes or 10 million/kg human MSC by intravenous administration. The extent of lung injury was then measured 24 hours later by measurement of arterial oxygen at FI 0.3. This experiment shows that rats treated with 200 μg of exosomes or 10 million/kg human MSC had significantly improved lung function compared to those treated with PBS vehicle (one way anova p<0.0001). This result indicates that exosome administration is effective in treating animal lung injury and suggests that exosome treatment is comparable to hMSC treatment.

Figure 24:
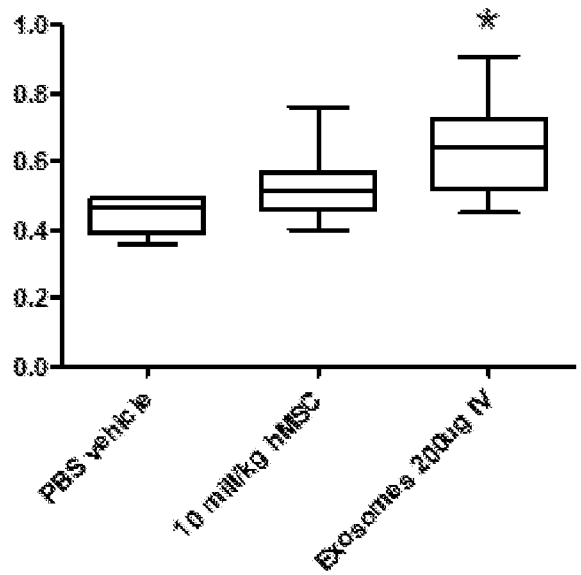
FIG. 24 shows static lung compliance in rats treated with PBS vehicle, human mesenchymal stem cells (10 mill/kg), or exosomes (200 μg, IV) in a rat model of ARDS.

FIG. 24 shows static lung compliance in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 200 μg intravenous dose of exosomes or 10 million/kg human mesenchymal stem cells (hMSC). The extent of lung injury was then measured 24 hours later by measurement of static lung compliance. This experiment shows that rats treated with 200 μg of exosomes or 10 million/kg human MSC had significantly improved lung function compared to those treated with PBS vehicle (one way anova p<0.01). This result indicates that exosome administration is effective in treating animal lung injury and suggests that exosome treatment is comparable to hMSC treatment.

Figure 25:
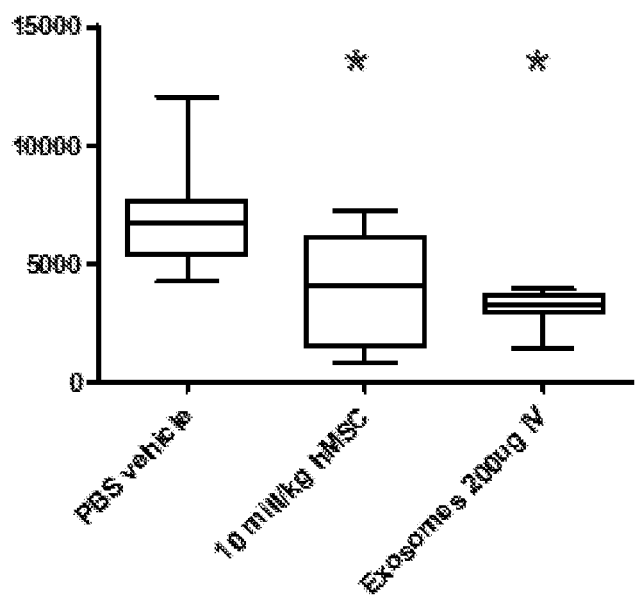
FIG. 25 shows bronchioaveolar lavage (BAL) bacterial load in rats treated with PBS vehicle, human mesenchymal stem cells (10 mill/kg), or exosomes (200 μg, IV) in a rat model of ARDS.

FIG. 25 shows bronchioaveolar lavage (BAL) bacterial load in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated intravenously with a 200 μg dose of exosomes or 10 million/kg human mesenchymal stem cells (hMSC). The extent of lung injury was then measured 24 hours later by measurement of BAL bacterial load. This experiment shows that rats treated with exosomes or hMSC had a significantly reduced BAL bacterial load than those treated with PBS vehicle (one way anova p<0.01), demonstrating the efficacy of administering exosomes as a treatment and suggests that exosome treatment is comparable to hMSC treatment.

Figure 26:
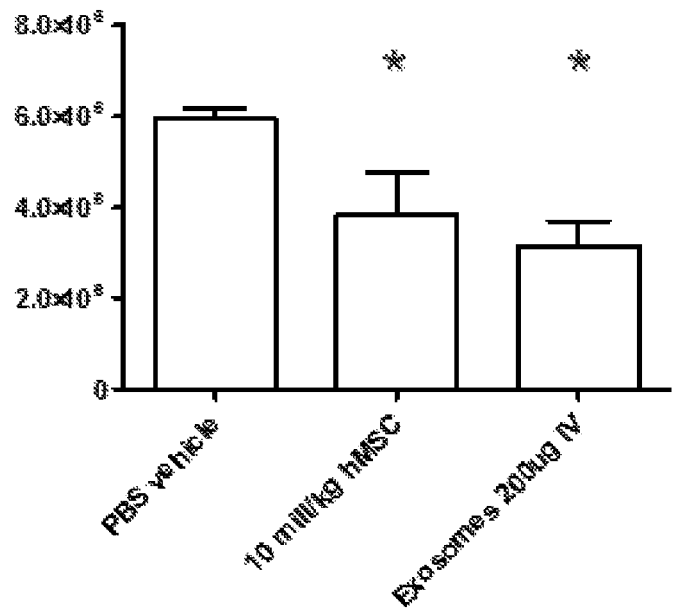
FIG. 26 shows bronchioaveolar lavage (BAL) total cell count in rats treated with PBS vehicle, human mesenchymal stem cells (10 mill/kg), or exosomes (200 μg, IV) in a rat model of ARDS.

FIG. 26 shows bronchioaveolar lavage (BAL) total cell count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated intravenously with a 200 μg dose of exosomes or 10 million/kg human mesenchymal stem cells (hMSC). The extent of lung injury was then measured 24 hours later by measurement of BAL total cell count. This experiment shows that rats treated with exosomes or hMSC had a significantly reduced BAL total cell count compared to those treated with PBS vehicle (one way anova p<0.01), demonstrating the efficacy of administering exosomes as a treatment and suggests that exosome treatment is comparable to hMSC treatment.

Figure 27:
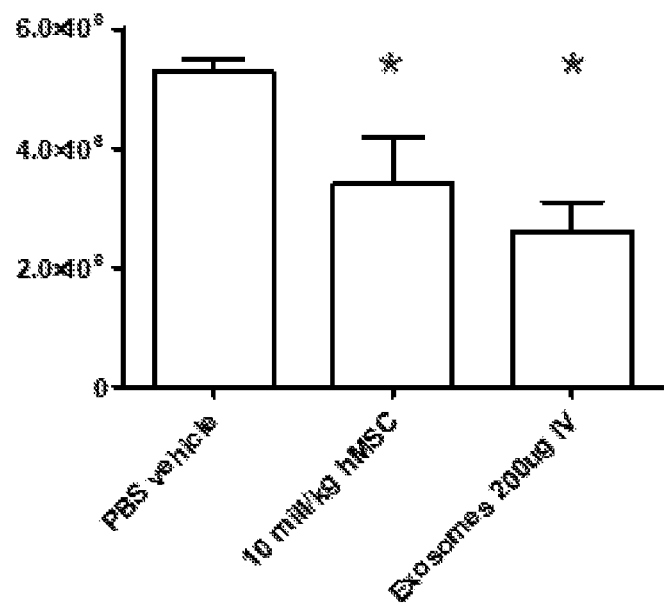
FIG. 27 shows bronchioaveolar lavage (BAL) neutrophil count in rats treated with PBS vehicle, human mesenchymal stem cells (10 mill/kg), or exosomes (200 μg, IV) in a rat model of ARDS.

FIG. 27 shows bronchioaveolar lavage (BAL) neutrophil count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated intravenously with a 200

µg dose of exosomes or 10 million/kg human mesenchymal stem cells (hMSC). The extent of lung injury was then measured 24 hours later by measurement of BAL neutrophil count. This experiment shows that rats treated with exosomes or hMSC had significantly reduced infiltrating neutrophils in the lung than those treated with PBS vehicle, demonstrating the efficacy of administering exosomes as a treatment and suggests that exosome treatment is comparable to hMSC treatment. Throughout the figures, a significant difference is indicated by an asterisk (*).

The disclosure herein is further clarified in reference to a partial list of numbered embodiments as follows. 1. A method of isolating a population of SDC2+ stromal stem cells from a mixed population of mammalian cells the method comprising: (a) contacting the mixed population of mammalian cells to a CD39 binding agent; (b) isolating cells bound to the CD39 binding agent; and (c) measuring SDC2+ cell abundance in the isolated cells, thereby isolating the population of SDC2+ stromal stem cells. 2. The method of embodiment 1, wherein the population of SDC2+ stromal stem cells comprise cells selected from a list consisting of human, mouse, rat, and equine cells. 3. The method of embodiment 1 or embodiment 2, wherein the mixed population of mammalian cells are obtained from a source selected from at least one of bone marrow, adipose tissue, skeletal muscle, endometrium, placenta, umbilical cord, Wharton's jelly, and cells derived from pluripotent cells. 4. The method of any one of embodiments 1 to 3, wherein the CD39 binding agent comprises an antibody. 5. The method of embodiment 4, wherein the antibody is raised to a CD39 antigen. 6. The method of embodiment 4, wherein the antibody comprises a variable domain that specifically binds to at least one mammalian CD39 protein. 7. The method of embodiment 4, wherein the antibody specifically binds to at least one of a human, a mouse, a rat, and equine CD39 protein. 8. The method of embodiment 4, wherein the antibody is conjugated to a fluorophore. 9. The method of embodiment 4, wherein the antibody is conjugated to a bead. 10. The method of any one of embodiments 1 to 9, wherein at least 20% of the population of SDC2+ stromal stem cells is SDC2+. 11. The method of any one of embodiments 1 to 10, wherein at least 40% of the population of SDC2+ stromal stem cells is SDC2+. 12. The method of any one of embodiments 1 to 11, wherein at least 70% of the population of SDC2+ stromal stem cells is SDC2+. 13. The method of any one of embodiments 1 to 12, wherein isolating the cells bound to the CD39 binding agent comprises fluorescence activated cell sorting. 14. The method of any one of embodiments 1 to 12, wherein isolating the cells bound to the CD39 binding agent comprises magnetic-activated cell sorting. 15. The method of any one of embodiments 1 to 14, comprising culturing the isolated cells. 16. The method of any one of embodiments 1 to 15, wherein at least 90% of the SDC2+ stromal stem cells are CD45−. 17. The method of any one of embodiments 1 to 16, wherein the cells bound to the CD39 binding agent further comprise CD25+ FoxP3+ regulatory T cells. 18. The method of any one of embodiments 1 to 17, comprising genetically modifying the cells to overexpress an apyrase. 19. The method of any one of embodiments 1 to 18, comprising genetically modifying the cells to overexpress a protein having a CD39 extracellular domain. 20. The method of any one of embodiments 1 to 19, comprising genetically modifying the cells to overexpress CD39. 21. The method of any one of embodiments 1 to 20, comprising genetically modifying the cells to overexpress CD39L3. 22. A method of preparing an immunomodulatory composition comprising a population of SDC2+ stromal stem cells, the method comprising (a) contacting a mixed population of mammalian cells to a CD39 binding agent; (b) isolating cells bound to the CD39 binding agent; and (c) measuring SDC2+ cell abundance in the isolated cells. 23. The method of embodiment 22, wherein the population of SDC2+ stromal stem cells is a population of human, a mouse, a rat, or an equine cells. 24. The method of embodiment 22 or embodiment 23, wherein the mixed population of mammalian cells are obtained from a source selected from at least one of bone marrow, adipose tissue, skeletal muscle, endometrium, placenta, umbilical cord, Wharton's jelly, and cells derived from pluripotent cells. 25. The method of any one of embodiments 22 to 24, wherein the CD39 binding agent comprises an antibody. 26. The method of embodiment 25, wherein the antibody is raised to a CD39 antigen. 27. The method of embodiment 25, wherein the antibody comprises a variable domain that specifically binds to at least one mammalian CD39 protein. 28. The method of embodiment 25, wherein the antibody specifically binds to at least one of a human, a mouse, a rat, and equine CD39 protein. 29. The method of embodiment 25, wherein the antibody is conjugated to a fluorophore. 30. The method of embodiment 25, wherein the antibody is conjugated to a bead. 31. The method of any one of embodiments 22 to 30, wherein at least 20% of the population of SDC2+ stromal stem cells is SDC2+. 32. The method of any one of embodiments 22 to 31, wherein at least 40% of the population of SDC2+ stromal stem cells is SDC2+. 33. The method of any one of embodiments 22 to 32, wherein at least 70% of the population of SDC2+ stromal stem cells is SDC2+. 34. The method of any one of embodiments 22 to 33, wherein isolating the cells bound to the CD39 binding agent comprises fluorescence activated cell sorting. 35. The method of any one of embodiments 22 to 33, wherein isolating the cells bound to the CD39 binding agent comprises magnetic-activated cell sorting. 36. The method of any one of embodiments 22 to 35, comprising culturing the cells isolated cells. 37. The method of any one of embodiments 22 to 36, wherein at least 90% of the SDC2+ stromal stem cells are CD45−. 38. The method of any one of embodiments 22 to 37, wherein the composition further comprises a buffer. 39. The method of any one of embodiments 22 to 38, wherein the composition further comprises an extracellular matrix. 40. The method of embodiment 39, wherein the extracellular matrix is comprises a collagen. 41. The method of embodiment 39, wherein the extracellular matrix is comprises a hyaluronic acid. 42. The method of any one of embodiments 22 to 41, wherein the composition further comprises a cryopreservant comprising DMSO. 43. The method of any one of embodiments 22 to 41, wherein the composition further comprises a cryopreservant comprising glycerol. 44. The method of any one of embodiments 22 to 43, wherein the population of SDC2+ stromal stem cells further comprises CD25+ FoxP3+ regulatory T cells. 45. The method of any one of embodiments 22 to 44, comprising genetically modifying the cells to overexpress an apyrase. 46. The method of any one of embodiments 22 to 45, comprising genetically modifying the cells to overexpress CD39. 47. The method of any one of embodiments 22 to 46, comprising genetically modifying the cells to overexpress CD39L3. 48. A method of isolating an immuno-modulatory composition comprising exosomes, the method comprising: (a) contacting a population of mammalian cells to a CD39 binding agent; (b) isolating the cells bound to the CD39 binding agent; and (c) recovering a supernatant comprising the exosomes from the isolated cells. 49. The method of embodiment 48, comprising obtaining an exosome fraction from the supernatant. 50. The method of embodiment 49, wherein obtaining an exosome fraction comprises centrifuging the supernatant. 51. The method of embodiment 50, wherein the centrifugation comprises centrifuging the cells at about 100,000 g. 52. The method of embodiment 50 or embodiment 51, wherein the centrifugation comprises centrifuging the cells for at least one hour. 53. The method of any one of embodiments 50 to 52, wherein the centrifugation comprises ultrafiltration. 54. The method of any one of embodiments 50 to 53, wherein the centrifugation comprises size-exclusion liquid chromatography. 55. The method of any one of embodiments 49 to 54, wherein obtaining an exosome fraction comprises ultrafiltration. 56. The method of any one of embodiments 49 to 55, wherein obtaining an exosome fraction comprises size-exclusion liquid chromatography. 57. The method of any one of embodiments 49 to 56, wherein obtaining an exosome fraction comprises contacting the supernatant to an antibody. 58. The method of embodiment 57, wherein the antibody is selected from at least one of an anti-CD39 antibody and an anti-SDC2 antibody. 59. The method of any one of embodiments 48 to 58, wherein the exosomes are paracrine signaling exosomes. 60. The method of any one of embodiments 48 to 59, wherein the isolated cells are SDC2+. 61. The method of any one of embodiments 48 to 60, wherein the isolated cells comprise mesenchymal stem cells. 62. The method of any one of embodiments 48 to 61, wherein at least 90% of the isolated cells are CD45−. 63. The method of any one of embodiments 48 to 62, wherein the method comprises storing the exosome fraction at room temperature. 64. The method of any one of embodiments 48 to 63, wherein the method comprises storing the exosome fraction without cryogenic preservation. 65. The method of any one of embodiments 48 to 64, wherein the method comprises adding an immunosuppressive drug to the immuno-modulatory composition. 66. The method of any one of embodiments 48 to 65, wherein the isolated cells are perturbed to elicit exosome production. 67. The method of any one of embodiments 48 to 66, wherein the isolated cells are cultured in a hollow-fiber bioreactor. 68. The method of any one of embodiments 48 to 67, wherein the isolated cells further comprise CD25+ FoxP3+ regulatory T cells. 69. The method of any one of embodiments 48 to 68, comprising genetically modifying the isolated cells to overexpress an apyrase. 70. The method of any one of embodiments 48 to 69, comprising genetically modifying the isolated cells to overexpress CD39. 71. The method of any one of embodiments 48 to 70, comprising genetically modifying the isolated cells to overexpress CD39L3. 72. A method of modulating an inflammation response in a mammal comprising delivering a composition comprising SDC2+ cells to a site of the inflammation response, wherein the SDC2+ cells are isolated from a mixed population of cells by isolating cells based upon CD39 expression. 73. The method of embodiment 72, wherein isolating cells comprises collecting cells bound to a CD39 binding agent. 74. The method of embodiment 73, wherein isolating the cells comprises culturing the cells bound to the CD39 binding agent. 75. The method of any one of embodiments 72 to 74, wherein delivering comprises injecting the composition comprising SDC2+ cells. 76. The method of any one of embodiments 72 to 74, wherein delivering comprises topically applying the composition comprising SDC2+ cells. 77. The method of embodiment 76, wherein the composition comprises a hydrogel. 78. The method of embodiment 76, wherein the composition comprises a collagen gel. 79. The method of any one of embodiments 72 to 74, wherein delivering comprises intraocularly administering the composition comprising SDC2+ cells. 80. The method of any one of embodiments 72 to 74, wherein delivering comprises ophthalmic application of the composition comprising SDC2+ cells. 81. The method of any one of embodiments 72 to 74, wherein delivering comprises intravenous delivery the composition comprising SDC2+ cells. 82. The method of any one of embodiments 72 to 74, wherein delivering comprises intra-lymph node injection of the composition comprising SDC2+ cells. 83. The method of any one of embodiments 72 to 74, wherein delivering comprises subcutaneous delivery of the composition comprising SDC2+ cells. 84. The method of any one of embodiments 72 to 74, wherein delivering comprises intraperitoneal delivery of the composition comprising SDC2+ cells. 85. The method of any one of embodiments 72 to 74, wherein delivering comprises intrathecal delivery of the composition comprising SDC2+ cells. 86. The method of any one of embodiments 72 to 85, wherein the SDC2+ cells wherein the SDC2+ cells are selected from at least one of human, mouse, rat, and equine cells. 87. The method of any one of embodiments 72 to 86, wherein the mixed population of mammalian cells are obtained from a source selected from bone marrow, adipose tissue, skeletal muscle, endometrium, placenta, umbilical cord, Wharton's jelly, and cells derived from pluripotent cells. 88. The method of any one of embodiments 72 to 87, wherein the CD39 binding agent comprises an antibody. 89. The method of embodiment 88, wherein the antibody is raised to a CD39 antigen. 90. The method of embodiment 88, wherein the antibody comprises a variable domain that specifically binds to at least one mammalian CD39 protein. 91. The method of embodiment 88, wherein the antibody specifically binds to at least one of a human, a mouse, a rat, or equine CD39 protein. 92. The method of embodiment 88, wherein the antibody is conjugated to a fluorophore. 93. The method of embodiment 88, wherein the antibody is conjugated to a bead. 94. The method of any one of embodiments 72 to 93, wherein at least 20% of the SDC2+ cells are SDC2+. 95. The method of any one of embodiments 72 to 94, wherein at least 40% of the SDC2+ cells are SDC2+. 96. The method of any one of embodiments 72 to 95, wherein at least 70% of the SDC2+ cells are SDC2+. 97. The method of any one of embodiments 72 to 96, wherein isolating the cells comprises fluorescence activated cell sorting. 98. The method of any one of embodiments 72 to 96, wherein isolating the cells comprises magnetic-activated cell sorting. 99. The method of any one of embodiments 72 to 98, wherein at least 90% of the SDC2+ cells are CD45−. 100. The method of any one of embodiments 72 to 99, wherein the method comprises delivering at least $10^3$ SDC2+ cells. 101. The method of any one of embodiments 72 to 100, wherein the method comprises delivering at least $10^4$ SDC2+ cells. 102. The method of any one of embodiments 72 to 101, wherein the method comprises delivering at least $10^5$ SDC2+ cells. 103. The method of any one of embodiments 72 to 102, wherein the method comprises delivering at least $10^6$ SDC2+ cells. 104. The method of any one of embodiments 72 to 103, wherein the isolated cells comprise CD25+ FoxP3+ regulatory T cells. 105. The method of any one of embodiments 72 to 104, comprising genetically modifying the isolated cells to overexpress an apyrase. 106. The method of any one of embodiments 72 to 105, comprising genetically modifying the isolated cells to overexpress CD39. 107. The method of any one of embodiments 72 to 106, comprising genetically modifying the isolated cells to overexpress CD39L3. 108. The method of any one of embodiments 72 to 107, wherein the inflammation response comprises at least one of type 1 diabetes, type 2 diabetes, sepsis, Crohn's disease, inflammatory bowel syndrome, rheumatoid arthritis, graft versus host disease, multiple sclerosis, ALS, a dermal wound, a bone fracture, a concussion wound, a burn, atherosclerosis, nephropathy, cardiomyopathy, neuropathy, a kidney disorder, kidney failure, a diabetic ulcer, a leg ulcer, ARDS, sepsis, inflammatory liver disease, myocarditis, postmyocardial infarction syndrome, postpericardiotomy syndrome, subacute bacterial endocarditis, anti-glomulerular basement membrane nephritis, interstitial cystitis, lupus nephritis, autoimmune hepatitis, primary biliary cirrhosis, primary sclerosing cholangitis, antisynthetase syndrome, asthma, chronic obstructive pulmonary disease, cystic fibrosis, atelectasis, bronchitis, emphysema, pneumonia, pulmonary edema, Alopecia Areata, autoimmune Angioedema, autoimmune progesterone dermatitis, autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, autoimmune polyendocrine syndrome, autoimmune polyendocrine syndrome type 2, autoimmune polyendocrine syndrome type 3, autoimmune pancreatitis, autoimmune thyroiditis, Ord's thyroiditis, Graves' disease, Reproductive Organ disorder, autoimmune oophoritis, Endometriosis, autoimmune orchitis, Sjogren's syndrome, autoimmune enteropathy, Celiac disease, Microscopic colitis, Ulcerative colitis, Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, Undifferentiated connective tissue disease, cachexia, sarcophenia, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff's encephalitis, Chronic inflammatory demyelinating polyneuropathy, Guillain-Barré syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with Streptococcus, Progressive inflammatory neuropathy, Restless leg syndrome, Stiff person syndrome, Sydenham chorea, amyotrophic lateral sclerosis, Parkinson's disease, Alzheimer's disease, Transverse myelitis, autoimmune retinopathy, autoimmune uveitis, Cogan syndrome, Graves ophthalpathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, autoimmune inner ear disease, Meniere's disease, Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, and Vasculitis. 109. A method of modulating an inflammation response in a mammal comprising delivering a composition comprising exosomes to a site of the inflammation response, wherein the exosomes are SDC2+ and the exosomes are from SDC2+ cells isolated from a mixed population of mammalian cells based upon CD39 expression. 110. The method of embodiment 109, wherein isolating cells comprises collecting cells bound to a CD39 binding agent. 111. The method of embodiment 109 or embodiment 110, wherein isolating the cells comprises culturing the cells bound to the CD39 binding agent. 112. The method of any one of embodiments 109 to 111, wherein delivering comprises injecting the composition comprising exosomes. 113. The method of any one of embodiments 109 to 111, wherein delivering comprises topically applying the composition comprising exosomes. 114. The method of embodiment 113, wherein the composition comprises a hydrogel. 115. The method of embodiment 113, wherein the composition comprises a collagen gel. 116. The method of any one of embodiments 109 to 111, wherein delivering comprises intraocularly administering the composition comprising exosomes. 117. The method of any one of embodiments 109 to 111, wherein delivering comprises ophthalmic application of the composition comprising exosomes. 118. The method of any one of embodiments 109 to 111, wherein delivering comprises intravenous delivery the composition comprising exosomes. 119. The method of any one of embodiments 109 to 111, wherein delivering comprises intra-lymph node injection of the composition comprising exosomes. 120. The method of any one of embodiments 109 to 111, wherein delivering comprises subcutaneous delivery of the composition comprising exosomes. 121. The method of any one of embodiments 109 to 111, wherein delivering comprises intraperitoneal delivery of the composition comprising exosomes. 122. The method of any one of embodiments 109 to 111, wherein delivering comprises intrathecal delivery of the composition comprising exosomes. 123. The method of any one of embodiments 109 to 122, wherein the exosomes are isolated from SDC2+ cells that are at least one of human, mouse, rat, and equine cells. 124. The method of any one of embodiments 109 to 123, wherein the mixed population of mammalian cells are obtained from a source selected from bone marrow, adipose tissue, skeletal muscle, endometrium, placenta, umbilical cord, Wharton's jelly, and cells derived from pluripotent cells. 125. The method of any one of embodiments 109 to 124, wherein the CD39 binding agent comprises an antibody. 126. The method of embodiment 125, wherein the antibody is raised to a CD39 antigen. 127. The method of embodiment 125, wherein the antibody comprises a variable domain that specifically binds to at least one mammalian CD39 protein. 128. The method of embodiment 125, wherein the antibody specifically binds to at least one of a human, a mouse, a rat, or equine CD39 protein. 129. The method of embodiment 125, wherein the antibody is conjugated to a fluorophore. 130. The method of embodiment 125, wherein the antibody is conjugated to a bead. 131. The method of any one of embodiments 109 to 130, wherein at least 20% of the exosomes are SDC2+. 132. The method of any one of embodiments 109 to 131, wherein at least 40% of the exosomes are SDC2+. 133. The method of any one of embodiments 109 to 132, wherein at least 70% of the exosomes are SDC2+. 134. The method of any one of embodiments 109 to 133, wherein isolating the cells comprises fluorescence activated cell sorting. 135. The method of any one of embodiments 109 to 133, wherein isolating the cells comprises magnetic-activated cell sorting. 136. The method of any one of embodiments 109 to 135, wherein the method further comprises culturing the cells bound to the CD39 binding agent. 137. The method of any one of embodiments 109 to 136, wherein the cells are CD45−. 138. The method of any one of embodiments 109 to 137, wherein the method comprises delivering at least $10^6$ exosomes. 139. The method of any one of embodiments 109 to 138, wherein the method comprises delivering at least $10^7$ exosomes. 140. The method of any one of embodiments 109 to 139, wherein the method comprises delivering at least $10^8$ exosomes. 141. The method of any one of embodiments 109 to 140, wherein the method comprises delivering at least $10^9$ exosomes. 142. The method of any one of embodiments 109 to 141, wherein the isolated cells comprise CD25+ FoxP3+ regulatory T cells. 143. The method of any one of embodiments 109 to 142, comprising genetically modifying the isolated cells to overexpress an apyrase. 144. The method of any one of embodiments 109 to 143, comprising genetically modifying the isolated cells to overexpress CD39. 145. The method of any one of embodiments 109 to 144, comprising genetically modifying the isolated cells to overexpress CD39L3. 146. The method of any one of embodiments 109 to 145, wherein the inflammation response comprises at least one of type 1 diabetes, type 2 diabetes, sepsis, Crohn's disease, inflammatory bowel syndrome, rheumatoid arthritis, graft versus host disease, multiple sclerosis, ALS, a dermal wound, a bone fracture, a concussion wound, a burn, atherosclerosis, nephropathy, cardiomyopathy, neuropathy, a kidney disorder, kidney failure, a diabetic ulcer, a leg ulcer, ARDS, sepsis, inflammatory liver disease, myocarditis, postmyocardial infarction syndrome, postpericardiotomy syndrome, subacute bacterial endocarditis, anti-glomulerular basement membrane nephritis, interstitial cystitis, lupus nephritis, autoimmune hepatitis, primary biliary cirrhosis, primary sclerosing cholangitis, antisynthetase syndrome, asthma, chronic obstructive pulmonary disease, cystic fibrosis, atelectasis, bronchitis, emphysema, pneumonia, pulmonary edema, Alopecia Areata, autoimmune Angioedema, autoimmune progesterone dermatitis, autoimmune urticaria, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, autoimmune polyendocrine syndrome, autoimmune polyendocrine syndrome type 2, autoimmune polyendocrine syndrome type 3, autoimmune pancreatitis, autoimmune thyroiditis, Ord's thyroiditis, Graves' disease, Reproductive Organ disorder, autoimmune oophoritis, Endometriosis, autoimmune orchitis, Sjogren's syndrome, autoimmune enteropathy, Celiac disease, Microscopic colitis, Ulcerative colitis, Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, Undifferentiated connective tissue disease, cachexia, sarcophenia, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff's encephalitis, Chronic inflammatory demyelinating polyneuropathy, Guillain-Barré syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with Streptococcus, Progressive inflammatory neuropathy, Restless leg syndrome, Stiff person syndrome, Sydenham chorea, amyotrophic lateral sclerosis, Parkinson's disease, Alzheimer's disease, Transverse myelitis, autoimmune retinopathy, autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, autoimmune inner ear disease, Meniere's disease, Anti-neutrophil cytoplasmic antibody-associated vasculitis, Behçet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, Polyarteritis nodosa, Polymyalgia rheumatica, Urticarial vasculitis, and Vasculitis. 147. A composition comprising a population of cells that is at least 20% SDC2+, wherein the population of cells is bound to a CD39 binding agent. 148. The composition of embodiment 147, wherein the population of cells is at least 30% SDC2+. 149. The composition of embodiment 147 or embodiment 148, wherein the population of cells is at least 40% SDC2+. 150. The composition of any one of embodiments 147 to 149, wherein the population of cells is at least 50% SDC2+. 151. The composition of any one of embodiments 147 to 150, wherein the population of cells is at least 60% SDC2+. 152. The composition of any one of embodiments 147 to 151, wherein the population of cells is at least 70% SDC2+. 153. The composition of any one of embodiments 147 to 152, wherein the population of cells is at least 80% SDC2+. 154. The composition of any one of embodiments 147 to 153, wherein the population of cells is at least 90% SDC2+. 155. The composition of any one of embodiments 147 to 154, wherein the population of cells is at least 95% SDC2+. 156. The composition of any one of embodiments 147 to 155, wherein the population of cells is at least 99% SDC2+. 157. The composition of any one of embodiments 147 to 156, wherein the population of cells is at least 20% CD39+. 158. The composition of any one of embodiments 147 to 157, wherein the population of cells is at least 30% CD39+. 159. The composition of any one of embodiments 147 to 158, wherein the population of cells is at least 40% CD39+. 160. The composition of any one of embodiments 147 to 159, wherein the population of cells is at least 50% CD39+. 161. The composition of any one of embodiments 147 to 160, wherein the population of cells is at least 60% CD39+. 162. The composition of any one of embodiments 147 to 161, wherein the population of cells is at least 70% CD39+. 163. The composition of any one of embodiments 147 to 162, wherein the population of cells is at least 80% CD39+. 164. The composition of any one of embodiments 147 to 163, wherein the population of cells is at least 90% CD39+. 165. The composition of any one of embodiments 147 to 164, wherein the population of cells is at least 95% CD39+. 166. The composition of any one of embodiments 147 to 165, wherein the population of cells is at least 99% CD39+. 167. The composition of any one of embodiments 147 to 166, wherein at least 90% of the population of cells is CD45−. 168. The composition of any one of embodiments 147 to 167, further comprising at least $10^6$ exosomes isolated from a population of cells bound to a CD39 binding agent. 169. The composition of any one of embodiments 147 to 168, further comprising at least $10^7$ exosomes isolated from a population of cells bound to a CD39 binding agent. 170. The composition of any one of embodiments 147 to 169, further comprising at least $10^8$ exosomes isolated from a population of cells bound to a CD39 binding agent. 171. The composition of any one of embodiments 147 to 170, further comprising at least 1 μg of exosomes isolated from a population of cells bound to a CD39 binding agent. 172. The composition of any one of embodiments 147 to 171, further comprising at least 10 μg of exosomes isolated from a population of cells bound to a CD39 binding agent. 173. The composition of any one of embodiments 147 to 172, further comprising at least 20 μg of exosomes isolated from a population of cells bound to a CD39 binding agent. 174. The composition of any one of embodiments 147 to 173, further comprising at least 50 μg of exosomes isolated from a population of cells bound to a CD39 binding agent. 175. The composition of any one of embodiments 147 to 174, further comprising at least 100 μg of exosomes isolated from a population of cells bound to a CD39 binding agent. 176. The composition of any one of embodiments 147 to 175, further comprising at least 150 μg of exosomes isolated from a population of cells bound to a CD39 binding agent. 177. The composition of any one of embodiments 147 to 176, further comprising at least 200 μg of exosomes isolated from a population of cells bound to a CD39 binding agent. 178. The composition of any one of embodiments 147 to 177, further comprising at least 250 μg of exosomes isolated from a population of cells bound to a CD39 binding agent. 179. The composition of any one of embodiments 147 to 178, further comprising at least 500 μg of exosomes isolated from a population of cells bound to a CD39 binding agent. 180. The composition of any one of embodiments 147 to 179, further comprising at least 750 μg of exosomes isolated from a population of cells bound to a CD39 binding agent. 181. The composition of any one of embodiments 147 to 180, further comprising at least 1000 μg of exosomes isolated from a population of cells bound to a CD39 binding agent. 182. The composition of any one of embodiments 147 to 181, further comprising a buffer. 183. The composition of any one of embodiments 147 to 182, further comprising a cyropreservant comprising DMSO. 184. The composition of any one of embodiments 147 to 182, further comprising a cyropreservant comprising glycerol. 185. The composition of any one of embodiments 147 to 184, comprising at least $10^3$ cells. 186. The composition of any one of embodiments 147 to 185, comprising at least $10^4$ cells. 187. The composition of any one of embodiments 147 to 186, comprising at least $10^5$ cells. 188. The composition of any one of embodiments 147 to 187, comprising at least $10^6$ cells. 189. The composition of any one of embodiments 147 to 188, comprising at least $10^7$ cells. 190. The composition of any one of embodiments 147 to 189, wherein the population of cells comprises CD25+ FoxP3+ regulatory T cells. 191. The composition of any one of embodiments 147 to 190, wherein the population of cells is genetically modified to overexpress an apyrase. 192. The composition of any one of embodiments 147 to 191, wherein the population of cells is genetically modified to overexpress CD39. 193. The composition of any one of embodiments 147 to 192, wherein the population of cells is genetically modified to overexpress CD39L3. 194. A composition comprising exosomes, wherein the exosomes are at least 20% SDC2+ and wherein the exosomes are bound to a CD39 binding agent. 195. The composition of embodiment 194, wherein the exosomes are at least 30% SDC2+. 196. The composition of embodiment 194 or embodiment 195, wherein the exosomes are at least 40% SDC2+. 197. The composition of any one of embodiments 194 to 196, wherein the exosomes are at least 50% SDC2+. 198. The composition of any one of embodiments 194 to 197, wherein the exosomes are at least 60% SDC2+. 199. The composition of any one of embodiments 194 to 198, wherein the exosomes are at least 70% SDC2+. 200. The composition of any one of embodiments 194 to 199, wherein the exosomes are at least 80% SDC2+. 201. The composition of any one of embodiments 194 to 200, wherein the exosomes are at least 90% SDC2+. 202. The composition of any one of embodiments 194 to 201, wherein the exosomes are at least 95% SDC2+. 203. The composition of any one of embodiments 194 to 202, wherein the exosomes are at least 99% SDC2+. 204. The composition of any one of embodiments 194 to 203, wherein the exosomes are at least 20% CD39+. 205. The composition of any one of embodiments 194 to 204, wherein the exosomes are at least 30% CD39+. 206. The composition of any one of embodiments 194 to 205, wherein the exosomes are at least 40% CD39+. 207. The composition of any one of embodiments 194 to 206, wherein the exosomes are at least 50% CD39+. 208. The composition of any one of embodiments 194 to 207, wherein the exosomes are at least 60% CD39+. 209. The composition of any one of embodiments 194 to 208, wherein the exosomes are at least 70% CD39+. 210. The composition of any one of embodiments 194 to 209, wherein the exosomes are at least 80% CD39+. 211. The composition of any one of embodiments 194 to 210, wherein the exosomes are at least 90% CD39+. 212. The composition of any one of embodiments 194 to 211, wherein the exosomes are at least 95% CD39+. 213. The composition of any one of embodiments 194 to 212, wherein the exosomes are at least 99% CD39+. 214. The composition of any one of embodiments 194 to 213, wherein the population is CD45−. 215. The composition of any one of embodiments 194 to 214, comprising at least $10^6$ exosomes. 216. The composition of any one of embodiments 194 to 215, comprising at least $10^7$ exosomes. 217. The composition of any one of embodiments 194 to 216, comprising at least $10^8$ exosomes. 218. The composition of any one of embodiments 194 to 217, comprising at least 1 μg of exosomes. 219. The composition of any one of embodiments 194 to 218, comprising at least 10 μg of exosomes. 220. The composition of any one of embodiments 194 to 219, comprising at least 20 μg of exosomes. 221. The composition of any one of embodiments 194 to 220, comprising at least 50 μg of exosomes. 222. The composition of any one of embodiments 194 to 221, comprising at least 100 μg of exosomes. 223. The composition of any one of embodiments 194 to 222, comprising at least 150 μg of exosomes. 224. The composition of any one of embodiments 194 to 223, comprising at least 200 μg of exosomes. 225. The composition of any one of embodiments 194 to 224, comprising at least 250 µg of exosomes. 226. The composition of any one of embodiments 194 to 225, comprising at least 500 µg of exosomes. 227. The composition of any one of embodiments 194 to 226, comprising at least 750 µg of exosomes. 228. The composition of any one of embodiments 194 to 227, comprising at least 1000 µg of exosomes. 229. The composition of any one of embodiments 194 to 228, comprising a buffer.

Definitions

In some cases "exosomes" or "microvesicles" used interchangeably herein include cell-derived vesicles, which are released into the extracellular environment by a cell, for example a cultured cell or a cultured stromal cell.

"SDC2," also known as syndecan-2, CD362, S2, or fibroglycan, refers generally herein to the SDC2 polypeptide specified by the sequence listing, or the polypeptide encoded by the SDC2 locus. Syndecan-2, or 'the SDC2 protein' or simply SDC2, is a transmembrane type I heparin sulfate proteoglycan. Additional synonyms for syndecan-2, aside from 'the SDC2 protein' or SDC2, include HSPG, CD362, HSPG1, and SYND2. Generally, as used herein SDC2 refers to the protein or a recognizable fragment thereof unless otherwise indicated, for example by reciting 'the SDC2 gene,' 'the SDC2 transcript,' 'an SDC2 antibody.' Additionally, SDC2 is identified by its polypeptide sequence in the sequence listing that accompanies this specification. An SDC2 fragment refers to any set of consecutive residues of SDC2 that uniquely or recognizably map to the SDC2 polypeptide sequence. In some cases an SDC2 fragment retains some or all activity of the SDC2 protein, or acts as an inhibitor of full length or native SDC2. SDC2 also occasionally refers informally herein to the locus or gene encoding the SDC2 protein. In the event that one of skill in the art is unable to distinguish an SDC2 reference, it is presumed that the term is used herein in reference to the protein or polypeptide rather than to the gene, transcript, or an antibody raised against or binding to SDC2. There is a family of syndecan proteins in mammals. SDC2 is used alternately in reference to a mammalian syndecan-2 or to human SDC2 specifically. In the event that one of skill in the art is unable to distinguish an SDC2 reference, it is presumed that the term is used herein in reference to the human protein or polypeptide.

"Extracellular nucleotidases," also known as "apyrases," "E-type nucleotidases," and "NTPases" as used herein are mediators of extracellular nucleotide catabolism. Examples of extracellular nucleotideases include but are not limited to CD39, CD39L1, CD39L2, CD39L3, CD39L4, and CD73. Extracellular nucleotideases herein, in some cases, are cell surface proteins for isolation of SDC2+ stromal stem cells. Extracellular nucleotideases herein, in some cases, mediate catabolism of extracellular ATP to adenosine.

"CD39," also known as ENTPD1, ATPDase, NTPDase-1, SPG64, and ectonucleoside triphosphate diphosphohydrolase 1, refers to the polypeptide encoded by the CD39 locus. Generally, as used herein, CD39 refers to the protein or a recognizable fragment thereof unless otherwise indicated, for example by reciting 'the CD39 gene,' 'the CD39 transcript,' 'a CD39 antibody.' CD 39 is a cell surface protein having an enzyme that catalyses the hydrolysis of $\gamma$ and $\beta$ phosphate residues of triphospho- and diphosphonucleosides to the monophosphonucleoside derivative. In some cases, CD39 hydrolyzes extracellular ATP to extracellular adenosine.

"CD39L3," also known as ENTPD3, HB6, NTPDase-3, or ectonucleoside triphosphage diphosphohydrolase 3, refers to the polypeptide encoded by the CD39L3 locus. Generally, as used herein, CD39L3 refers to the protein or a recognizable fragment thereof unless otherwise indicated, for example by reciting 'the CD39L3 gene,' 'the CD39L3 transcript,' 'a CD39L3 antibody.' CD 39L3 is a cell surface protein having an enzyme that catalyses the hydrolysis of $\gamma$ and $\beta$ phosphate residues of triphospho- and diphosphonucleosides to the monophosphonucleoside derivative. In some cases, CD39L3 hydrolyzes extracellular ATP to extracellular adenosine.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating," and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

The terms "pharmaceutically acceptable", "physiologically tolerable" and grammatical variations thereof, as they refer to compositions, carriers, diluents and reagents, are used interchangeably and in some cases, represent that the materials are capable of administration to or upon a human without the production of undesirable physiological effects to a degree that would prohibit administration of the composition.

A "therapeutically effective amount" in some cases means the amount that, when administered to a subject for treating a disease, is sufficient to effect treatment for that disease.

As used herein, the term "about" a number refers to a range spanning that from 10% less than that number through 10% more than that number, and including values within the range such as the number itself.

As used herein, the term "comprising" an element or elements of a claim refers to those elements but does not preclude the inclusion of an additional element or elements.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Isolation of SDC2+ Stromal Stem Cells from Umbilical Cord

Cells were isolated from human umbilical cord and stromal stem cells were purified using FACS, gating for live, single cells, CD39 and CD362 (SDC2) using a Miltenyi MACSQuant Tyto microchip cell sorter (FIG. 1A, FIG. 1B). The population was analyzed at it was found that the percentage of the population that is CD362+ was the same as the percentage of the population that is CD39+/CD362+, 0.10% (FIG. 1C). Colony forming activity was measured on the CD39+/CD362+ cells and it was found that they formed colonies at a rate of 1/2352 when plated at 40 k cells per well and a rate of 1/1666 when plated at 10 k cells per well (FIG. 1D). This is compared to unsorted cells which formed colonies at a rate of 1/9090 when plated at 200 k cells per well and a rate of 1/9375 when plated at 100 k cells per well (FIG. 1E). Therefore, stromal stem cells isolated using CD39 as a marker perform as well or better than stromal stem cells isolated using CD362 as a marker.

Example 2

Isolation of SDC2+ Stromal Stem Cells from Bone Marrow

Cells were isolated from human bone marrow and stromal stem cells were purified using FACS with a BD FACSAria cell sorter isolating CD39−/CD362+, CD39+/CD362+, and CD39+/CD362− fractions (FIG. 2A). The populations were analyzed and it was found that CD39+/CD362+ cells accounted for about 0.4% of the population while CD39 hi/CD362+ cells accounted for 0.02% of the population (FIG. 2B). Therefore, most CD362+ cells were found to be also CD39+. Sorted cells were further analyzed for colony formation (FIG. 2C) showing that unsorted bone marrow cells (wild type) form colonies at a rate of 1/18750 to 1/50000; CD39−/CD362+ cells form colonies at a rate of 0 to 1/11; CD39+/CD362+ cells form colonies at a rate of 1/46-1/4; and CD39+/CD362− and double negative cells form colonies at a rate of 0.

In an alternative method, cells were isolated from human bone marrow and stromal stem cells were purified using FACS with a Miltenyi MACSQuant Tyto microchip cell sorter isolating CD39−/CD362+, CD39+/CD362+, and CD39+/CD362− fractions (FIG. 3A). Sorted cells were further analyzed for colony formation comparing results of the BD FACSAria with the Miltenyi MACSQuant Tyto (FIG. 3B) showing that unsorted bone marrow cells (wild type) form colonies at a rate of 1/50000 to 1/18750 (BD) versus 1/14285 (Tyto); CD39−/CD362+ cells form colonies at a rate of 0-1/11 (BD; CD39+/CD362+ cells form colonies at a rate of 1/46 to 1/4 (BD) versus 1/16.6 (Tyto); CD39+/CD362− cells form colonies at a rate of 0 (BD); and double negative cells form colonies at a rate of 0 (BD) versus 1/100000 to 1/16.6 (Tyto).

Example 3

Treatment of Diabetic Ulcers

A therapeutically active CD39+/SDC2+ cell composition is used to treat an individual who is in need of treatment of diabetic ulcers. A doctor applies the therapeutically active CD39+/SDC2+ cell composition formulated with a collagen ointment for topical use to the diabetic ulcers. One week after administration of the composition to the diabetic ulcers, the ulcers have decreased in severity. Optionally, the patient returns for another administration of the composition. One month after administration of the composition to the diabetic ulcers, the ulcers have largely healed.

Example 4

Treatment of Inflammatory Liver Disease

A therapeutically active CD39+/SDC2+ cell composition is used to treat an individual who is in need of treatment of autoimmune hepatitis. A doctor administers the therapeutically active in vitro SDC2+ cell composition formulated for intravenous. After administration of the composition to the subject, liver function of the individual improves and the individual does not require a liver transplant.

Example 5

Scratch Wound Assay

A scratch wound assay is performed on A549 cells to observe the effect of CD39+/SDC2+ cells on cell migration. In this assay, 300,000 A549 cells are grown in a monolayer in a 24 well plate. The cells are scraped with a p200 pipet tip in a straight line to create a scratch. An image is taken at the time of scraping (0 h) and after a 48 hour incubation with serum free media or $10^6$ CD39+/SDC2+ cells in serum free media. Incubation with cells results in a reduced scratch size compared to serum free media.

This example shows increased cell migration in cells treated with CD39+/SDC2+ cells compared to cells treated with serum free media alone.

Example 6

NFκB Reporter Assay

An NFκB assay is performed on A549 cells treated with serum free media or CD39+/SDC2+ cells in serum free media. In this assay, 30,000 A549 cells that are transfected with an NFκB-luciferase reporter gene are grown in a 96 well dish. The cells are treated with serum free media or $10^5$ CD39+/SDC2+ cells in serum free media for 24 hours and then are stimulated with human IL-1β for 24 hours and luciferase activity is measured. A reduction is observed in luciferase activity in A549 cells treated with CD39+/SDC2+.

This example shows a reduction in the inflammatory response in cells treated with CD39+/SDC2+ cells compared to cells treated with serum free media alone.

Example 7

Exosome Delivery to Treat ARDS Lung Injury

CD39+/SDC2+ cells are tested in a rat model of ARDS. Briefly, 300 g Sprague Dawley rats are given an intrapulmonary dose of *E. coli* to induce ARDS lung injury, one hour later, the rats are treated with an intravenous dose of 200 µg or 10 mill/kg CD39+/SDC2+ cells. The extent of lung injury is then measured 24 hours later by measurement of arterial oxygen, BAL bacterial load, BAL cell infiltration, static compliance, and a lung wet dry ratio. An improvement in arterial FI 0.3 is observed by treatment with CD39+/SDC2+ cells compared to vehicle (one way anova p<0.0001). An improvement is also observed in arterial FI 1.0 observed by treatment with CD39+/SDC2+ cells compared to vehicle (one way anova p<0.0001). This demonstrates that CD39+/SDC2+ cells are able to treat lung damage in an ARDS lung injury model.

Static lung compliance is also measured in rats treated with CD39+/SDC2+ cells compared to PBS vehicle control. This measurement shows CD39+/SDC2+ cells effective in treating ARDS lung injury compared to control (one way anova p<0.01).

Bacterial load is measured in the bronchioalveolar lavage (BAL). In this measurement, a significant reduction is observed in BAL bacterial load in rats treated with CD39+/SDC2+ cells (one way anova p<0.01). In this assay, a significant difference is observed in BAL total cell count and BAL neutrophil count in rats treated with CD39+/SDC2+ cells compared to vehicle control (one way anova p<0.01).

This example shows CD39+/SDC2+ cells administration with an increased dose and intravenous mode of administration treats ARDS lung injury.

Example 8

Treatment of Diabetes-Associated Kidney Failure

A therapeutically active CD39+/SDC2+ cells composition is used to treat an individual suffering from kidney failure related to diabetes. After administration of the composition to the subject, the symptoms experienced by the patient are decreased. When 10 patients are given the intravenous injections of the composition, 9 experience marked increase in kidney function. When 10 patients are given an alternative treatment, the kidney function is not improved. No impact upon blood glucose levels is observed in some individuals.

Example 9

In Vitro Exosomes

A therapeutically active composition is prepared comprising in vitro SDC2+ exosomes. The SDC2+ exosome composition is prepared to include infliximab contained within the exosome composition. When the composition is administered to the patient, the infliximab is not exposed to the humoral immune system and the patient does not develop humoral immune response toward the infliximab. When a sample of the composition is tested, at least 30% of the exosomes are found to comprise SDC2. The exosome composition is frozen for storage in phosphate buffer alone without the use of a cryoprotectant such as DMSO. When the composition is thawed, there is no loss therapeutic efficacy as measured by inhibition of the inflammatory response.

Example 10

In Vitro Exosomes and SDC2+ Mesenchymal Stromal Stem Cells

A therapeutically active composition is prepared comprising in vitro SDC2+ exosomes. The SDC2+ exosome composition is prepared to include infliximab contained within the exosome composition. When the composition is administered to the patient, the infliximab is not exposed to the humoral immune system and the patient does not develop humoral immune response toward the infliximab. When a sample of the composition is tested, at least 30% of the exosomes are found to comprise SDC2. The exosome composition is combined with SDC2+ mesenchymal stromal stem cells, purified based on expression of CD39. Addition of the exosome composition enhances the therapeutic activity of the SDC2+ mesenchymal stromal stem cells in reducing the inflammatory response.

Example 11

In Vitro Exosomes and Regulatory T Cells

A therapeutically active composition is prepared comprising in vitro SDC2+ exosomes from cells isolated based on expression of CD39. The SDC2+ exosome composition is prepared to include infliximab contained within the exosome composition. When the composition is administered to the patient, the infliximab is not exposed to the humoral immune system and the patient does not develop humoral immune response toward the infliximab. When a sample of the composition is tested, at least 30% of the exosomes are found to comprise SDC2. The exosome composition is combined with CD25+CD4+Foxp3+ regulatory T cells. Addition of the exosome composition enhances the therapeutic activity of the CD25+CD4+Foxp3+ regulatory T cells in reducing the inflammatory response.

Example 12

Treatment of Diabetic Ulcers

A therapeutically active in vitro SDC2+ exosome composition is used to treat an individual who is in need of treatment of diabetic ulcers. A doctor prescribes the therapeutically active in vitro SDC2+ exosome composition formulated with a collagen ointment for topical use and instructs the patient to administer the composition 1-5 times per week to the diabetic ulcers. After administration of the composition to the diabetic ulcers for one week, the ulcers have decreased in severity. After administration of the composition to the diabetic ulcers for one month, the ulcers have largely healed.

Example 13

Treatment of Rheumatoid Arthritis

A therapeutically active in vitro SDC2+ exosome composition additionally comprising infliximab is used to treat an individual who is in need of treatment of rheumatoid arthritis. A doctor prescribes the therapeutically active in vitro SDC2+ exosome composition formulated for subcutaneous administration and instructs the patient to administer the composition weekly by subcutaneous injection. After administration of the composition to the subject, the joint pain experienced by the patient is decreased by at least 50% and the joint mobility of the patient is increased by at least 60%. Further, the patient does not experience a humoral immune response to infliximab.

Example 14

Treatment of Amyotrophic Lateral Sclerosis

A therapeutically active in vitro SDC2+ exosome composition is used to treat an individual who is in need of treatment of amyotrophic lateral sclerosis (ALS). A doctor prescribes the therapeutically active in vitro SDC2+ exosome composition formulated for intrathecal administration at the doctor's office and instructs the patient to come for weekly intrathecal injections. After administration of the composition to the subject, the symptoms experienced by the patient are decreased. When 10 patients are given the intrathecal injections of the composition, 8 of them experience minimal decrease in motor neuron function and stabilization of their condition. When 10 patients are given an alternative treatment, 3 of them experience minimal decrease minimal decrease in motor neuron function and stabilization of their condition.

Example 15

Isolation

An immuno-modulatory composition is obtained by isolating exosomes that express SDC2. The composition is isolated from SDC2+ stromal cells that have been transformed with a lentivirus that carries the SDC2 gene such that the SDC2+ stromal cells are over-expressing SDC2. Over-expression of SDC2 has the effect of increasing the number of SDC2+ exosomes and as a consequence increases the efficiency of isolating the exosomes and the potency of the exosomes produced by the cells.

The isolated exosomes are analyzed and it is determined that at least 20% of the exosomes are SDC2+ and 700 mg of exosomes are obtained. The exosomes are diluted using a phosphate buffer and frozen without DMSO in single use vials until needed for use.

Example 16

Isolation Using Antibody Purification

An immuno-modulatory composition is obtained by isolating exosomes that express SDC2. The composition is isolated from SDC2+ stromal cells that have been transformed with a lentivirus or adenovirus that carries the SDC2 gene such that the SDC2+ stromal cells are over-expressing SDC2. Over-expression of SDC2 has the effect of increasing the number of SDC2+ exosomes and as a consequence increases the efficiency of isolating the exosomes. The composition comprising exosomes is incubated with an anti-SDC2 antibody for 10-30 minutes or overnight at 4° C. The SDC2+ exosomes are isolated from the solution using flow cytometry based sorting or column chromatography and the SDC2+ exosomes are eluted from the column.

The isolated exosomes are analyzed and it is determined that at least 80% of the exosomes are SDC2+ and 700 mg of exosomes are obtained. The exosomes are diluted using a phosphate buffer and frozen without DMSO in single use vials until needed for use.

Example 17

Isolation Using Ultracentrifugation

An immuno-modulatory composition is obtained by isolating exosomes that express SDC2. The composition is isolated from SDC2+ stromal cells that have been transformed with a lentivirus or adenovirus that carries the SDC2 gene such that the SDC2+ stromal cells are over-expressing SDC2. Over-expression of SDC2 has the effect of increasing the number of SDC2+ exosomes and as a consequence increases the efficiency of isolating the exosomes. Supernatant from the SDC2+ cells containing the exosomes is subjected to ultracentrifugation at 100,000×g force for 16 hours at 4° C. The exosome fraction is isolated from the media solution. For some uses, ultrafiltration with a subsequent liquid chromatography (UF-LC) steps is performed on the resulting product to produce a more pure preparation of SDC2+ exosomes.

The isolated exosomes are analyzed and it is determined that at least 80% of the exosomes are SDC2+ and 700 mg of exosomes are obtained. The exosomes are diluted using a phosphate buffer and frozen without DMSO in single use vials until needed for use.

Example 18

Isolation Using Hollow-Fiber Bioreactors (HFBRs)

Human mesenchymal stem cells (MSCs), such as SDC2+ MSCs are grown in a C2011 cartridge (FiberCell Systems), or alternatively in a Terumo Quantum Cell Expansion System, seeded with $1 \times 10^7$ to $1 \times 10^8$ MSCs. It continuously produces exosomes for 10 weeks. The typical harvest from the extracapillary space of the cartridge is $1.1 \times 10^{12}$ exosomes/ml in a volume of 400 ml. The total bioreactor yield or exosomes by number is approximately 10-fold higher at a concentration that was 10-fold higher. Harvests are performed every two weeks, and prior to each harvest, small samples of cells are collected for phenotypic analysis. During these 10 weeks, the culture does not expand based on glucose uptake rate, which remains fairly constant. By orthogonal measure, the phenotype of the cells remains constant as well. Exosomes are continuously harvested without splitting and/or subculturing of the cells.

Example 19

Delivery of an Exosome Composition

An immuno-modulatory signal is delivered to the intracellular space of an individual using exosomes isolated from SDC2+ stem cells. The exosomes are formulated to contain infliximab. The exosomes are administered to the individual subcutaneously and the contents of the exosome are delivered to the intracellular space of the individual, thereby delivering the immuno-modulatory signal. Administration of the exosomes and delivery of the immuno-modulatory signal does not result in a humoral immune response by the individual to the infliximab, thereby increasing the potency of the infliximab.

Example 20

Supplemented Stem Cell Compositions

A therapeutically active composition is prepared comprising in vitro SDC2+ exosomes derived from mesenchymal stromal stem cells. When a sample of the prepared composition is tested, at least 30% of the exosomes are found to comprise SDC2. The SDC2+ exosomes are combined with the mesenchymal stromal stem cells and the resulting mixture is administered to an individual in need of wound healing. The result of this treatment is enhanced wound healing compared to administration of the mesenchymal stromal stem cells alone.

Example 21

Exosome Delivery to Treat ARDS Lung Injury

Exosomes were tested in a rat model of ARDS. Briefly, 300 g Sprague Dawley rats were given an intrapulmonary dose of *E. coli* to induce ARDS lung injury, one hour later, the rats were treated with a 90-100 μg dose of exosomes or 4 million human mesenchymal stem cells (hMSC). The extent of lung injury was then measured 24 hours later by measurement of arterial oxygen, BAL bacterial load, BAL cell infiltration, static compliance, and a lung wet dry ratio. An improvement in arterial FI 0.3 was observed by treatment with exosomes compared to vehicle (FIG. 7). This demonstrates that exosomes are able to treat lung damage in an ARDS lung injury model. Exosome treatment was shown to be safe as PBS vehicle treatment in arterial FI 1.0 measurement which showed a similar measurement between exosome treatment and PBS vehicle control (FIG. 8).

Arterial oxygen was also measured for bone marrow (BM) exosomes and human umbilical cord (HUC) exosome treatment with arterial FI 0.3 (FIG. 9) and arterial FI 1.0 (FIG. 10) compared to PBS vehicle control. In FIG. 9 and FIG. 10, BM exosomes and HUC exosomes were shown to be just as safe as PBS vehicle control on arterial FI 0.3 or FI 1.0.

In FIG. 11 bacterial load was measured in the bronchioalveolar lavage (BAL). In this measurement, a measurable reduction was observed in BAL bacterial load in rats treated with exosomes and hMSC. BAL total cell count and neutrophil count are shown in FIG. 12 and FIG. 13. In this assay, a measurable difference was observed in BAL total cell count and BAL neutrophil count in rats treated with exosomes and hMSC compared to vehicle control.

Static lung compliance and lung wet dry ratio were also measured in rats treated with exosomes and hMSC compared to PBS vehicle control (FIG. 14). This measurement showed exosomes were just as safe as PBS vehicle control. FIG. 15 shows the results of wet dry ratio in rats that were treated with exosomes or hMSC. This also showed that exosomes were just as safe as PBS vehicle control.

This example shows safety and efficacy of exosomes compared to PBS vehicle control.

Example 22

Scratch Wound Assay

A scratch wound assay was performed on A549 cells to observe the effect of exosomes on cell migration. In this assay, 300,000 A549 cells were grown in a monolayer in a 24 well plate. The cells were scraped with a p200 pipet tip in a straight line to create a scratch. An image was taken at the time of scraping (0 h) and after a 48 hour incubation with serum free media or 2 μg SDC2+ exosomes in serum free media. As shown in FIG. 16 and FIG. 17, incubation with exosomes resulted in a reduced scratch size compared to serum free media.

This example shows increased cell migration in cells treated with exosomes compared to cells treated with serum free media alone.

Example 23

NFκB Reporter Assay

An NFκB assay was performed on A549 cells treated with serum free media or exosomes in serum free media. The results of these assays are shown in FIGS. 18-21. In this assay, 30,000 A549 cells that were transfected with an NFκB-luciferase reporter gene were grown in a 96 well dish. The cells were treated with serum free media or 2 μg exosomes in serum free media for 24 hours and then stimulated with human IL-10 for 24 hours and luciferase activity was measured. A reduction was observed in luciferase activity in A549 cells treated with exosomes obtained by ultrafiltration followed by ultracentrifugation (FIG. 18 and FIG. 10) as well as exosomes obtained by ultracentrifugation without ultrafiltration (FIG. 20 and FIG. 21).

This example shows a reduction in the inflammatory response in cells treated with exosomes compared to cells treated with serum free media alone.

Example 24

Exosome Delivery to Treat ARDS Lung Injury

Exosomes were tested in a rat model of ARDS. Briefly, 300 g Sprague Dawley rats were given an intrapulmonary dose of *E. coli* to induce ARDS lung injury, one hour later, the rats were treated with an intravenous dose of 200 μg or 10 mill/kg human mesenchymal stem cells (hMSC). The extent of lung injury was then measured 24 hours later by measurement of arterial oxygen, BAL bacterial load, BAL cell infiltration, static compliance, and a lung wet dry ratio. An improvement in arterial FI 0.3 was observed by treatment with exosomes compared to vehicle (one way anova p<0.0001) (FIG. 22). An improvement was also observed in arterial FI 1.0 was observed by treatment with exosomes compared to vehicle (one way anova p<0.0001) (FIG. 23). This demonstrates that exosomes are able to treat lung damage in an ARDS lung injury model.

Static lung compliance was also measured in rats treated with exosomes or hMSC compared to PBS vehicle control (FIG. 24). This measurement showed exosomes effective in treating ARDS lung injury compared to control (one way anova p<0.01).

In FIG. 25 bacterial load was measured in the bronchioalveolar lavage (BAL). In this measurement, a significant reduction was observed in BAL bacterial load in rats treated with exosomes and hMSC (one way anova p<0.01). BAL total cell count and neutrophil count are shown in FIG. 26 and FIG. 27. In this assay, a significant difference was observed in BAL total cell count and BAL neutrophil count in rats treated with exosomes and hMSC compared to vehicle control (one way anova p<0.01).

This example shows exosome administration with an increased dose and intravenous mode of administration treats ARDS lung injury.

Example 25

Treatment of Diabetes-Associated Kidney Failure

A therapeutically active in vitro SDC2+ exosome composition is used to treat an individual suffering from kidney failure related to diabetes. After administration of the composition to the subject, the symptoms experienced by the patient are decreased. When 10 patients are given the intrathecal injections of the composition, 9 experience marked increase in kidney function. When 10 patients are given an alternative treatment, the kidney function is not improved. No impact upon blood glucose levels is observed in some individuals.

Example 26

Treatment of Alzheimer's Disease

A therapeutically active in vitro SDC2+ exosome composition is used to treat an individual suffering from Alzheimer's disease. After administration of the composition to the subject by intravenous administration, the composition is able to cross the blood brain barrier and treat the brain and Alzheimer's disease symptoms are decreased. When 10 patients are given the intravenous injection of the composition, 9 experience an improvement in memory.

Example 27

Improved SDC2+ Stromal Stem Cells

A SDC2+ stromal stem cell composition is isolated from a human umbilical cord using a CD39 antibody. The composition further comprises CD25+ FoxP3+ regulatory T cells. One third of the cells are transduced with a lentivirus to overexpress CD39, one third of the cells are transduced with a lentivirus to overexpress CD39L3, and one third of the cells are transduced with a lentivirus with no transgene. The SDC2+ stromal stem cell compositions transduced with CD39 or CD39L3 are more effective in inhibition an inflammatory response as measured in a NFκB reporter assay than SDC2+ stromal stem cell compositions transduced with a lentivirus with no transgene. This example shows that SDC2+ stromal stem cell compositions have greater anti-inflammatory activity when transduced with CD39 or CD39L3.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of isolating a population of SDC2+ stromal stem cells from a mixed population of mammalian cells the method comprising: (a) contacting the mixed population of mammalian cells to a CD39 binding agent; (b) isolating cells bound to the CD39 binding agent; and (c) measuring SDC2+ cell abundance in the isolated cells, thereby isolating the population of SDC2+ stromal stem cells.

2. The method of claim 1, wherein the population of SDC2+ stromal stem cells comprise cells selected from the group consisting of human, mouse, rat, and equine cells.

3. The method of claim 1, wherein the mixed population of mammalian cells are obtained from a source selected from at least one of bone marrow, adipose tissue, skeletal muscle, endometrium, placenta, umbilical cord, Wharton's jelly, and cells derived from pluripotent cells.

4. The method of claim 1, wherein the CD39 binding agent comprises an antibody.

5. The method of claim 1, wherein at least 20% of the population of SDC2+ stromal stem cells is SDC2+.

6. The method of claim 1, wherein at least 40% of the population of SDC2+ stromal stem cells is SDC2+.

7. The method of claim 1, wherein at least 70% of the population of SDC2+ stromal stem cells is SDC2+.

8. The method of claim 1, comprising culturing the isolated cells.

9. The method of claim 1, wherein at least 90% of the population of SDC2+ stromal stem cells are CD45−.

* * * * *